US008350018B2

(12) United States Patent
Bensaid et al.

(10) Patent No.: US 8,350,018 B2
(45) Date of Patent: Jan. 8, 2013

(54) **POLYNUCLEOTIDES OF *HAEMOPHILUS PARASUIS* AND ITS USE**

(75) Inventors: Albert Bensaid, Amer (ES); Sonia Pina Pedrero, Amer (ES); Raquel Rivas Adan, Amer (ES); Simone Oliveira, Amer (ES); Enric Espuña Maso, Amer (ES); Carmen Herrero Molina, Amer (ES)

(73) Assignee: Fundacio Centre de Recerca en Sanitat Animal, Barcelona (ES)

( * ) Notice: Subject to any disclaimer, the term of this patent is extended or adjusted under 35 U.S.C. 154(b) by 592 days.

(21) Appl. No.: 12/067,709

(22) PCT Filed: Sep. 15, 2006

(86) PCT No.: PCT/EP2006/009006

§ 371 (c)(1),
(2), (4) Date: Jul. 27, 2010

(87) PCT Pub. No.: WO2007/039070

PCT Pub. Date: Apr. 12, 2007

(65) Prior Publication Data

US 2010/0285070 A1 Nov. 11, 2010

(30) Foreign Application Priority Data

Sep. 21, 2005 (ES) .................................. 200502296

(51) Int. Cl.
*C07H 21/00* (2006.01)

(52) U.S. Cl. ..................................................... 536/23.7

(58) Field of Classification Search ......................... None
See application file for complete search history.

(56) References Cited

U.S. PATENT DOCUMENTS 6,248,329 B1 * 6/2001 Chandrashekar et al. . 424/191.1

OTHER PUBLICATIONS

Oliveira et al., (Can. J. Vet. Res., 68:71-75, 2004).*
Pina et al. (J. Bacteriol., 191:576-587, 2009).*
Ellis (Chapter 29 of Vaccines, Plotkin, et al. (eds) WB Saunders, Philadelphia, 1998, pp. 568-575.*
Bowie et al. (Science, 1990, 247:1306-1310).*
Greenspan et al. (Nature Biotechnology 7: 936-937, 1999).*
Oliveira et al. (J. Vet. Diagn. Invest., 13:495-501, 2001).*
Invitrogen Product Catalog (Invitrogen 1997 Product Catalog, 1997).*
Sambrook et al. (Molecular Cloning, a Laboratory Manual, vol. 3, Cold Spring Harbor Lab Press, 1989, pp. 17.2-17.44).*

* cited by examiner

*Primary Examiner* — Brian J Gangle
(74) *Attorney, Agent, or Firm* — Sughrue Mion, PLLC

(57) ABSTRACT

The present invention relates to *Haemophilus parasuis* polynucleotides produced by recombinant technology. It also relates to polypeptides that are expressed by said polynucleotides and also to a vaccine against *H. parasuis* that comprises said polypeptides. In another aspect, the invention also relates to the use of polynucleotides to determine if a strain of *H. parasuis* is virulent or avirulent.

14 Claims, 6 Drawing Sheets

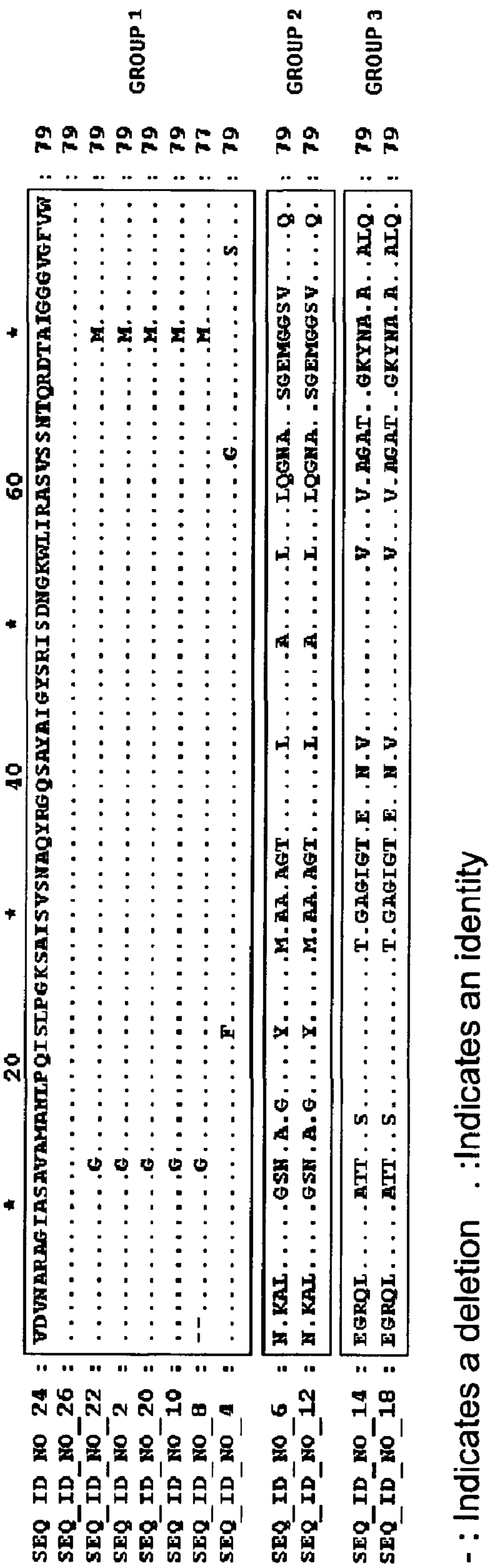

FIGURE 4

|  |  |  | | | | | | | | |
|---|---|---|---|---|---|---|---|---|---|---|
| | | 20 | | 40 | | 60 | | | | |
| SEQ_ID_NO_24 : | VDVNARAGIASAVAMAMLPQISLPGKSAISVSNAQYRGQSAVAIGYSRISDNGKWLIRASVSSNTQRDTAIGGGVGFVW | : | 79 | | GROUP 1 |
| SEQ_ID_NO_26 : | ................................................................................. | : | 79 | | |
| SEQ_ID_NO_22 : | .......G......................................................................M... | : | 79 | | |
| SEQ_ID_NO_2  : | .......G......................................................................M... | : | 79 | | |
| SEQ_ID_NO_20 : | .......G......................................................................M... | : | 79 | | |
| SEQ_ID_NO_10 : | .......G......................................................................M... | : | 79 | | |
| SEQ_ID_NO_8  : | --......................F..............................G.......................... | : | 77 | | |
| SEQ_ID_NO_4  : | ....................................................................S............ | : | 79 | | |
| SEQ_ID_NO_6  : | N.KAI....GSN.A.G....Y......M.AA.AGT......A......L...LQGNA..SGEMGGSV......Q.. | : | 79 | | GROUP 2 |
| SEQ_ID_NO_12 : | N.KAI....GSN.A.G....Y......M.AA.AGT......A......L...LQGNA..SGEMGGSV......Q.. | : | 79 | | |
| SEQ_ID_NO_14 : | EGRQI....ATT.S..............T.GAGIGT.E..N.V..........V...V.AGAT..GKYNA.A..ALQ. | : | 79 | | GROUP 3 |
| SEQ_ID_NO_18 : | EGRQI....ATT.S..............T.GAGIGT.E..N.V..........V...V.AGAT..GKYNA.A..ALQ. | : | 79 | | |

-: Indicates a deletion    .: Indicates an identity

FIGURE 6A

```
HP2269-2-j-1:  2    VSELVKSHTKTSAYTDKRSQLCTSDYFLHKQQDKFKLSLLSLVLLSIFFSPVGLAVFIQD 181
                    VSELVKSHTKTSAYTDKR+Q+CTSDYFL KQQDKFKLSLLSLVLL IFFSPVG A ++ D
SEQ ID NO: 16: 19   VSELVKSHTKTSAYTDKRAQVCTSDYFLDKQQDKFKLSLLSLVLLGIFFSPVGSAAWLVD 78

HP2269-2-j-1:  182  GSTNVAPFYDNGAIGIGYRSYVGNSGVVIGKHAVARDTVAVAIGYSAEVVGHDGVAVGAH 361
                    GS    +    D G IGIG   S VG    +VIG++A A     ++AIGY AE   G    VAVGA
SEQ ID NO: 16: 79   GSEKGSD-ADAGTIGIGIDSRVGPGSIVIGQYAKAEGRTSIAIGYRAETTGDKAVAVGAT 137

HP2269-2-j-1:  362  AQARYRSVASGYSAKALGQRSVAIGDSAEVNSGATRAIALGHNSIVTVAGGVALGYGSR 538
                    AQA    S A GY A+A     +VA+G   A   N        +ALG+ S V V  GVALG   SR
SEQ ID NO: 16: 138  AQAFNYSAAYGYGAQAKAIGAVAVGQEAIANQNG--GVALGYQSSVNVTNGVALGSFSR 194
```

FIGURE 6B

```
HP2269-2-j-1:  2    VSELVKSHTKTSAYTDKRSQLCTSDYFLHKQQDKFKLSLLSLVLLSIFFSPVGLAVFIQD 181
                    VSELVKSHTKTSAYTDKR+Q+CTSDYF  KQQDKFKLSLLSLVLL IFFS VG A +++
SEQ ID NO: 12: 19   VSELVKSHTKTSAYTDKRAQVCTSDYFFSKQQDKFKLSLLSLVLLGIFFSSVGSAAYLEY 78

HP2269-2-j-1:  182  GSTNVAPFYDNGAIGIGYRSYVGNSGVVIGKHAVARDTVAVAIGYSAEVVGHDGVAVGAH 361
                    G+   V        G+IGIG   S VG + + IG +A AR   VAVAIGY A+ + +D  AVG
SEQ ID NO: 12: 79   GARAVNS-GSRGSIGIGIGSTVGYASIGIGDNANARGEVAVAIGYGAQSINNDATAVGRA 137

HP2269-2-j-1:  362  AQARYRSVASGYSAKALGQRSVAIGDSAEVNSGATRAIALGHNSIVTVAGGVALGY 529
                    +QA YRS A G+ AKA G+ SVAIG+ A VN G  RAIA+G  S        +A+GY
SEQ ID NO: 12: 138  SQAGYRSAAYGFDAKAQGEGSVAIGNQATVN-GNARAIAIGQQSKAEGQNVIAIGY 192
```

POLYNUCLEOTIDES OF *HAEMOPHILUS PARASUIS* AND ITS USE

This application is a National Stage under 35 U.S.C. 371 of International Application PCT/EP2006/009006, filed Sep. 15, 2006, which claims priority to Spanish Patent Application No. P 20052296, filed Sep. 21, 2005.

FIELD OF THE INVENTION

The present invention is within the field of development of vaccines against *Haemophilus parasuis* which comprise polypeptides produced by recombinant technology.

PRIOR ART

The *H. parasuis* bacteria is the causal agent of Glässer's disease (porcine polyserositis-arthritis) which has important economic repercussions on the swine industry.

It is considered that the maternal immunity provided by colostrum is a determining factor in preventing the disease. The practice of early weaning of the piglets has increased the frequency of this disease and has increased the use of vaccines.

*H. parasuis* is a commensal bacteria of the upper respiratory tract which only causes disease when it comes to colonize the lower respiratory tract and, in particular, the lungs, causing pneumonias.

Certain highly virulent strains cross the lung barrier and colonize serum tissues causing serositis, pericarditis, arthritis and, in certain circumstances, meningitis. Consequently, certain *H. parasuis* strains have the power of colonizing and invading numerous tissues in contrast with the avirulent strains that are localized in the upper respiratory tract.

One of the essential characteristics of *H. parasuis* is its antigenic variability, which greatly reduces the efficacy of the vaccines.

There exist at least 15 serotypes, as an important number of strains are untypable, and when experimental infections are proceeded with in swine the degree of virulence varies depending on the strain.

Kielstein et al., J. Clin. Micro. 30: 4: 862 (1992) describes that there exists a correlation between serotypes and the degree of virulence of the strain. It is considered that the strains of serotype 1, 5, 10 and 12 are highly virulent whilst those of serotype 2, 4 and 15 are moderately virulent and those of serotype 3, 6, 7, 9 and 11 are avirulent. Nevertheless, this serological classification is not absolute and in practice numerous exceptions to this rule are observed.

A commercial diagnostic method to classify the *H. parasuis* strains as virulent and avirulent is not known, for which reason it would be desirable to have a method that permitted determining if an *H. parasuis* strain is virulent or not, without having to wait until the symptoms of the disease became manifest and be able to proceed with the possible treatment thereof without delay.

To protect swine against *H. parasuis*, vaccines are used that comprise inactivated bacteria (bacterins), but efficacy is limited as they induce a humoral immune response, essentially aimed against lipopolysaccharides which may vary from one strain to another.

Patent application WO-A-00/01408 discloses vaccines against the infections caused by *H. parasuis* which use a cellular extract of bacteria which has a toxic activity when administered intraperitoneally to swine, but which has a protective action when administered intramuscularly in the presence of an adjuvant.

For the moment, the molecular nature of the antigens responsible for the immune response and protection have not been characterized. It is only known that the toxic activity of the cell extract resides in a protein fraction of high molecular weight This has also been observed in the case of another species such as *Haemophilus influenzae*, since Hendrixson et al., Mol. Cell. 2: 841 (1998) describes that the molecules responsible for the colonization and invasion of tissues are membrane glycoproteins with autotransporter properties, called adhesins, invasins or hemaglutinins.

For said *H. influenzae* species, patent application WO-A-96/30519 discloses vaccines against the infections caused by said bacteria that contains adhesion proteins produced by recombinant technology.

However, the main drawback to developing vaccines that give good immunological protection lies in the lack of knowledge of the *H. parasuis* genome, and, in particular, of the polynucleotides that code for the adhesins, invasins or hemaglutinins of *H. parasuis*.

There is still the need, therefore, to have effective vaccines against the infections caused by *H. parasuis*.

The authors of this invention have developed a vaccine against the infections caused by *H. parasuis* which include polypeptides produced by recombinant technology.

OBJECT OF THE INVENTION

The object of the present invention is to provide *H. parasuis* polynucleotides.

In a second aspect, the object of the invention is the polypeptides expressed by the polynucleotides of the invention.

In a third aspect, another object of the invention is an expression vector that comprises at least one *H. parasuis* polynucleotide of the invention.

In a fourth aspect, another object of the invention is a host cell transformed with an expression vector which comprises at least one *H. parasuis* polynucleotide of the invention.

In a fifth aspect, another object of the invention is procedure for the preparation of the recombinant polypeptides of *H. parasuis*.

In a sixth aspect, another object of the invention is the use of the polypeptides of the invention for the preparation of vaccines and/or immunogenic compositions.

In a seventh aspect, another object of the invention is a vaccine against the infections caused by *H. parasuis*.

In an eighth aspect, another object of the invention is the use of the polynucleotides to determine if an *H. parasuis* strain is virulent or avirulent.

In a ninth aspect, another object of the invention is kit to determine if an *H. parasuis* strain is virulent or avirulent.

Figure 3:
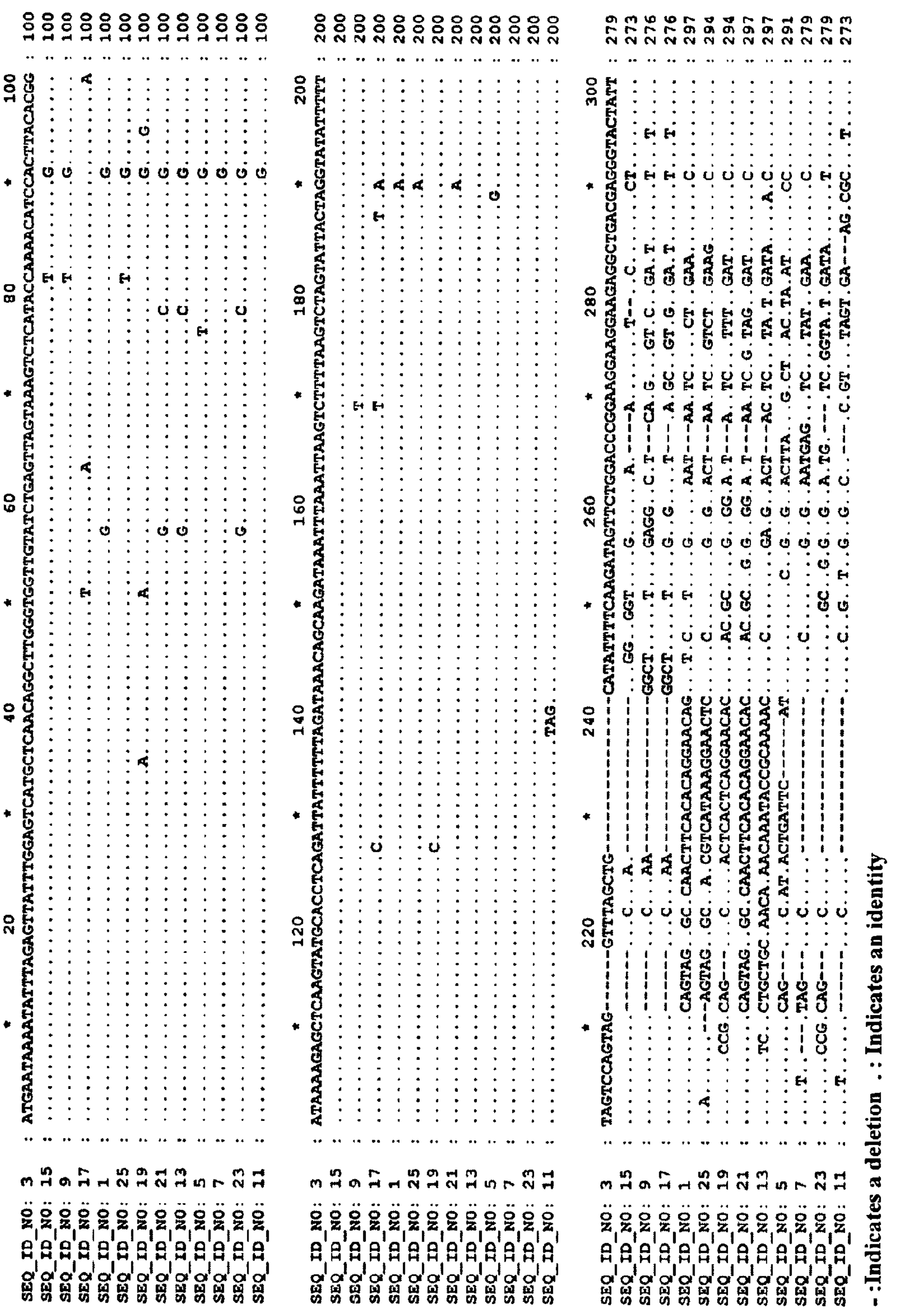

FIG. 3 shows the multiple alignment of the polynucleotides that code for the 5' terminal parts of the *H. parasuis* polypeptides. Good conservation is observed in the 206 nucleotides, and there is complete identity for the first 36 nucleotides.

FIG. 4 shows the multiple alignment of the amino acids of the *H. parasuis* polypeptides. The polypeptides can be grouped in three structural groups called group 1, group 2 and group 3. Group 1 comprises the polypeptides SEQ ID NO: 2, SEQ ID NO: 4, SEQ ID NO: 8, SEQ ID NO: 10, SEQ ID NO: 20, SEQ ID NO: 22, SEQ ID NO: 24 and SEQ ID NO: 26. Group 2 comprises the polypeptides SEQ ID NO: 6 and SEQ ID NO: 12. Group 3 comprises the polypeptides SEQ ID NO: 14 and SEQ ID NO: 18.

FIG. 5 shows the agarose gel electrophoresis of polynucleotide amplification products of the invention of several virulent and non-virulent strains of *H. parasuis.*

Figure 5A:
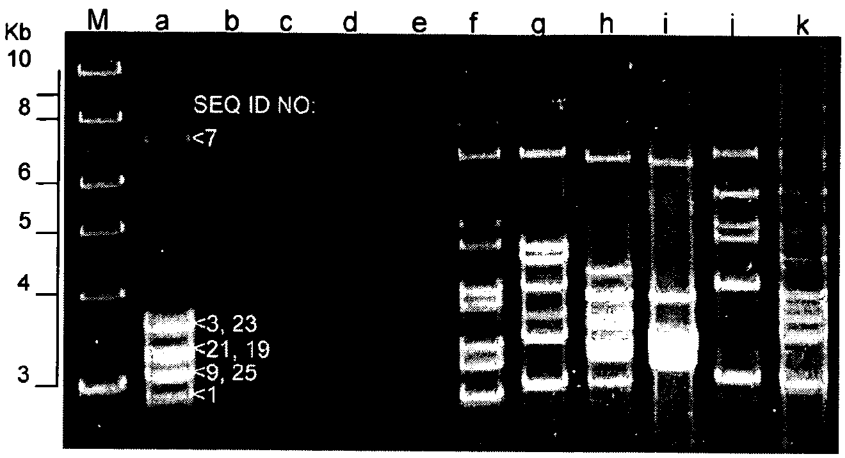

FIG. 5A shows the amplification products corresponding to the polynucleotides of group 1, defined by the sequences SEQ ID NO: 1, SEQ ID NO: 3, SEQ ID NO: 7, SEQ ID NO: 9, SEQ ID NO 19, SEQ ID NO: 21, SEQ ID NO: 23 and SEQ ID NO: 25.

Figure 5B:
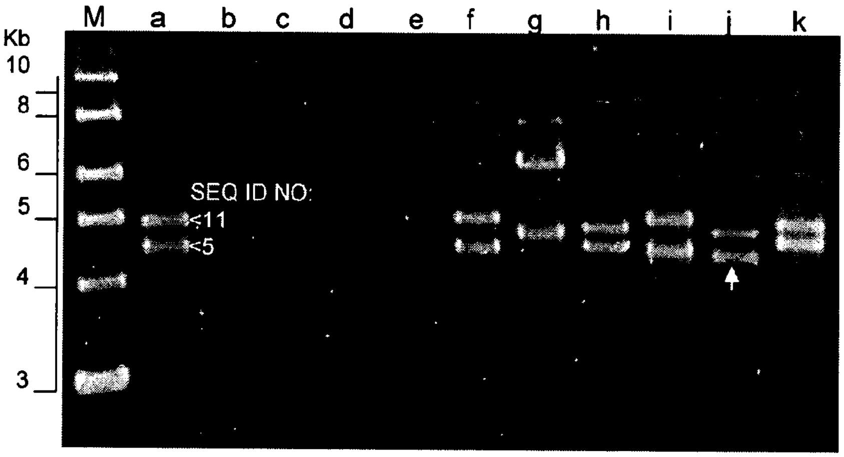

FIG. 5B shows the amplification products corresponding to the polynucleotides of group 2, defined by the sequences SEQ ID NO: 5 and SEQ ID NO: 11.

Figure 5C:
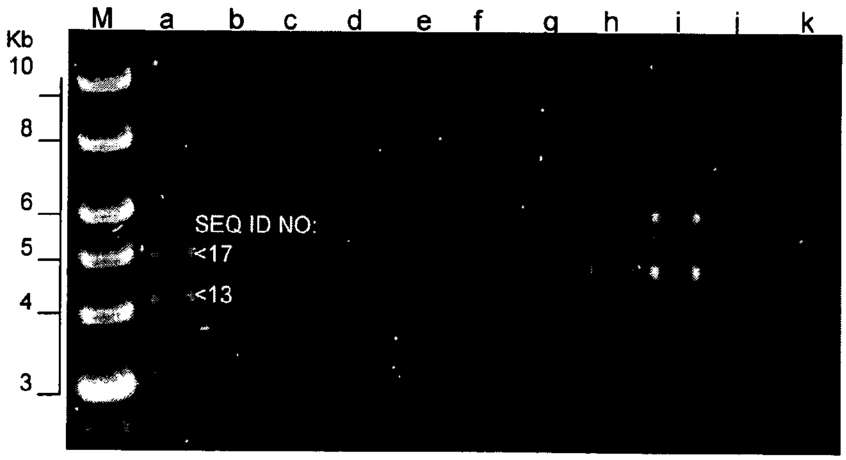

FIG. 5C shows the amplification products corresponding to the polynucleotides of group 3 defined by the sequences SEQ ID NO: 13 and SEQ ID NO: 17.

Lane M shows a 1 kb ladder (New England Biolabs), which has been used as a marker of molecular weight.

Lane a shows the amplification products corresponding to the *H. parasuis* strain (Nagasaki), which is a highly virulent reference strain of serotype 5, experimentally reproducing Glässer's disease.

Columns b-e show the amplification products corresponding to isolated strains of the nasal cavity in swine which did not show any symptoms or lesions characteristic of Glässer's disease and/or from farms without a history of the disease.

Columns f-k show the amplification products corresponding to isolated strains of different organs of swine with confirmed Glässer's disease.

In FIG. 5B, the arrow situated over a band of column j indicates the PCR product of the virulent HP2269 strain which has been sequenced with the primer pADH-F (SEQ ID NO: 27), and which expresses a polypeptide called HP2269-2-j-1. The nomenclature used identifies the strain: HP2269, group: 2, the lane of the electrophoresis: j, and the band position beginning from the lowest molecular weight: 1.

FIG. 6

FIG. 6 shows the result of the comparison of the sequence of amino acids corresponding to the polypeptide called HP2269-2-j-1 (SEQ ID NO: 40). Said polypeptide is expressed by the PCR product belonging to the polynucleotide of lower molecular weight of group 2 of HP2269 strain (band marked by an arrow in FIG. 5). The sequence of polynucleotides produced with the primer pADH-F (SEQ ID NO: 27) is translated in silico, and the resulting polypeptide sequence is compared with the sequences of the polypeptides of the invention by the blastX program.

FIG. 6A shows the alignment produced with SEQ ID NO: 40 and the polypeptide SEQ ID NO: 16 belonging to group 1, and the resulting consensus sequence displaying those residues between SEQ ID NOs: 40 and 16 that are conserved (i.e., residues 1-18, 20, 22-28, 30-45, 47-53, 55, 60-62, 70, 72, 74-77, 80, 82, 83, 88-90, 93, 95, 102-105, 107, 108, 111, 115-119, 121-123, 127, 129, 131, 132, 134, 136, 142, 143, 145, 148, 151, 159-161, 164, 166, 168, 171-175, 178 and 179 of SEQ ID NO: 40) or semi-conserved (indicated by a "+" symbol). FIG. 6B shows the alignment produced with SEQ ID NO: 40 and the polypeptide SEQ ID NO: 12, belonging to group 2, and the resulting consensus sequence displaying those residues between SEQ ID NOs: 40 and 12 that are conserved (i.e., residues 1-18, 20, 22-27, 30-45, 47-50, 52, 53, 55, 61, 65, 72, 74-77, 80, 82, 83, 89, 90, 93, 95, 96, 99-105, 107, 113, 116-118, 122, 123, 125-127, 129, 131, 134-136, 138, 141-145, 148, 150, 151, 153, 156-159, 161, 164, 173, 175 and 176 of SEQ ID NO: 40) or semi-conserved (indicated by a "+" symbol). In both cases, the sequence of amino acids of the polypeptide HP2269-2-j-1 has 59% identity.

DETAILED DESCRIPTION OF THE INVENTION

Identification of the Polynucleotides

The present invention provides polynucleotides which have been identified after sequencing the genome of the *H. parasuis* strain (Nagasaki), which is a highly virulent reference strain of serotype 5, experimentally reproducing Glässer's disease (Takahashi et al., J. Vet. Med. Sci. 63: 487 (2001)).

The polynucleotides of the invention have in common the fact that they express polypeptides that have a significant homology with autotransporters, adhesins, invasins, hemaglutinins, and external membrane proteins present in various protobacteria, i.e. they express polypeptides that are exposed on the bacteria surface to the antibodies of the host's immune system, so that they are appropriate for preparing vaccines against the infections caused by *H. parasuis.*

The object of the invention relates to an *H. parasuis* polynucleotide which has a sequence selected from the group formed by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

Figure 1:
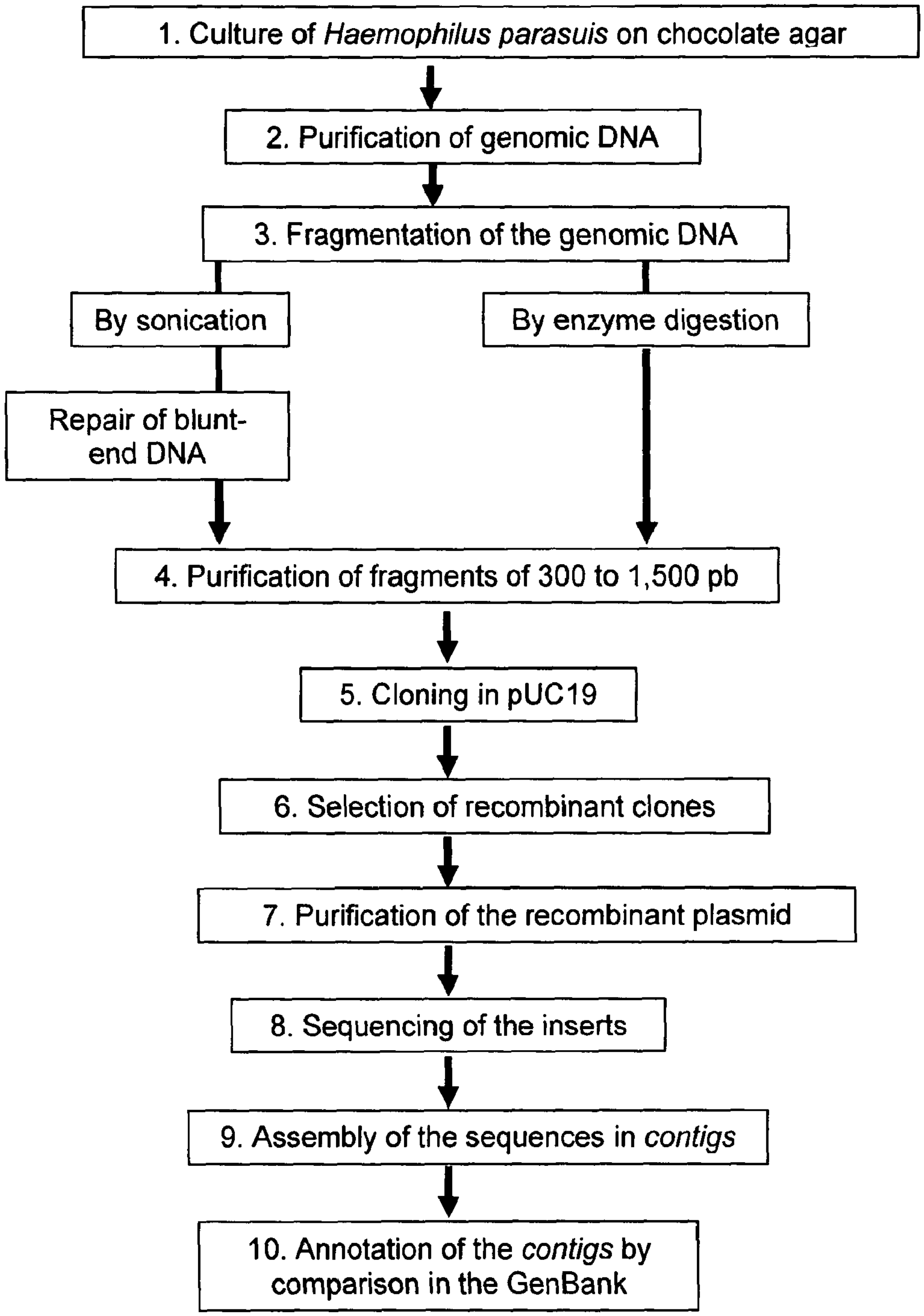
FIG. 1 shows a diagram of the different technical stages that lead to the sequencing and annotation of the genes and proteins that code for polypeptides considered autotransporters, adhesins, invasins or hemaglutinins of *H. parasuis*.

The procedure used to identify the polynucleotides comprises the combination of recombinant techniques with computer processing, as is shown in the diagram of FIG. 1.

The experimental methods that are used in the identification procedure of the polynucleotides of the invention constitute techniques well known by the person skilled in the art, and which are well described, e.g. in the book by Sambrook et al., op.cit.

The person skilled in the art also has complementary information that consists of the documentation that usually accompanies the biochemical products and equipment, wherein the manufacturer suggests procedures for the use of the products and equipment.

In accordance with the diagram of FIG. 1, the experimental procedure that is followed to identify the polynucleotides of the invention comprises the following stages:

1.—Culture of a Virulent *H. parasuis* Strain

For the purification of genomic DNA and the realization of gene banks, the Nagasaki strain of *H. parasuis* is taken, donated by Dr. Pat Blackall of the Animal Research Institute (Queensland, Australia), which is a virulent strain of serotype 5.

The strain is cultured on six 90 mm diameter plates, inoculated to saturation on chocolate agar (Bio Mérieux) in an oven at 37° C. with 5% $CO_2$ during 48 hours. $3\times10^{10}$ colony forming units are produced (CFUs).

2.—Purification of the Genomic DNA of *H. parasuis*

The bacteria are recovered from the plates by resuspending in PBS buffer solution (Amresco) and they are sedimented by centrifugation at 3000 g. The supernatant is eliminated and the bacteria sediment is briefly resuspended. The genomic NDA is then purified using the Genomic-tip 100/G kit (Qiagen). At the end of the purification process, the integrity of the DNA is checked by agarose gel electrophoresis, producing a unique band with a molecular weight over 30,000 pb (base pairs).

3.1—Fragmentation of the Genomic DNA by Enzyme Digestion.

Two restriction enzymes are used, Sau 3AI and Rsa I (New England Biolabs) to fragment the genomic DNA of *H. parasuis* with the suitable reaction buffers and the bovine serum albumin (BSA) provided by the manufacturer. The restriction enzyme Sau 3AI generates sticky fragments in the *H. parasuis* DNA and the Rsa I enzyme blunt-end fragments. In both cases, the fragments have a size largely between 300 and 1,200 pb which makes them suitable for being cloned in plasmids.

3.2.—Fragmentation of the Genomic DNA by Sonication.

Treatment with ultrasounds randomly fragments genomic DNA. The sonication is carried out on a DNA solution of *H. parasuis* in a B. Braun Labsonic U sonicator. Sonication cycles are performed at different times with different power according to conventional methods well known by the person skilled in the art.

The fragments of sonicated DNA have a size between 100 and 1,500 pb, and most of them are between 400 and 900 pb, and they become fragments with blunt-ends by the use of the T4 polymerase enzyme (New England Biolabs).

4.—Agarose Gel Purification by Digested or Sonicated DNA Fragments

Digested or sonicated genomic DNA fragments of *H. parasuis* are purified in an agarose gel.

With the DNA digested with Sau 3AI, fragments of 300 to 600 pb are recovered; with the DNA digested with Rsa I, fragments of 400 to 800 pb are recovered, and with the sonicated DNA, fragments of 400 to 1500 pb are recovered.

The extraction of the DNA fragments contained in pieces of gel are carried out with the QIAquick Gel Extraction kit (Qiagen) or the MinElute Gel Extraction kit (Qiagen).

The fragments of purified DNA are quantified by the migration of an aliquot in agarose gel in which a standard of quantified DNA (pUC19 of New England Biolabs) has also been migrated.

5.—Cloning of DNA Fragments in the pUC19 Plasmid

The pUC19 plasmid (New England Biolabs) is a plasmid with a high number of copies with multiple cloning sites in the beta-galactosidase gene which enables inserting DNA fragments with high efficacy.

To be able to insert the DNA fragments produced by digestion and by sonication, the plasmid is prepared so that it is compatible with the sticky or blunt ends of the DNA fragments produced.

The preparation of the plasmid consists in cutting it with the enzymes appropriate to generate sticky or blunt ends, and in the dephosphorylation of the ends of the plasmid with a phosphatase to avoid its cycling.

To prepare the pUC19 plasmid with the aim of inserting the fragments of genomic DNA of *H. parasuis* generated by the restriction enzyme Sau 3AI, two cycles are performed, each one including a digestion with Bam HI (New England Biolabs), a purification with the MinElute Reaction Cleanup kit (Qiagen), and a dephosphorylation with calf intestinal phosphatase CIP (New England Biolabs), followed by a purification with the MinElute Reaction Cleanup kit (Qiagen).

To insert the fragments of genomic DNA of *H. parasuis* generated by the restriction enzyme Rsa I in the pUC19 plasmid, the restriction enzyme Sma I (New England Biolabs) is used, and the dephosphorylation of pUC19 is performed with bacterial alkaline phosphatase BAP (Invitrogen) without prior purification of the digested product. The dephosphorylated plasmid, after a migration in agarose gel, is purified with the MinElute Gel Extraction kit (Qiagen).

In the case of the insertion of the genomic DNA fragments of *H. parasuis* generated by sonication, the restriction enzyme Sma I (New England Biolabs) is used to cut the pUC19 plasmid. In this case, dephosphorylation is performed with three variants to improve the insertion capacities of this plasmid:

a) with calf intestinal phosphatase CIP (New England Biolabs),
b) with bacterial alkaline phosphatase BAP (Invitrogen), and
c) with a stage of prior purification in agarose gel using the MinElute Gel Extraction kit (Qiagen), and then the dephosphorylation is performed with calf intestinal phosphatase CIP (New England Biolabs)

Finally, after an agarose gel migration, the dephosphorylated plasmids are purified with the MinElute Gel Extraction kit (Qiagen), and quantified by migration of an aliquot in agarose gel in which a quantified DNA standard is jointly migrated (pUC19 of New England Biolabs).

Although gene banks are made and used with all the described preparations, preparation method c) is more effective.

The insertion of DNA fragments of *H. parasuis* (Nagasaki) in dephosphorylated fragments is performed with T4 ligase (Quick Ligation Kit, New England Biolabs). The reaction products are then purified with the MinElute Reaction Cleanup kit (Qiagen), performed with the milliQ water elution.

Electrocompetent *E. coli* DH5α or DH10B bacteria, which are defective in the lac Z gene of the beta galactosidase and sensitive to ampicillin are used. Said bacteria are transformed by electroporation with the purified ligation products.

In this way, recombinant bacteria are produced; most of which incorporate the pUC19 plasmid with insertions of DNA fragments of *H. parasuis.*

6.—Selection of Recombinant Clones

The colonies of bacteria that incorporate pUC19 with a DNA insertion of *H. parasuis* are white-coloured, while the blue bacteria are those which contain the pUC19 plasmid without the insertion of a DNA fragment of *H. parasuis*. In this way, the appropriate clones can be selected.

Each gene bank typically contains tens of thousands of recombinants. The best results were produced with the pUC19 plasmid cut with dephosphorylated Sma I and purified according to variant c).

7.—Purification of the Recombinant Plasmids

To purify the recombinant plasmids the following kits can be used:

R.E.A.L Prep 96 BioRobot (Qiagen) and NucleoSpin 96 Flash (Macherey-Nagel) with a robot (BioRobot 3000, Qiagen), or NucleoSpin 96 Flash (Macherey-Nagel) if this process is manually performed.

These kits use the principle of alkaline lysis of the bacteria followed by a neutralization, clarification of the lysate and precipitation of the plasmids by the addition of isopropanol.

Typically, the concentration of the plasmid is between 50 and 150 ng/μl.

8.—Sequencing of DNA Fragments of *H. parasuis* Cloned in the Plasmids

The large majority of the purified plasmids have a DNA fragment of *H. parasuis* (Nagasaki) inserted in the pUC19 cloning site.

The inserts are sequenced by one or another of two universal primers situated at the two ends of the cloning site by extension with the Taq polymerase in the presence of dNTPs (dATP, dGTP, dCTP, and dTTP nucleotides) and ddNTPs; the latter marked with different fluorochromes.

The universal primers that are used are from Eurogentec, and have the sequences.

```
5'-GTAAAACGACGGCCAGT-3'

5'-AACAGCTATGACCATG-3'.
```

23,676 sequences are performed with the BigDye Terminator v3.1 kit (Applied Biosystems) in 96-well plates (Applied Biosystems or Axygen) adaptable to thermocyclers and sequencers from the manufacturer Applied Biosystems.

The reading of the sequences is automatically performed by introducing all the parameters necessary to construct the electropheroframs in computer files.

9.—Assembling of the Sequences.

The present invention uses the Phred chain of programs (Ewing and Green, Genome research, 8: 175, 186(1998)), and Phrap and Consed (Gordon et al., Genome Research, 8: 195 (1998)) to assemble the 23,676 polynucleotides described in section 8.

A contig is the assembly of several sequences of polynucleotides with a significant degree of overlapping.

In total, 721 contigs and 94 orphan sequences (sequences which do not enter within a contig) are produced. Adding the size in nucleotides of all contigs and orphan sequences, 2,139, 054 pb are produced. If we take into consideration that the estimated size of *H. parasuis* (Nagasaki) is approximately 2,500,000 pb, we can consider that more than 80% of the *H. parasuis* genome (Nagasaki) has been covered, with a good sequencing quality.

10.—Annotation of the Contigs and Identification of the *H. parasuis* Polypeptides The annotation of the polynucleotides (contigs) produced in section 9 is performed using the sequence comparison program called blastX with the GenBank database which can be found in the web of the National Center for Biotechnology Information (http://www. at the site ncbi.nlm.nih. gov/ BLAST/).

The program translates in silico the polynucleotides into polypeptides, and those alignments of polypeptides are selected which have greater probability of being homologous with sequences of polypeptides of the type of adhesins, invasins, hemaglutinins and autotransporters of other microorganisms, which are proteins considered responsible for the colonization and invasion of tissues in numerous microorganisms.

The inventors have identified sequences of interest in 13 polynucleotide contigs, which have been called SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

The sequences of the polypeptides compared correspond with the in silico translations of the polynucleotides of the invention, so that the polypeptide defined by the sequence SEQ ID NO: 2 is the in silico translation of the polynucleotide defined by the sequence SEQ ID NO: 1, and so on and so forth until the polypeptide defined by the sequence SEQ ID NO: 26, resulting from the in silico translation of the polynucleotide defined by the sequence SEQ ID NO: 25.

No DNA sequence of other organisms has been identified which has a significant homology with the sequences of the polynucleotides of the invention, when said sequences are compared with the sequences present in the GenBank database using the blastN program.

Therefore, the sequences of polynucleotides of the invention are new. They also have a good degree of homology between them, which is revealed in the multiple alignment of the 5' ends of all the polynucleotides of the invention (FIG. 3). Said multiple alignment shows good conservation in the first 206 nucleotides, the identity being complete for the first 36 nucleotides.

Figure 2:
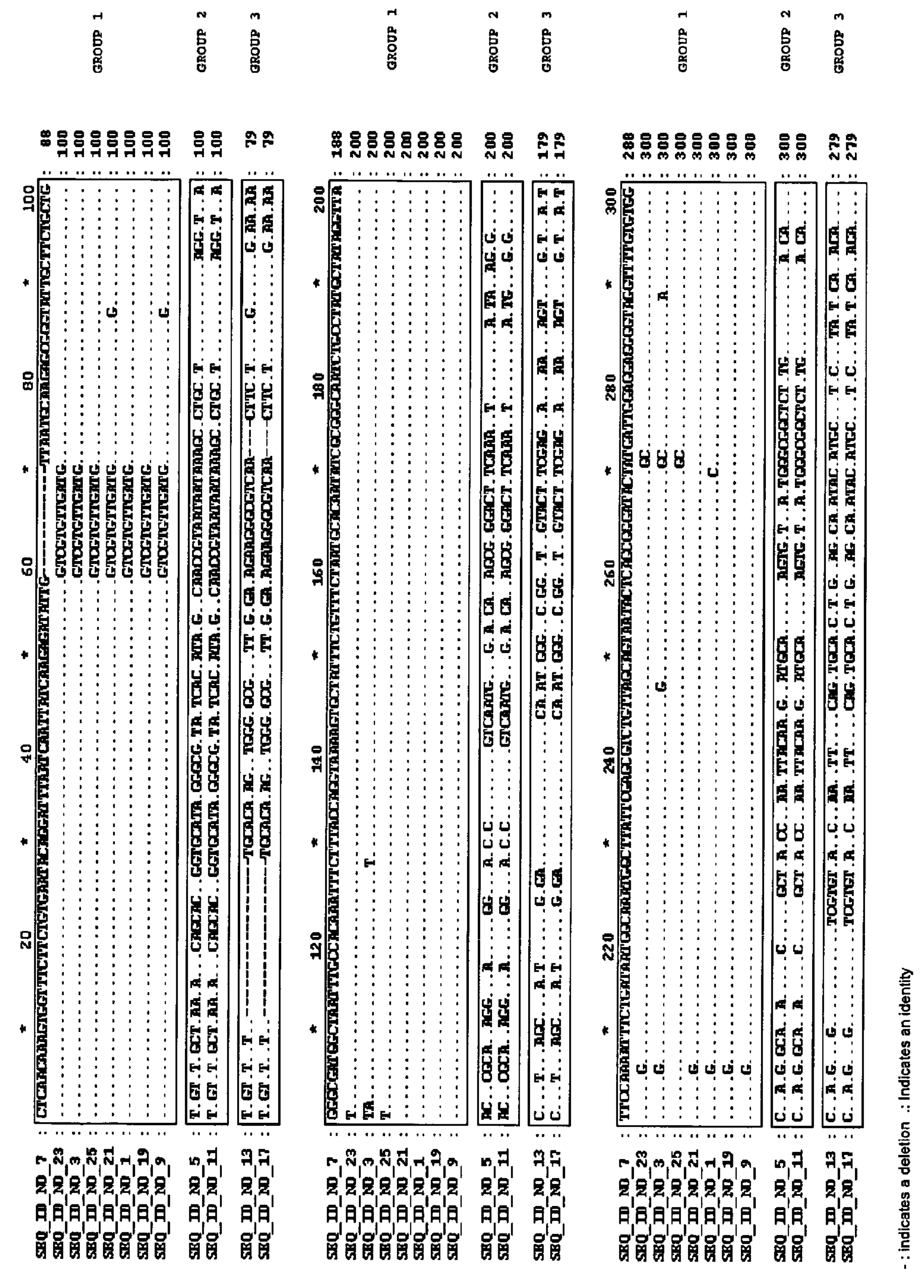
FIG. 2 shows the multiple alignment of the 3' terminal parts of the polynucleotides that code for the *H. parasuis* polypeptides. The polynucleotides can be grouped in three structural groups called group 1, group 2 and group 3. Group 1 comprises the nucleotides SEQ ID NO: 1, SEQ ID NO: 3, SEQ ID NO: 7, SEQ ID NO: 9, SEQ ID NO: 19, SEQ ID NO: 21, SEQ ID NO: 23 and SEQ ID NO: 25. Group 2 comprises the nucleotides SEQ ID NO: 5 and SEQ ID NO: 11. Group 3 comprises the nucleotides SEQ ID NO: 13 and SEQ ID NO: 17. The polynucleotide defined by the sequence SEQ ID NO: 15 is considered to belong to group 1, but it cannot be introduced in the multiple alignment of all the polynucleotides as it is lacking a fragment of the 3' terminal part. The multiple alignments are achieved by multiplying the CLUSTALX program described in Thompson et al., Nucleic Acids Res. 25: 4876 (1997).

As is shown in the multiple alignment of the terminal 3' parts of the *H. parasuis* polynucleotides of FIG. 2, the polynucleotides can be grouped in three structural groups called group 1, group 2 and group 3. Group 1 comprises the nucleotides SEQ ID NO: 1, SEQ ID NO: 3, SEQ ID NO: 7, SEQ ID NO: 9, SEQ ID NO: 19 SEQ ID NO: 21, SEQ ID NO: 23 and SEQ ID NO: 25. Group 2 comprises the nucleotides SEQ ID NO: 5 and SEQ ID NO: 11. Group 3 comprises the nucleotides SEQ ID NO: 13 and SEQ ID NO: 17. The polynucleotide SEQ ID NO: 15 cannot be formally classified in any group as it is missing at least one fragment of the terminal 3' part. Nevertheless, the last 198 nucleotides of SEQ ID NO: 15, have an identity comprising between 98% and 99% with the regions corresponding to all sequences of group 1, for which reason it is considered that SEQ ID NO: 15 belongs to group 1.

Procedure for the Preparation of the Polynucleotides of the Invention

From the multiple alignments of the 5' part of the polynucleotides SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25, which are shown in FIG. 3, an oligonucleotide is derived which hybridizes with the first 27 nucleotides after the start codon of the polypeptides.

Said oligonucleotide, which can also be called primer, has the following sequence:

```
pADH-F:
5'-ATGAATAAAATATTTAGAGTTATTTGG-3'  (SEQ ID NO: 27)
```

The oligonucleotides mentioned in this description have been produced from the company Eurogentec, which prepares them on a commercial scale from the sequence submitted to it.

In the same way, from the multiple alignment of the 3' end of the polynucleotides (FIG. 2), three oligonucleotides are derived, which hybridize with the last 24 or 25 nucleotides of the polypeptide genes ending in the codon of the last amino acid.

The sequences of these oligonucleotides (Eurogentec) are:

```
pADH-R1:
5'-CCACACAAAACCTACCCCTCCTCC-3'      (SEQ ID NO: 28)

pADH-R2:
5'-CCACTGATAACCTACCCCCACAGAG-3'     (SEQ ID NO: 29)

pADH-R3:
5'CCACTGTAATGCAATACCTGCACC-3'       (SEQ ID NO: 30)
```

The pADH-R1 oligonucleotide hybridizes with the polynucleotides of group 1 (SEQ ID NO: 1, SEQ ID NO: 3, SEQ ID NO: 7, SEQ ID NO: 9, SEQ ID NO: 19, SEQ ID NO: 21, SEQ ID NO: 23 and SEQ ID NO: 25). Likewise, oligonucleotide pADH-R2 hybridizes with the polynucleotides of group 2 (SEQ ID NO: 5 and SEQ ID NO: 11) and oligonucleotide pADH-R3 hybridizes with the polynucleotides of group 3 (SEQ ID NO: 13 and SEQ ID NO: 17).

The oligonucleotides described herein can be used as primers to amplify the polynucleotides of the invention in an *H. parasuis* strain (Nagasaki) using, for example, the AccuPrime™ Taq DNA Polymerase High Fidelity system (Invitrogen).

The result of the amplification is analysed by electrophoresis in 0.8% agarose gel stained with SybrGold (Molecular Probes).

Lane a of FIG. 5 shows the amplification products corresponding to the *H. parasuis* strain (Nagasaki).

Lane M of FIG. 5 shows a 1 kb ladder (New England Biolabs), which has been used as a marker of molecular weight.

The amplification products corresponding to the sequences SEQ ID NO: 1, SEQ ID NO: 3, SEQ ID NO: 7, SEQ ID NO: 9, SEQ ID NO: 19 SEQ ID NO: 21, SEQ ID NO: 23 and SEQ ID NO: 25 of group 1 (FIG. 5A, column a); SEQ ID NO: 5 and SEQ ID NO: 11 of group 2 (FIG. 5B, column a); SEQ ID NO: 13 and SEQ ID NO: 17 of group 3 (FIG. 5C, column a) indicated by the sign < and its corresponding number can be distinguished.

The polynucleotide SEQ ID NO: 15 is found in the area of the polynucleotides defined by the sequences SEQ ID NO: 3 and SEQ ID NO:23.

It can be verified that there is a good correlation between the size expressed in base pairs (pb) of the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 17, SEQ ID NO: 19, SEQ ID NO: 21, SEQ ID NO: 23 and SEQ ID NO: 25, and the apparent molecular weights of the amplification products indicated in the gel.

Each of the polynucleotide bands is extracted and can later be amplified following conventional techniques such as those mentioned previously in this description, so that amplification products are produced for each of the polynucleotides of the invention.

In the case of the polynucleotides that have similar molecular weights, and appear confused in the electrophoresis gel, they are later separated using electrophoresis performed in conditions which enable their separation, as is well known by the person skilled in the art, for example, increasing the length of the gel and/or the electrophoresis development time, or cloning in plasmid vectors.

Procedure to Determine if an *H. parasuis* Strain is Virulent or Avirulent

As has already been mentioned, one of the essential characteristics of *H. parasuis* is its antigenic variability, and when experimental infections are performed on animals, the degree of virulence is variable depending on the strain. Therefore, it is desirable to have a procedure to identify the *H. parasuis* strains which permits their classification as virulent or avirulent.

In one aspect of the invention, it has the object of the use of the polynucleotides of the invention to determine if an *H. parasuis* strain is virulent or avirulent.

It has been found that the virulent strains have genomic amplification products corresponding to one or several polynucleotides of the invention, whilst the avirulent strains do not have them.

The procedure to determine if a strain of *H. parasuis* is virulent or avirulent substantially follows the experimental protocol of genomic amplification of the polynucleotides described in the above section (Procedure for the preparation of the polynucleotides of the invention).

In this case, the DNA of a strain whose virulence genotype one wants to determine is tested, and it can also test the DNA of the *H. parasuis* strain (Nagasaki), which acts as control.

Said procedure uses the primer pADH-F, together with one of the primers pADH-R1, pADH-R2, and pADH-R3, already mentioned, to selectively amplify the polynucleotides of group 1, 2 and 3, respectively.

The amplification can be performed using, for example, the AccuPrime™ Taq DNA Polymerase High Fidelity system (Invitrogen).

The result is analysed by electrophoresis in 0.8% agarose gel stained with SybrGold (Molecular Probes).

FIG. 5 shows the amplification products corresponding to the *H. parasuis* strain (Nagasaki), lane a, and to several tested strains, which as will be seen in the Examples, corresponds to different serotypes:

- Lanes b-e show the amplification products corresponding to isolated strains of the nasal cavity in swine which have no symptoms or lesions characteristic of Glässer's disease and/or from farms with no history of the disease.
- Lanes f-k show the amplification products corresponding to isolated strains of different swine organs with confirmed Glässer's disease.

It can be observed that the avirulent strains show no amplification product corresponding to the polynucleotides of the invention, whilst the amplification products of the virulent strains have correspondence with one or several polynucleotides of the invention.

Therefore, it is verified that the use of the polynucleotides of the invention enables determining in a simple manner if an *H. parasuis* strain is virulent or avirulent, irrespective of the antigenic variability said microorganism has.

In another aspect of the invention, it has the object of a kit to determine if an *H. parasuis* strain is virulent or avirulent, characterized in that it comprises:

a) the amplification products of the polynucleotides with the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25, b) the oligonucleotide pADH-F (SEQ ID NO: 27), c) oligonucleotides pADH-R1 (SEQ ID NO: 28), pADH-R2 (SEQ ID NO: 29), and pADH-R3 (SEQ ID NO: 30), and d) the reagents necessary to perform the amplification reaction using the PCR technique.

The amplification products of the polynucleotides of the invention are used as templates beside the ladder of templates of molecular weight, e.g. the 1 kb ladder (New England Biolabs).

The oligonucleotides that are included in the kit are used to amplify the homologous polynucleotides of the invention possibly present in the test strains using the PCR technique well known by persons skilled in the art, and to determine if the strain is virulent or avirulent, following the method already described in this same section.

In a preferred embodiment, the kit may comprise the *H. parasuis* strain (Nagasaki) for it to serve as a control, as all the nucleotides of the invention are amplified therein.

Homology

The percentage of identity between two amino acid sequences in this invention designates the percentage of residues of identical amino acids between the two sequences that are compared, which is produced after achieving the best alignment, and the percentage being purely statistical, and the differences between the two sequences may be randomly distributed and throughout the sequence. The best alignment relates to the alignment for which the percentage of identity is the greater.

The comparison between two amino acid sequences can be made, for example, using the blastP computer program which is available on the website (http://www. at the site ncbi.nlm-.nih.gov/BLAST/) of the National Center for Biotechnology Information.

The percentage of identity between two amino acid sequences is calculated by firstly comparing the two sequences positioned according to the best alignment, and determining the number of identical positions for which the residue of amino acids is identical between the sequences.

The percentage of identity between the two sequences compared is calculated by dividing this number of identical positions by the total number of compared positions, and multiplying the result by 100.

A polypeptide which has a certain percentage of identity with another one, is typically designated as a homologous polypeptide.

The percentage of identity between sequences of nucleotides can be calculated in the same way as with the amino acid sequences.

The degree of identity between homologous polynucleotides can be determined experimentally, for example, using the sequencing of polynucleotides which are found in the lanes corresponding to the virulent strains of FIG. 5.

The electrophoresis of FIG. 5 shows that in addition to the polynucleotides of the invention, on amplifying the DNA of the virulent strains with the pADH-F, and pADH-R1, pADH-R2, or pADH-R3 primers, other polynucleotides are also amplified, whose molecular weights do not correspond with the molecular weights of the polynucleotides of the invention.

These polynucleotides which are also amplified with the primers designed for amplifying the polynucleotides of the invention are considered homologous polynucleotides.

Homologous polynucleotides have been extracted from the electrophoresis gel corresponding to the strains of lanes g, j, i and k belonging to groups 1 and 2, and polynucleotides corresponding to the strains of lanes f and h belonging to group 2, and their ends have been directly sequenced with the p-ADH-F and pADH-R1 or p-ADH-R2 primers, depending on whether they belong to group 1 or group 2.

Once the areas of highest quality have been selected, the sequences produced have been compared with the polynucleotides of the invention using the aforementioned blastX program. The sequences of the homologous polypeptides are compared in the same way, polypeptides which have been produced by the in silico translation of polynucleotide sequences.

In the terminal 3' part corresponding to the sequences performed with the pADH-R1 or p-ADH-R2 primers, homologies have been produced between 95% and 98%, and the pertaining of the homologs to the different groups is respected.

The sequences produced in the 5' terminal part have homologies that vary between 59% and 94%.

FIG. 6 shows the result of the comparison of the sequence of amino acids corresponding to the polypeptide called HP2269-2-j-1. Said polypeptide is coded for the PCR product belonging to the polynucleotide of lowest molecular weight of group 2 of the HP2269 strain which is in lane j (band indicated by an arrow in FIG. 5). The sequence of polynucleotides produced with the pADH-F primer (SEQ ID NO: 27) is translated in silico, and the resulting polypeptide sequence is compared with the polypeptide sequences of the invention using the blastX program.

FIG. 6A shows the alignment produced with the polypeptide SEQ ID NO: 16 belonging to group 1, and in FIG. 6B the alignment produced with the polypeptide SEQ ID NO: 12, belonging to group 2. In both cases the sequence of amino acids of the HP2269-2-j-1 polypeptide has 59% identity, and is the best homology with the polypeptides of the invention that it has been possible to find.

Therefore, an *H. parasuis* polynucleotide which expresses a polypeptide that has an identity of at least 60% with a polypeptide defined by a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26 also forms part of the invention.

Identity with the polypeptide amino acid sequences is preferably at least 70%, more preferably at least 80%, more preferably at least 90%, at least 95% being especially preferred.

The percentage of identity between sequences of nucleotides can also be determined by hybridization studies.

Preferably the polynucleotide of the invention has a sequence capable of hybridizing, in highly stringent conditions, a sequence selected from the group formed by the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

Hybridization in highly stringent conditions means that the conditions of temperature and ionic strength are selected so that it enables the hybridization to be maintained between two complementary DNA fragments. These conditions are well known by the person skilled in the art, and are described, for example, in the book by Sambrook, J., and Russell, R. W., Molecular cloning, a laboratory manual. Third Edition. CSHL press, Cold Spring Harbor, N.Y., 2001. For example, highly stringent conditions include, but are not limited to, washes with 0.1×SSC at 65° C., which achieves that only polynucleotides with at least 95% identity are hybridized.

Polypeptides

In another aspect, the present invention relates to an *H. parasuis* polypeptide which has identity of at least 60% with a polypeptide defined by a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

The percentage of identity between the amino acid sequences of the polypeptides is determined in the same way as previously explained.

Preferably, the homologous polypeptides have at least 70%, more preferably at least 80%, more preferably at least 90%, at least 95% being especially preferred, identity with the amino acid sequences of the polypeptides of the invention.

Preferably, the polypeptide has a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

As has already been mentioned, the polypeptide defined by the sequence SEQ ID NO: 2 is the in silico translation of the polynucleotide defined by the sequence SEQ ID NO: 1, and so on and so forth.

The common structural characteristics these polypeptides have make them candidates of being considered with a high probability as proteins of the adhesin, invasin, hemaglutinin or autotransporter type.

As is shown in the multiple alignment of the 3' ends of the *H. parasuis* polypeptides of FIG. 4, they can be grouped in three groups called group 1, group 2 and group 3.

Group 1 comprises the polypeptides SEQ ID NO: 2, SEQ ID NO: 4, SEQ ID NO: 8, SEQ ID NO: 10, SEQ ID NO: 20, SEQ ID NO: 22, SEQ ID NO: 24 and SEQ ID NO: 26. Group 2 comprises the polypeptides SEQ ID NO: 6 and SEQ ID NO: 12. Group 3 comprises the polypeptides SEQ ID NO: 14 and SEQ ID NO: 18. The polypeptide defined by the sequence SEQ ID NO: 16 cannot be formally classified in any of the groups, but equal to the polynucleotide from which it derives, defined by the sequence SEQ ID NO: 15, it is considered that it forms part of group 1.

Procedure for the Preparation of the Polypeptides of the Invention

Another aspect of the invention relates to a procedure for the preparation of the polypeptides of the invention by recombinant technology, which comprises the following stages:

a) culturing a host cell transformed with an expression vector which comprises a polynucleotide which expresses a polypeptide with an identity of at least 60% with a polypeptide defined by a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26, b) expressing said polynucleotide to produce said polypeptide.

Preferably in stage a) the polynucleotide has a sequence capable of hybridizing, in highly stringent conditions, a sequence selected from the group formed by the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

More preferably in stage a) the polynucleotide has sequence selected from the group formed by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

To perform said procedure, host cells transformed with expression vectors are selected which permit the expression of the *H. parasuis* polynucleotides of the invention in polypeptides.

Among the host cells that can be used to express the polynucleotides we find, for example, any strain of *E. coli*, yeasts and superior eukaryotic cells. Preferably, strains of *E. coli* with a high expression yield are used, for example, the *E. coli* BL21 (ED3) strain (Novagen).

In another aspect of the invention, it has the object of a host cell transformed with an expression vector which comprises at least one polynucleotide which expresses a polypeptide which has an identity of at least 60% with a polypeptide defined by a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

Preferably, the polynucleotide has a sequence capable of hybridizing, in highly stringent conditions, a sequence selected from the group formed by the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

More preferably, the polynucleotide has a sequence selected from the group formed by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

In another additional aspect of the invention, it has the object of an expression vector which comprises a polynucleotide which expresses a polypeptide which has an identity of at least 60% with a polypeptide defined by a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

Preferably, the polynucleotide has a sequence capable of hydbridizing in highly stringent conditions a sequence selected from the group formed by the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

More preferably, the polynucleotide has a sequence selected from the group formed by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

The expression vector is an entity which is used to introduce a polynucleotide in a cell. Normally, plasmids and phages are used.

In the state of the art numerous types of appropriate expression vectors are well known. Among them, we can mention, for example, the vectors of the series pET (Novagen) or those of series pQE (Qiagen).

When vectors of the pET series (Novagen) are used, they permit directionally cloning the genes that will be at 5' under the control of the T7lac promoter and a ribosome fixation sequence. In part 3' of the multiple cloning site of the pET-24a(+) and pET-24d(+) vectors, we find coding sequences for 6 histidines to facilitate the purification of the recombinant polypeptide.

The restriction enzymes Nde I and Nco I present in pET-24a(+) and pET-24d(+) respectively, generate cuts in part 5' of the multiple cloning site suitable for the insertion of genes which start with the ATG triplet of the translation start.

Typically, the gene is cloned in its part 3' as close as possible to the histidine tail, for which reason there exists the restriction site Xho I.

Generally, the inserts do not have sequences recognized by the restriction enzymes Nde I, Nco I and Xho I. If this happens, primers are designed which are capable of amplifying the 5' and 3' ends of the polypeptides, but which include the suitable restriction sites at the ends of these primers.

Other restriction enzymes may generate sticky ends compatible with those made by Nde I, Nco I or Xho I. This property is particularly interesting when the genes that have to be cloned have restriction sites Nde I, Nco I or Xho I, but not those of other enzymes with compatible ends. In that case, primers are designed with the restriction sites corresponding to the enzymes compatibles with Nde I, Nco I or Xho I.

The sequences of the primers that may be used are the following:

pADH-F-BspHI: (SEQ ID NO: 31)
5' GACTGATCATGAATAAAATATTTAGAGTTATTTGG 3' pADH-F-NdeI: (SEQ ID NO: 32)
5' GACTGACATATGAATAAAATATTTAGAGTTATTTGG 3' pAD H-R1-XhoI: (SEQ ID NO: 33)
5' TTACTCGAGCCACACAAAACCTACCCCTCCTCC 3' pADH-R2-Sall: (SEQ ID NO: 34)
5' TAGTTAGTCGACCCACTGATAACCTACCCCCACAGAG 3' pADH-R3-XhoI: (SEQ ID NO: 35)
5' TTACTCGAGCCACTGTAATGCAATACCTGCACC 3'

The recognition sequences of the restriction enzymes are underlined whilst the sequences coding for the polypeptides are in bold. The additional nucleotides in part 5' of the primers are random, but they are necessary for the good functioning of the restriction enzymes.

The techniques of recombinant technology used in the procedure to prepare the polypeptides of the invention are well known by the person skilled in the art, and are described, for example, in the book by Sambrook et al., op.cit.

Complementary information to perform said procedure are also provided by the companies that market the expression vectors, and may be found, for example, in the website: www.emdbiosciences.com.

By way of example, from among them we can mention:

1. Preparation of the vectors (plasmids pET-24a(+) (Novagen), and pET-24d(+) (Novagen)).
2. Preparation of the DNA inserts from the polynucleotides amplified by PCR.
3. Ligation of the inserts in the pET-24(+) and pET-24d(+) plasmids prepared with the T4 ligase (Quick Ligation Kit, New England Biolabs)
4. Transformation of the ligation products in *E. coli* Novablue (Novagen).
5. Characterization of the recombinant plasmids by sequencing, using the T7 promoter primers: 5'TAATACGACTCACTATAGG3' (SEQ ID NO: 38) and T7 terminator: 5'GCTAGTTATTGCTCAGCGG3' (SEQ ID NO: 39) which are found at the ends of the cloning site.
6. Transformation of the recombinant plasmids in *E. coli* BL21 (ED3) (Novagen).
7. Production and recovery of the *H. parasuis* recombinant polypeptides in *E. coli* BL21 (ED3).
8. Purification of the recombinant polypeptides from inclusion corpuscles with the His Bind Resin Ni-charged kit (Novagen).

The polypeptides of the invention are typically produced with a very high degree of purity.

In another aspect, the invention relates to the use of the polypeptides of the invention for the preparation of vaccines and/or immunogenic compositions for the prophylactic or therapeutic treatment of the infection caused by *H. parasuis* in an animal.

Vaccines

The vaccine against the infections caused by *H. parasuis*, object of the invention, comprises an immunologically effective quantity of a polypeptide which has an identity of at least 60% with a polypeptide which has a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, or SEQ ID NO: 26, and an auxiliary agent.

Identity with the amino acid sequences of the polypeptides is preferably at least 70%, more preferably at least 80%, more preferably at least 90%, at least 95% being especially preferred.

More preferably, the vaccine comprises an immunologically effective quantity of a polypeptide which has a sequence selected from the group formed by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

The vaccine may comprise several polypeptides of the invention with the purpose of increasing the immunological response.

In this description, vaccine or immunogenic composition is understood to be an antigen or compound which induces an immunological response in an animal.

Immunologically effective quantity is understood to be that quantity of antigen that is capable of inducing or contributing to generating a protective immunological response (total or partial) to infection by *H. parasuis*.

A protective immunological response can be manifested as any reduction in the rate of infection by the pathogen and/or any reduction in the symptoms or severity of the infection caused by the pathogen microorganism.

The vaccine can be administered prophylactically to an animal that has not been exposed to an antigen, so that subsequent infection by *H. parasuis* is prevented. Alternatively, the vaccine can be administered therapeutically to an animal that has been previously exposed or infected by *H. parasuis*. Although the infection cannot be avoided, the immunological response generated by animal organism allows the immunological system thereof to act more effectively against the infection, and, for example, the symptoms associated with the infection occur more lightly.

Vaccines that contain polypeptides are generally well known in the state of the art, for example, they are disclosed in patents EP-B-0074248, and EP-B-0155146.

Vaccines can also be developed that contain an immunologically effective quantity of the *H. parasuis* polynucleotides of the invention.

The vaccine of the invention can also be a combined vaccine in order to protect the animals against infection by *H. parasuis* and by one or more pathogens. The second component of the combined vaccine is selected based on its capacity to generate a protective response to a pathogen and/or its capacity of improving the symptoms or pathological condition of the animal.

These immunogenic compositions may contain, but are not limited, to those which also protect against infection by *H.*

*parasuis* also provide protection against *Actinobacillus pleuropneumoniae, Actinobacillus suis, Pasteurella multocida, Salmonella cholerasuis, Streptococcus suis, Erysipelothrix rhusiopathiae, Leptospira* sp., *Staphylococcus hyicus, Bordetella bronchiseptica, Mycoplasma hyopneumoniae, Lawsonia intracellularis, Escherichia coli*, PRRS, swine flu, porcine parvovirus, coronavirus and circovirus.

Optionally, the antigen that forms part of the second component of the vaccine may be covalently bound to the first component forming a chimeric molecule. The antigen of the second component may also be bound to a hapten.

Chimeric molecules that contain the first and second component of the combined vaccine can be synthesized using well-described techniques. For example, they can be synthetically produced using commercial peptide synthesizers and standard commercial processes (Merrifield, Science, 232:341-347 (1985)). Alternatively, the antigens can be separately synthesized and later be covalently bound by chemical cross-linking.

The vaccine may be administered by the appropriate route, such as, for example, oral, intranasal, intramuscular, intradermal, intraperitoneal, subcutaneous, rectal or vaginal route or by a combination of any of the aforementioned routes.

The pharmaceutical form of the vaccines object of the invention depends on the form of administration and may be, for example, in the form of injectables (solutions, suspensions, or emulsions), tablets, suppositories, capsules, prolonged release formulations or powders.

The quantity of antigen(s) included in the vaccine depends on different factors such as age, weight, health and the general physical characteristics of the animal that is going to be vaccinated, as well as the particular vaccine that is going to be administered. The determination of the optimum vaccine dose for each one of the components may be evaluated by routine techniques such as seroconversion analysis.

Typically, said vaccines contain between 10-95% by weight of the polypeptides object of the invention, and generally comprise auxiliary substances that are selected in accordance with the pharmaceutical form and the form of administration.

The auxiliary agents that accompany the polypeptides in the vaccines of the invention are selected from the pharmaceutically acceptable excipients described, for example, in the book by R. C. Rowe et al., Handbook of Pharmaceutical Excipients, Pharmaceutical Press, 4th Edition, London, 2003 (ISBN: 0-85369-472-9).

In the case of liquid formulations, the auxiliary agents may be, among others: wetting agents, emulsion agents, buffer solutions for pH control, water, saline solution, ethanol, preservative agents and/or oily vehicles.

In the case of vaccines in solid form, the formulations may include, among others: binding agents, lubricating agents, sweetening agents, fillers and/or disintegrating agents.

The vaccines object of the invention may also include adjuvant agents in order to increase the immunogenicity thereof, and with it, their efficacy.

As adjuvant agents, the following, for example, can be used: aluminium phosphate, aluminium sulphate, aluminium hydroxide, *Quillaja saponaria* extract (QS21), purified saponin (Quil A), immunostimulant complexes (ISCOMs), calcium phosphate, calcium hydroxide, zinc hydroxide, CARBOPOL, muramyl dipeptide and/or any combination thereof.

Furthermore, the vaccine may contain any immunomodulator agent such as, for example, cytokines.

The vaccine can also be formulated with controlled release systems of the antigen, for example, those in which the antigen is combined with biocompatible polymers such as polyacetic acid, poly(lactic-glycolic) acid, methylcellulose, hyaluronic acid or collagen. Alternatively, the antigen can be microencapsulated with the aim of improving its administration and/or increasing its efficacy.

In some cases it may be convenient to store the vaccine in lyophilized form which is reconstituted with a sterile diluent before its administration.

The vaccines of the invention are highly effective in swine, both when the vaccine is performed prophylactically, as in the case of a therapeutic vaccine when the animal already shows symptoms of infection by *H. parasuis*.

The following examples are given in order to provide the person skilled in the art with a sufficiently clear and complete explanation of the present invention, but they should not be considered as limitations in the essential aspects of the object thereof, as has been stated in the previous sections of this description.

EXAMPLES

Example 1

Preparation of the *H. parasuis* Polynucleotides of the Invention

Firstly, the *H. parasuis* (Nagasaki) DNA is isolated and purified using the conventional methods described in Sambrook and Russell, (Molecular cloning, a laboratory manual. Third Edition. CSHL press, Cold Spring Harbor, N.Y., 2001) or with genomic DNA purification kits such as those proposed by Qiagen or Macherey-Nagel.

To prepare the polynucleotides of the invention, genomic amplification PCR technology of the AccuPrime™ Tag DNA Polymerase High Fidelity system (Invitrogen) is used, following the indications suggested by the manufacturer.

Three 200 µl reaction tubes, adaptable to thermocyclers (Axygen) are used, which contain a dilution of *H. parasuis* (Nagasaki) DNA in MilliQ $H_2O$, and the oligonucleotides that are used to perform the amplification, and the reagents are always maintained in ice.

Each of the three reaction tubes includes the oligonucleotide pADH-F (SEQ ID NO: 27) (Eurogentec), and furthermore, each tube contains a specific oligonucleotide to amplify groups 1, 2 and 3 of polynucleotides.

To amplify group 1 of polynucleotides, oligonucleotide pADH-R1 (SEQ ID NO: 28) (Eurogentec) is used, for group 2, oligonucleotide pADH-R2 (SEQ ID NO: 29) (Eurogentec), and for group 3, oligonucleotide pADH-R3 (SEQ ID NO: 30) (Eurogentec).

The following volumes are introduced in each reaction tube:

| Component | Volume |
|---|---|
| 10x AccuPrime PCR buffer II | 5 µl |
| Oligonucleotide pADH-F (10 pmol/µl) | 4 µl |
| Oligonucleotide pADH-R1 or pADH-R2 or pADH-R3 (10 pmol/µl) | 2 µl |
| *H. parasuis* (Nagasaki) DNA (50 ng/µl) | 3 µl |
| AccuPrime ™ Taq DNA Polymerase High Fidelity (5 U/µl) | 0.2 µl |
| MilliQ $H_2O$ | 35.8 µl |

The amplification reaction is performed in an Applied Biosystems (Axygen) thermocycler programmed with the following parameters:

1 cycle of 2 min at 94° C., followed by 30 cycles of 30 sec at 94° C., 30 sec at 60° C. and 15 min at 68° C., and 1 final cycle of 15 min at 68° C.

Subsequently, 0.05 μl of AccuPrime™ Taq DNA Polymerase High Fidelity is added to the amplification products of the polynucleotides of group 1 and they were incubated for 1 h 30 min at 68° C.

The amplification products of the polynucleotides of groups 2 and 3 were incubated for 3 h at 37° C.

These treatments permitted eliminating accessory bands corresponding to incomplete amplification products using the fact that this polymerase has exonuclease activity.

The result is analysed by electrophoresis in 0.8% agarose gel stained with SybrGold (Molecular Probes), migrating 10 μl of the amplification reaction product.

The electrophoresis results are shown in FIG. 5. Lane M shows a 1 kb ladder (New England Biolabs), which is used as marker of molecular weight.

Lane a contains the polynucleotides of the invention which have been amplified using the *H. parasuis* strain (Nagasaki).

In lane a of FIG. 5A, we can distinguish the amplification products corresponding to the polynucleotides of group 1 defined by the sequences SEQ ID NO: 1, SEQ ID NO: 3, SEQ ID NO: 7, SEQ ID NO: 9, SEQ ID NO: 19 SEQ ID NO: 21, SEQ ID NO: 23 and SEQ ID NO: 25.

In lane a of FIG. 5B, we can distinguish the amplification products corresponding to the polynucleotides of group 2 defined by the sequences: SEQ ID NO: 5 and SEQ ID NO: 11.

In lane a of FIG. 5C, we can distinguish the amplification products corresponding to the polynucleotides of group 3 defined by the sequences: SEQ ID NO: 13 and SEQ ID NO: 17.

The polynucleotide SEQ ID NO: 15 is found in the area of polynucleotides defined by the sequences SEQ ID NO: 3 and SEQ ID NO: 23.

It can be verified that there is good correlation between the size expressed in base pairs (pb) of the sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 17, SEQ ID NO: 19, SEQ ID NO: 21, SEQ ID NO: 23 and SEQ ID NO: 25, and the apparent molecular weights of the amplification products indicated in the gel.

Each one of the polynucleotide bands is extracted and it can later be amplified using conventional techniques such as those previously mentioned in this description, so that amplification products are produced for each of the polynucleotides of the invention.

In the case of polynucleotides which have similar molecular weights, and appear confused in the electrophoresis gel, they are later separated using electrophoresis performed in conditions which enable their separation, as in well known by the person skilled in the art, for example, increasing the length of the gel and/or the electrophoresis development time, or cloning in plasmid vectors

Example 2

Classification of *H. parasuis* Strains

To classify *H. parasuis* strains as virulent and avirulent strains, the procedure described in Example 1 is used for the *H. parasuis* strain (Nagasaki) for each strain one wants to classify.

Table I shows the characteristics of the tested strains which belong to several different serotypes:

TABLE I

| Lane (1) | Strain | Organ | Lesions | Serotype |
|---|---|---|---|---|
| a | Nagasaki | brain | septicaemia | 5 |
| b | *SW114 (4) | nasal | No lesions | 3 |
| c | F9 (5) | nasal | Without clinical symptoms | UT (2) |
| d | *D74 (4) | ND (3) | ND (3) | 9 |
| e | HP-3123 (6) | nasal | *E. coli* enteritis | UT |
| f | HP-1205 (6) | pericardium | pericarditis and pleuritis | 11 |
| g | HP-1302 (6) | Brain | polyserositis | 1 |
| h | HP-1319 (6) | Brain | polyserositis | UT |
| i | HP-2163 (6) | joint | pneumonia and arthritis | UT |
| j | HP-2269 (6) | Joint | pneumonia and arthritis | UT |
| k | HP-33 (6) | lung | pneumonia | 1 |

(1) Electrophoresis lane of FIG. 5 in which the polynucleotides amplified for each strain are viewed.
(2) UT: untypable strain.
(3) ND: not documented.
(4) The strains identified with the sign * are avirulent reference strains, whose non-virulence has been experimentally tested using infections in swine.
(5) Strain isolated in the veterinary faculty of the Autonomous University of Barcelona.
(6) Strains isolated by the HIPRA laboratories. The HP-3123 strain has been isolated from a pig from a farm without a history of Glässer's disease.

The strains corresponding to lanes b-e correspond to strains isolated from the nasal cavity in swine which had no symptoms or lesions characteristics of Glässer's disease, and/or from farms without a history of the disease, for which reason they can be considered as avirulent strains.

The strains corresponding to lanes f-k correspond to strains isolated from different organs of swine with confirmed Glässer's disease, they are therefore virulent strains.

The result of the PCR analysis of the panel of virulent and avirulent strains is shown in FIG. 5.

It can be observed that the strains SW114 (b), F9 (c), D74 (d) and HP3123 (e), from swine which did not have any symptoms or lesions characteristic of Glässer's disease, did not show any amplification in the areas corresponding to the polynucleotides of the invention.

In contrast, all strains from swine organs with confirmed Glässer's disease have at least one amplification corresponding to the polynucleotides of the invention. As can be verified in FIG. 5, most of the virulent strains HP1205 (f), HP1302 (g), HP1319 (h), HP2163 (I), HP2269 (j) and HP33 (k), have several amplifications corresponding to the polynucleotides of the invention.

Therefore, the use of the polynucleotides of the invention permits classifying the *H. parasuis* strains as virulent or avirulent irrespective of the antigenic variability said microorganism has.

Example 3

Preparation of the *H. parasuis* Polypeptides of the Invention

1.—Vector Preparation

The pET-24a(+) plasmid (Novagen) is digested by adding the following components to a sterile 1.5 ml tube:

| | |
|---|---|
| pET-24a(+) (1 μg/μl) | 5 μl |
| BSA 10 X | 5 μl |
| 10 X buffer | 5 μl |
| Nde I (20 U/μl) | 1 μl |
| Xho I (20 U/μl) | 2.5 μl |
| $H_2O$ | 31.5 μl |

The pET-24d(+) plasmid is digested by adding the following components to a sterile 1.5 ml tube:

| | |
|---|---|
| pET-24d(+) (1 μg/μl) | 5 μl |
| BSA 10 X | 5 μl |
| 10 X buffer | 5 μl |
| Xho I (20 U/μl) | 2.5 μl |
| Nco I (10 U/μl) | 1 μl |
| $H_2O$ | 31.5 μl |

The reactions are carried out in a 37° C. bath for 2 hours. Then, the digested plasmids are purified by agarose gel following conventional techniques, as has been mentioned in this description.

In this way, a linear plasmid is produced which has two incompatible ends.

2.—Preparation of the Inserts 1 ng of the polynucleotides of the invention prepared according to Example 1 is individually amplified following the experimental procedure described in said example, using the following oligonucleotides:

pADH-F-BsHI: (SEQ ID NO: 31)
5' GACTGATCATGAATAAAATATTTAGAGTTATTTGG 3',

-continued pADH-F-NdeI: (SEQ ID NO: 32)
5' GACTGACATATGAATAAAATATTTAGAGTTATTTGG 3', pADH-R1-XhoI: (SEQ ID NO: 33)
5' TTACTCGAGCCACACAAAACCTACCCCTCCTCC 3', pADH-R2-SalI: (SEQ ID NO: 34)
5' TAGTTAGTCGACCCACTGATAACCTACCCCCACAGAG 3',
and pADH-R3-XhoI: (SEQ ID NO: 35)
5' TTACTCGAGCCACTGTAATGCAATACCTGCACC 3', The recognition sequences of the restriction enzymes are underlined whilst the sequences coding for the polypeptides are in bold. The additional nucleotides in part 5' of the primers are random, but they are necessary for the good functioning of the restriction enzymes.

The amplification follows the experimental procedure of Example 1, except that only 22 amplifications are performed, instead of 30.

T Table II indicates the presence or absence of the restriction sites Nde I, Nco I, Xho I, BspH I (compatible with Nco I) and Sal I (compatible with Xho I) in the polynucleotides of the invention, the pair of primers used to amplify these polynucleotides, and the vector in which they are cloned.

TABLE II

| SEQ ID NO: | Nde I | Nco I | BspHI | Xho I | Sal I | Primers | Vector |
|---|---|---|---|---|---|---|---|
| 1 | − | − | − | − | | pADH-F-NdeI/ pADH-R1-XhoI | pET-24a(+) Nde/Xho |
| 3 | − | − | − | − | | pADH-F-NdeI/ pADH-R1-XhoI | pET-24a(+) Nde/Xho |
| 5 | + | − | − | − | − | pADH-F-BspHI/ pADH-R2-SalI | pET-24d(+) Nco/Xho |
| 7 | − | − | − | − | | pADH-F-NdeI/ pADH-R1-XhoI | pET-24a(+) Nde/Xho |
| 9 | − | − | − | − | | pADH-F-NdeI/ pADH-R1-XhoI | pET-24a(+) Nde/Xho |
| 11 | + | − | − | + | − | pADH-F-BspHI/ pADH-R2-SalI | pET-24d(+) Nco/Xho |
| 13 | − | − | − | − | | pADH-F-NdeI/ pADH-R3-XhoI | pET-24a(+) Nde/Xho |
| 15 | − | − | − | − | | pADH-F-NdeI pADH-R1-XhoI | pET-24a(+) Nde/Xho |
| 17 | − | − | − | − | | pADH-F-NdeI/ pADH-R3-XhoI | pET-24a(+) Nde/Xho |
| 19 | − | − | + | − | | pADH-F-NdeI/ pADH-R1-XhoI | pET-24a(+) Nde/Xho |
| 21 | − | − | − | − | | pADH-F-NdeI/ pADH-R1-XhoI | pET-24a(+) Nde/Xho |
| 23 | − | − | − | − | | pADH-F-NdeI/ pADH-R1-XhoI | pET-24a(+) Nde/Xho |
| 25 | − | − | − | − | | pADH-F-NdeI/ pADH-R1-XhoI | pET-24a(+) Nde/Xho |

After the amplification, the products produced with the MinElute Reaction Cleanup kit (Qiagen) are purified following the manufacturer's indications, except the fact that the elution stage is made with 40 μl of elution buffer.

The digestion of the ends of the amplification products is performed in accordance with the group to which the polypeptides belong.

For the amplification products from SEQ ID NO: 1, 3, 7, 9, 13, 15, 17, 19, 21, 23 and 25, the following is added to a 1.5 ml sterile tube:

| | |
|---|---|
| Amplification product | 38 μl |
| 10 X buffer | 5 μl |
| Xho I (20 U/μl) | 1 μl |
| Nde I (20 U/μl) | 1 μl |
| BSA 10 X | 5 μl |

For the amplification products from SEQ ID NO: 5 and 11, the following is added to a 1.5 ml sterile tube:

| | |
|---|---|
| Amplification product | 38 μl |
| 10 X buffer | 5 μl |
| BspHI (10 U//μl) | 2 μl |
| Sal I (20 U//μl) | 2 μl |
| BSA 10 X | 5 μl |

The reactions are carried out at 37° C. in a bath for 2 hours. The purification of the doubly digested amplification products is performed in agarose gel following the product described in the MinElute Reaction Cleanup kit from Qiagen.

3.—Ligation of the Inserts in pET-24a(+) and pET-24d(+).

The ligation is carried out with T4 ligase (Quick Ligation Kit, New England Biolabs) following the manufacturer's indications. Previously, the plasmid concentrations and 50 ng/μl insert are adjusted with milliQ $H_2O$. The following are added to a 1.5 ml sterile tube:

| | |
|---|---|
| MilliQ $H_2O$ | 6.5 μl |
| Digested DNA (50 ng/μl) | 1.5 μl |
| pET-24a(+) or pET-24d(+) (50 ng/μl) | 1 μl |
| 2X buffer | 10 μl |
| T4 ligase (the manufacturer does not specify enzyme concentration). | 1 μl |

It is incubated at a temperature between 22° C. and 25° C. for 15 min.

4.—Transformation of the Ligation Products in Novablue *E. coli.*

It is not necessary to purify the ligation products to transform the competent *E. coli* Novablue (Novagen) bacteria. This strain of *E. coli* does not allow the expression of recombinant proteins and serves to expand the recombinant plasmid before transforming the appropriate strains.

To a 1.5 ml sterile tube previously cooled in ice, add 20 μl of competent cells and 1 μl of ligation product. After incubation of 5 min in ice, introduce the tube in a 42° C. bath for 30 s. Next, it is again incubated in ice for 2 min. After this thermal shock, add 80 μl of SOC medium (Novagen) and the transformed bacteria are incubated at 37° C. with stirring (250 rpm).

The selection and cloning of the recombinant bacteria is performed on LB-agar plates in the presence of kanamycin (30 μg/μl).

5.—Characterization of Recombinant Plasmids.

The recombinant clones are grown in 96-well plates with capacity of 2 ml/well, and the plasmid is purified with any of the following kits:

R.E.A.L Prep 96 BioRobot (Qiagen) and NucleoSpin 96 Flash (Macherey-Nagel) with a robot (BioRobot 3000, Qiagen), or NucleoSpin 96 Flash (Macherey-Nagel) if this process is manually performed.

500 nanograms of supercoiled plasmid are produced for each preparation.

Each insert is characterized by sequencing with the BigDye Terminator v3.1 (Applied Biosystems) terminator kit in 96-well plates (Applied Biosystems or Axygen) adaptable to thermocyclers and sequencers from the manufacturer Applied Biosystems.

The primers used flank the cloning sites of the plasmid and have the following sequences:

```
T7 promoter:      5'TAATACGACTCACTATAGG3'

T7 terminator:    5'GCTAGTTATTGCTCAGCGG3'
```

6.—Transformation of Recombinant Plasmids in *E. coli* BL21 (ED3).

The *E. coli* BL21 (ED3) strain (Novagen) is a strain especially designed for the expression of large quantities of recombinant proteins under the control of T7.

The transformation with the recombinant plasmids pET-24a(+) and pET-24d(+) is carried out by adding 20 μl of competent bacteria and 1 μl of ligation product in a sterile 1.5 ml tube after cooling in ice.

After incubation of 5 min in ice, introduce the tube in a 42° C. bath for 30 s. Next, it is again incubated in ice for 2 min. After this thermal shock, add 80 μl of SOC medium (Novagen) and the transformed bacteria are incubated at 37° C. with stirring (250 rpm).

The selection and cloning of the recombinant bacteria is performed on LB-agar plates in the presence of kanamycin (30 μg/μl).

7.—Production of Recombinant Polypeptides of *H. parasuis* in *E. coli* BL21 (ED3).

To produce each recombinant polypeptide, inoculate a colony in 50 ml of LB medium which has 30 μg/μl of kanamycin. The bacteria is grown at 37° C. in an orbital stirrer with ventilation until producing a value of 0.6 optical density at 600 nm.

IPTG is added at 1 mM in final concentration the incubation is continued at 37° C. for 3 h. Next, the bacteria are cooled in ice for 5 min and they are centrifuged at 5000 g for 5 min at 4° C. The bacterial precipitate is resuspended with 12.5 ml of cold 20 mM Tris-HCl pH 8, and they are recentrifuged in the same conditions.

The recombinant polypeptides are in the form of inclusion corpuscles in the bacteria cytoplasm, and they are recovered using the method recommended by Novagen of treatment by BugBuster Benzonase and rLysozyme products (pET system manual, www. at the site emdbiosciences.com/html/ NVG/ User-protocols.html) adding protease inhibitors (pefabloc, Roche Diagnostic).

The method consists of mild solubilization of the bacteria, digestion of the glycopeptide and the DNA, followed by a series of centrifugations intended to eliminate the impurities from the inclusion corpuscles.

The presence and relative quantity of recombinant polypeptides is observed by polyacrimide gel electrophoresis (Laemmli, Nature, 227:680-685, (1970)).

Typically, each recombinant polypeptide represents between 30 to 50% of the total transformed *E. coli* BL21-(ED3) transformed polypeptides and 90% of the polypeptides found in the inclusion corpuscles.

8.—Purification of the Recombinant Polypeptides from Inclusion Corpuscles.

The His Bind Resin Ni-charged kit is used in denatured conditions according to the method specified by the manufacturer (Novagen).

Firstly, the inclusion corpuscles are dissolved in a buffer containing 6M urea. This solution is applied to a column containing 2.5 ml of resin coupled to the $Ni^{2+}$ metal.

Polyhistidines have strong affinity with this metal ion and the recombinant polypeptides are absorbed in the column. After the corresponding washes, the recombinant protein is eluted with a buffer containing 6M urea and 1M imidazole.

The proteins are then renatured by dialysis using the Protein Refolding kit (Novagen) following the manufacturer's instructions.

Each one of the polypeptides of the invention with a degree of purity over 99%, which is appropriate so that they can be formulated in immunogenic compositions and/or vaccines against the infections caused by *H. parasuis.*

The invention claimed is:

1. An isolated polynucleotide consisting of a nucleotide sequence that encodes, or consisting of a nucleotide sequence which is entirely complementary to the entirety of a polynucleotide sequence that encodes, a polypeptide which has at least 80% amino acid sequence identity to the amino acid sequence of SEQ ID NO:2 or SEQ ID NO:4.

2. The isolated polynucleotide according to claim 1, wherein said polynucleotide is entirely complementary to the entirety of SEQ ID NO: 1.

3. The isolated polynucleotide according to claim 1, wherein said polynucleotide consists of the nucleotide sequence of SEQ ID NO: 1.

4. The isolated polynucleotide according to claim 1, wherein said polynucleotide has the polynucleotide sequence of SEQ ID NO: 3.

5. An expression vector which comprises a nucleotide sequence that encodes, or which comprises a nucleotide sequence which is entirely complementary to the entirety of a polynucleotide sequence that encodes, a polypeptide which has at least 80% amino acid sequence identity to the amino acid sequence of SEQ ID NO:2 or SEQ ID NO:4.

6. The vector according to claim 5, wherein said vector comprises a polynucleotide sequence entirely complementary to the polynucleotide sequence of SEQ ID NO: 1.

7. An expression vector comprising the polynucleotide sequence of SEQ ID NO: 1.

8. A host cell transformed with the expression vector of claim 5.

9. The host cell according to claim 8, wherein the expression vector comprises a polynucleotide sequence entirely complementary to the polynucleotide sequence of SEQ ID NO: 1.

10. A host cell transformed with an expression vector, wherein said expression vector comprises the polynucleotide sequence of SEQ ID NO: 1.

11. A process for the preparation of a polypeptide, comprising the following steps:

a) culturing a host cell transformed with an expression vector comprising a polynucleotide that encodes a polypeptide which has at least 80% amino acid sequence identity to the amino acid sequence of SEQ ID NO:2 or SEQ ID NO:4; and b) expressing said polynucleotide to produce said polypeptide.

12. A process for preparing a polypeptide, comprising:

culturing a host cell transformed with an expression vector, wherein said expression vector contains a polynucleotide comprising the polynucleotide sequence of SEQ ID NO: 1; and expressing said polynucleotide to produce said polypeptide.

13. A kit to determine if a strain of *H. parasuis* is virulent or avirulent, comprising:

a) an amplification product produced by polymerase-chain reaction (PCR) amplification of a polynucleotide comprising the polynucleotide sequence of SEQ ID NO: 1, wherein said PCR amplification is performed with a forward primer comprising the nucleotide sequence of SEQ ID NO: 27 and a reverse primer comprising the nucleotide sequence of SEQ ID NO: 28;

b) an oligonucleotide primer comprising the nucleotide sequence of SEQ ID NO: 27;

c) oligonucleotide primers comprising the nucleotide sequences of SEQ ID NO: 28, SEQ ID NO: 29 and SEQ ID NO: 30; and d) PCR reagents necessary to perform PCR amplification.

14. A method for determining the virulence of a strain of *H. parasuis*, comprising testing DNA from the strain to determine the presence or absence of the polynucleotide of claim 1, wherein the presence of the polynucleotide indicates the strain is virulent and the absence of the polynucleotide indicates the strain is avirulent.

* * * * *

SEQUENCE LISTING

```
<160> NUMBER OF SEQ ID NOS: 40

<210> SEQ ID NO 1
<211> LENGTH: 2859
<212> TYPE: DNA
<213> ORGANISM: Haemophilus parasuis

<400> SEQUENCE: 1

atgaataaaa tatttagagt tatttggagt catgctcaac aggcttgggt ggttgtgtct     60
gagttagtaa agtctcatac caaaacatcc gcttacacgg ataaaagagc tcaagtatgc    120
acctcagatt attttttaga taaacagcaa gataaattta aattaagtct tttaagtcta    180
gtattactaa gtatattttt tagtccagta gcagtaggtg cacaacttca cacaggaaca    240
gcatttcttc tagatggttc taataaatcg aagctaggaa ctgacgacgg tactattggt    300
attggtaaag atagtaaggc tgggtatggt gctattgcta tcggtcagta ttcaaaagct    360
aaagctaggc ataatgttgc gataggttat aaagcagatt caggagtaca accaaacact    420
attacgatag gctacaatac taaagtaagt gggcaggaag caattgccat cgggaaagag    480
tcaaaagcgg gaaaggaatc tgttgtctta ggcggacaag ccagtgcggc aaatattgaa    540
caagcagttg taataggtca ctctgctact gcaagtgcgt cacaatctat tgctatcggt    600
gcgagaagta agtctaccgc tgattacggt attgcggttg gtggtggtgc aactgctgga    660
aagaacgccg ttgctgttgg tagggactcg aaaggtgctg ggacagattc cattgcgata    720
ggtaattctg cgaaaaacaac aggggtagac tctgttgttg tgggtgccaa tatcaatgtg    780
acagatggac aattagtggc aattggacgc gaagcaaaag ctggaagcca ttctactgcc    840
ttgggttata aagcctctgc cggtggtatg cactctgttg ctgtgggtga aagtgccatg    900
acaaatgatg gtgctgctag agcaaccgca cttggtaata ataccgttgt caccgtgggc    960
ggcggtgtgg cattgggtta tgggtctaat gcaagtacag ctggcggtgt agtggggtta   1020
aaacaaaatc attctgtcac aacgggagaa agcactgtcg ataacggctt taaatctaca   1080
gaaagtgttg ataacaatcc taatcctatt cctattggtg cggtttctgt gggtaataac   1140
aacatcaaac gccaaatcgt caatgtggcg gcaggtaaag aattaaccga tgcggtaaac   1200
gtggcgcagc ttcaatcttt gacgatgaaa attagtggtg ataacagcag tagtggcaag   1260
gtaggcattt gggatggtac gctgaaagta gtgggtacaa gcggtcagat taagacttcc   1320
gcaaacggtg ataccatcac attgaaatta gatgaaacat tgaaaaacaa aattgataat   1380
attgacaatt taggttggaa acttgcaatt actaagggat cggggggtga agtaacgact   1440
cctaatactc catatcttat caaaatgagc gatatggcaa ccgtaacctt taccgctgga   1500
aataatatta aattagaaca agcggacgga aatattacga tttctacgat tggtaagtta   1560
```

-continued

```
attgcaaaga ctgaatggga aaatgatggt ttgaaaatta cttatacgga tggtatgcat   1620

gacattatca agaaaggtga aaaaggagat cgtggcgaaa aaggtccaaa aggcgataga   1680

ggagaaactg gctctgcggg tccagcgggt ccagcaggtg ctcaaggtcc agtaggtcct   1740

gcgggtccag caggtccaac tggaccacaa ggtgcaactg gtcctgcagg tccaaaagga   1800

gaggcaggag cagctggacc taagggtgag aaaggtgatc caggaccaaa aggcgaagct   1860

ggttcaacag gtccaacggg gcctgctggt ccaaaaggcg atccaggaca agcgggtcca   1920

aaaggagata caggtcagaa aggtgaaact ggtcctgcgg gtccagcggg accacaaggt   1980

cctgcgggtc cagcaggggc taagggtgac aaaggtgata cgggtccagc aggaccacga   2040

ggccctgcgg gtccaacggg accacaaggc cctgcgggtc cagcgggacc acaagaccct   2100

gcgggtccaa ctggaaattc ggaattaaaa ggcattacct cgattgccaa tggtaacgac   2160

gccaccaagg cgaatggggc taagattacc ttgtctgcag gttctacaga taaaacagtt   2220

aatgttaatg atgcgaaaat taccaatgtg gcggctggta cagcagatac tgatgcggta   2280

aatgtgagcc agttaaatac taaggcagca gcttcaaaaa cagaggttga agcgggtaaa   2340

aatgtgaaag tgacttcaaa aacgggtgca aatggtcaga atatttacaa tgtgagcgtg   2400

tctggagatt taagcgacat tacttcaatt agtaatggcg atacgaaagt atctttaggt   2460

aaagataagc aaggaaatcc agttgtaaat atgaatggcg ccagaattac caacgttgga   2520

gatggtagtg ctgagggcga tattgtgaat gttcgtcagc tcaacaaagt ggtttcttct   2580

gtgaatacag gatttaatca attatcaaga gatattggtc gtgttgatgt taatgcaaga   2640

gcgggtattg cttctgctgg ggcgatggct aatttgccac aaatttcttt accaggtaaa   2700

agtgctattt ctgtttctaa tgcacaatat cgcgggcaat ctgcctatgc tataggttat   2760

tccagaattt ctgataatgg caaatggctt attcgagcgt ctgttagcag taatactcag   2820

cgggatacca tgattggagg aggggtaggt tttgtgtgg                         2859
```

<210> SEQ ID NO 2
<211> LENGTH: 953
<212> TYPE: PRT
<213> ORGANISM: haemophilus parasuis

<400> SEQUENCE: 2

```
Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Ser
    50                  55                  60

Ile Phe Phe Ser Pro Val Ala Val Gly Ala Gln Leu His Thr Gly Thr
65                  70                  75                  80

Ala Phe Leu Leu Asp Gly Ser Asn Lys Ser Lys Leu Gly Thr Asp Asp
                85                  90                  95

Gly Thr Ile Gly Ile Gly Lys Asp Ser Lys Ala Gly Tyr Gly Ala Ile
            100                 105                 110

Ala Ile Gly Gln Tyr Ser Lys Ala Lys Ala Arg His Asn Val Ala Ile
        115                 120                 125

Gly Tyr Lys Ala Asp Ser Gly Val Gln Pro Asn Thr Ile Thr Ile Gly
    130                 135                 140

Tyr Asn Thr Lys Val Ser Gly Gln Glu Ala Ile Ala Ile Gly Lys Glu
```

```
145                 150                 155                 160

Ser Lys Ala Gly Lys Glu Ser Val Val Leu Gly Gly Gln Ala Ser Ala
                165                 170                 175

Ala Asn Ile Glu Gln Ala Val Val Ile Gly His Ser Ala Thr Ala Ser
            180                 185                 190

Ala Ser Gln Ser Ile Ala Ile Gly Ala Arg Ser Lys Ser Thr Ala Asp
        195                 200                 205

Tyr Gly Ile Ala Val Gly Gly Gly Ala Thr Ala Gly Lys Asn Ala Val
    210                 215                 220

Ala Val Gly Arg Asp Ser Lys Gly Ala Gly Thr Asp Ser Ile Ala Ile
225                 230                 235                 240

Gly Asn Ser Ala Lys Thr Thr Gly Val Asp Ser Val Val Val Gly Ala
                245                 250                 255

Asn Ile Asn Val Thr Asp Gly Gln Leu Val Ala Ile Gly Arg Glu Ala
            260                 265                 270

Lys Ala Gly Ser His Ser Thr Ala Leu Gly Tyr Lys Ala Ser Ala Gly
        275                 280                 285

Gly Met His Ser Val Ala Val Gly Glu Ser Ala Met Thr Asn Asp Gly
    290                 295                 300

Ala Ala Arg Ala Thr Ala Leu Gly Asn Asn Thr Val Val Thr Val Gly
305                 310                 315                 320

Gly Gly Val Ala Leu Gly Tyr Gly Ser Asn Ala Ser Thr Ala Gly Gly
                325                 330                 335

Val Val Gly Leu Lys Gln Asn His Ser Val Thr Thr Gly Glu Ser Thr
            340                 345                 350

Val Asp Asn Gly Phe Lys Ser Thr Glu Ser Val Asp Asn Asn Pro Asn
        355                 360                 365

Pro Ile Pro Ile Gly Ala Val Ser Val Gly Asn Asn Asn Ile Lys Arg
    370                 375                 380

Gln Ile Val Asn Val Ala Ala Gly Lys Glu Leu Thr Asp Ala Val Asn
385                 390                 395                 400

Val Ala Gln Leu Gln Ser Leu Thr Met Lys Ile Ser Gly Asp Asn Ser
                405                 410                 415

Ser Ser Gly Lys Val Gly Ile Trp Asp Gly Thr Leu Lys Val Val Gly
            420                 425                 430

Thr Ser Gly Gln Ile Lys Thr Ser Ala Asn Gly Asp Thr Ile Thr Leu
        435                 440                 445

Lys Leu Asp Glu Thr Leu Lys Asn Lys Ile Asp Asn Ile Asp Asn Leu
    450                 455                 460

Gly Trp Lys Leu Ala Ile Thr Lys Gly Ser Gly Gly Glu Val Thr Thr
465                 470                 475                 480

Pro Asn Thr Pro Tyr Leu Ile Lys Met Ser Asp Met Ala Thr Val Thr
                485                 490                 495

Phe Thr Ala Gly Asn Asn Ile Lys Leu Glu Gln Ala Asp Gly Asn Ile
            500                 505                 510

Thr Ile Ser Thr Ile Gly Lys Leu Ile Ala Lys Thr Glu Trp Glu Asn
        515                 520                 525

Asp Gly Leu Lys Ile Thr Tyr Thr Asp Gly Met His Asp Ile Ile Lys
    530                 535                 540

Lys Gly Glu Lys Gly Asp Arg Gly Glu Lys Gly Pro Lys Gly Asp Arg
545                 550                 555                 560

Gly Glu Thr Gly Ser Ala Gly Pro Ala Gly Pro Ala Gly Ala Gln Gly
                565                 570                 575
```

-continued

```
Pro Val Gly Pro Ala Gly Pro Ala Gly Pro Thr Gly Pro Gln Gly Ala
            580                 585                 590

Thr Gly Pro Ala Gly Pro Lys Gly Glu Ala Gly Ala Ala Gly Pro Lys
        595                 600                 605

Gly Glu Lys Gly Asp Pro Gly Pro Lys Gly Glu Ala Gly Ser Thr Gly
    610                 615                 620

Pro Thr Gly Pro Ala Gly Pro Lys Gly Asp Pro Gly Gln Ala Gly Pro
625                 630                 635                 640

Lys Gly Asp Thr Gly Gln Lys Gly Glu Thr Gly Pro Ala Gly Pro Ala
                645                 650                 655

Gly Pro Gln Gly Pro Ala Gly Pro Ala Gly Ala Lys Gly Asp Lys Gly
            660                 665                 670

Asp Thr Gly Pro Ala Gly Pro Arg Gly Pro Ala Gly Pro Thr Gly Pro
        675                 680                 685

Gln Gly Pro Ala Gly Pro Ala Gly Pro Gln Asp Pro Ala Gly Pro Thr
    690                 695                 700

Gly Asn Ser Glu Leu Lys Gly Ile Thr Ser Ile Ala Asn Gly Asn Asp
705                 710                 715                 720

Ala Thr Lys Ala Asn Gly Ala Lys Ile Thr Leu Ser Ala Gly Ser Thr
                725                 730                 735

Asp Lys Thr Val Asn Val Asn Asp Ala Lys Ile Thr Asn Val Ala Ala
            740                 745                 750

Gly Thr Ala Asp Thr Asp Ala Val Asn Val Ser Gln Leu Asn Thr Lys
        755                 760                 765

Ala Ala Ala Ser Lys Thr Glu Val Glu Ala Gly Lys Asn Val Lys Val
    770                 775                 780

Thr Ser Lys Thr Gly Ala Asn Gly Gln Asn Ile Tyr Asn Val Ser Val
785                 790                 795                 800

Ser Gly Asp Leu Ser Asp Ile Thr Ser Ile Ser Asn Gly Asp Thr Lys
                805                 810                 815

Val Ser Leu Gly Lys Asp Lys Gln Gly Asn Pro Val Val Asn Met Asn
            820                 825                 830

Gly Ala Arg Ile Thr Asn Val Gly Asp Gly Ser Ala Glu Gly Asp Ile
        835                 840                 845

Val Asn Val Arg Gln Leu Asn Lys Val Val Ser Ser Val Asn Thr Gly
    850                 855                 860

Phe Asn Gln Leu Ser Arg Asp Ile Gly Arg Val Asp Val Asn Ala Arg
865                 870                 875                 880

Ala Gly Ile Ala Ser Ala Gly Ala Met Ala Asn Leu Pro Gln Ile Ser
                885                 890                 895

Leu Pro Gly Lys Ser Ala Ile Ser Val Ser Asn Ala Gln Tyr Arg Gly
            900                 905                 910

Gln Ser Ala Tyr Ala Ile Gly Tyr Ser Arg Ile Ser Asp Asn Gly Lys
        915                 920                 925

Trp Leu Ile Arg Ala Ser Val Ser Ser Asn Thr Gln Arg Asp Thr Met
    930                 935                 940

Ile Gly Gly Gly Val Gly Phe Val Trp
945                 950
```

<210> SEQ ID NO 3
<211> LENGTH: 3675
<212> TYPE: DNA
<213> ORGANISM: Haemophilus parasuis

<400> SEQUENCE: 3

-continued

```
atgaataaaa tatttagagt tatttggagt catgctcaac aggcttgggt ggttgtatct     60
gagttagtaa agtctcatac caaaacatcc acttacacgg ataaaagagc tcaagtatgc    120
acctcagatt attttttaga taaacagcaa gataaattta aattaagtct tttaagtcta    180
gtattactag gtatattttt tagtccagta ggtttagctg catattttca agatagttct    240
ggacccggaa ggaaggaaga ggctgacgag ggtactattg gtattggtaa agatagtaac    300
gttgggcctg gttctattgc catcggtcgg tacgcaaaag ctgaaggtag gactagtatt    360
gcgataggtt atcaagctga agcagtcctt ttcgaaccca atgccgtagt cgttggggca    420
actgcagaag cattcggtta ttctgcggct tatggttatg gagcacaagc acgagcaata    480
ggctctgttg cagtcggtga aaatgctatt gcaaatcaaa atagaggcac tgcattgggt    540
aacaattcat ctgttaacgt tatcggtggt gttgcattgg gttatttatc tagagcagat    600
acgaaagggg gtattgaagg agcaaaacaa actttttctg tgacagaagg agaaaacact    660
gttgagaatg gatttaaatc cacagaaagt gctaataata atcggattgg tgcggtttct    720
gttggtagca atacttttag aaaggatggt agtagcataa tcaaacgcca aatcgtcaac    780
gttgcggcag gtaaagaatt aaccgatgca gtaaacgtgg cacagcttca atcgctcacc    840
atgcaaatag gaggcgataa cggcagcagt ggcaaggtag gcatttggag tggtatgctc    900
actgtaaaag gacaaaatgg tattacttcc gatgttaatg gcagtacgat tacggttaaa    960
ttagataaag aactcaaaga taaaattgat aagattgccg ctatgggtaa gttaattcaa   1020
agtacgaaaa atgaactaaa tggcgatcta acaattacct atacagatgg ttcgcatgac   1080
actatcaaga aaggtgaaaa aggagatcgt ggtgaaaaag gagaacgtgg cgaaactggc   1140
cctgcgggtc cagcaggtcc taggggtgaa ccgggtccta aaggtgagca aggcccagca   1200
ggtccgattg gtccagtggg tccagcaggg gctgctggag caacaggacc acaaggacct   1260
acgggtccag tggggccaat tggaccacaa ggtgtacctg gtcctaaggg ggataaaggc   1320
gaacaaggtc taagaggtga acaaggccct gcgggtgagc gaggagaaac aggccctgca   1380
ggtgcagctg gacctaaggg tgaacagggt cctgaaggta aacaaggtat tcaaggacct   1440
acgggtccag caggaccacg aggacctgcg ggtccagtcg gtgctcaagg tccgatgggt   1500
ccagcaggcc cagcgggtgc tcagggcata caaggtccaa aaggagatag aggtccaaaa   1560
ggtgatacag gtgagagagg tgcaactggc cctgcgggtc cagtaggtcc agctggccct   1620
gtgggtccag tcggtgctca aggtccagca ggtcctagag gcgaagcagg tcctgctgga   1680
gcaacaggac cacaaggtgc aacaggtcca gcgggagagc caggcaagca gggtcctagg   1740
ggggaacaag gtgcacctgg tcctgcaggt ccaaaaggag aggcaggagc aaaaggcgat   1800
aagggtgacc ctggtgaagc gggaccagtc ggccctcaag gtcctgtggg tgcaactggc   1860
cctgtgggtc cggcaggccc agcgggagag cgaggcgagc agggtcctag gggagataaa   1920
ggtgataccg gtcagaaagg tgaagctggc cctgcgggtg agcgaggaga aataggccca   1980
gcgggtccag cgggaccacg aggacctgag ggtccagcag gggctaaggg cgaacagggt   2040
cctaggggag ataaaggtga aactggtcct gtgggtccaa aaggagaggc aggagcaaaa   2100
ggcgataggg gcgaaactgg ccctgcgggt ccagcggggc caattggacc acaaggtgca   2160
cctggtcctg caggtccaaa aggagaggca ggagcaaaag gcgataaggg tgacactggt   2220
gaagcaggac caatgggccc tcaaggtcct gcgggtgcag ctggtccagc aggcccagcg   2280
ggagagcgag gcgagcaggg tcctagggga gataaaggtg aaactggtcc tgcgggtcca   2340
gcaggggcta agggtgaacc aggtcctaga ggtgaacaag gtattcaagg acctgcgggt   2400
```

-continued

```
ccaacgggac cacaaggacc gcagggaaca gcgggtattc agggacctaa gggtgaccga   2460

ggagaaactg gccctgcggg tgcagctggc cctgtgggtc cagcagggcc taggggtgaa   2520

cagggtccta aaggtgaaca aggtattcaa ggacctacgg gtccaacggg accacaagga   2580

ccgcagggaa cagcgggtat tcagggacct aagggtgagc gaggaaatgt gagtgtcagc   2640

ggtttaccga tggagtatac aacggaagac ggcaaatcaa ttatcaatat gggcggtaat   2700

ttctatttgg aagaacctgc taaagatggt tcgattaagt taattccagt ggtgaatgtt   2760

aaaggtaaat tctcaaccaa aacgcaaaat ccagatggca gtattacgct taagtcatta   2820

gcagtaaaag tgaatttggc aaatgaaact ccgatggtat taggtaatgt cgctgaaggg   2880

gtagcagata cggacgctgt taatgtgaaa cagttgaaat ctgcgaaaac tgaagtggaa   2940

tctaccgatc acagtgtggt gataaaagag cgtcagggcg ataatcagca aatcgtgtat   3000

gatttggcgg ttgctaaaac gaaactcact gcctctaagg ataaacgcac cattagtgca   3060

gcagataaaa gcaaccattt tgcgacagga gatgaagtcg cagtagcaat taataccgca   3120

accgcagccg caagaactga agttgaagcg ggtaaaaatg tgaaagtgac ttcaaaaacg   3180

ggtgcaaatg gtcagaatat ttacaatgtg agcgtgtctg gagatttaag cgacattact   3240

tcaattagta atggcgatac gaaagtatct ttaggtaaag ataagcaagg aaatccagtt   3300

gtaaatatga atggcgccag aattaccaac gttggagatg gtagtgctga gggcgatatt   3360

gtgaatgttc gtcagctcaa caaagtggtt tcttctgtga atacaggatt taatcaatta   3420

tcaagagata ttggtcgtgt tgatgttaat gcaagagcgg gtattgcttc tgctgtagcg   3480

atggctaatt tgccacaaat ttttttacca ggtaaaagtg ctatttctgt ttctaatgca   3540

caatatcgcg ggcaatctgc ctatgctata ggttattcca gaatttctga taatggcaaa   3600

tggcttattc gagcgtctgt tggcagtaat actcagcggg atactgcgat tggaggaggg   3660

gtaagttttg tgtgg                                                   3675
```

```
<210> SEQ ID NO 4
<211> LENGTH: 1225
<212> TYPE: PRT
<213> ORGANISM: haemophilus parasuis

<400> SEQUENCE: 4

Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Thr Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Gly
    50                  55                  60

Ile Phe Phe Ser Pro Val Gly Leu Ala Ala Tyr Phe Gln Asp Ser Ser
65                  70                  75                  80

Gly Pro Gly Arg Lys Glu Glu Ala Asp Glu Gly Thr Ile Gly Ile Gly
                85                  90                  95

Lys Asp Ser Asn Val Gly Pro Gly Ser Ile Ala Ile Gly Arg Tyr Ala
            100                 105                 110

Lys Ala Glu Gly Arg Thr Ser Ile Ala Ile Gly Tyr Gln Ala Glu Ala
        115                 120                 125

Val Leu Phe Glu Pro Asn Ala Val Val Val Gly Ala Thr Ala Glu Ala
    130                 135                 140

Phe Gly Tyr Ser Ala Ala Tyr Gly Tyr Gly Ala Gln Ala Arg Ala Ile
```

-continued

```
145                 150                 155                 160

Gly Ser Val Ala Val Gly Glu Asn Ala Ile Ala Asn Gln Asn Arg Gly
                165                 170                 175

Thr Ala Leu Gly Asn Asn Ser Ser Val Asn Val Ile Gly Gly Val Ala
            180                 185                 190

Leu Gly Tyr Leu Ser Arg Ala Asp Thr Lys Gly Gly Ile Glu Gly Ala
        195                 200                 205

Lys Gln Thr Phe Ser Val Thr Glu Gly Glu Asn Thr Val Glu Asn Gly
    210                 215                 220

Phe Lys Ser Thr Glu Ser Ala Asn Asn Asn Arg Ile Gly Ala Val Ser
225                 230                 235                 240

Val Gly Ser Asn Thr Phe Arg Lys Asp Gly Ser Ser Ile Ile Lys Arg
                245                 250                 255

Gln Ile Val Asn Val Ala Ala Gly Lys Glu Leu Thr Asp Ala Val Asn
            260                 265                 270

Val Ala Gln Leu Gln Ser Leu Thr Met Gln Ile Gly Gly Asp Asn Gly
        275                 280                 285

Ser Ser Gly Lys Val Gly Ile Trp Ser Gly Met Leu Thr Val Lys Gly
    290                 295                 300

Gln Asn Gly Ile Thr Ser Asp Val Asn Gly Ser Thr Ile Thr Val Lys
305                 310                 315                 320

Leu Asp Lys Glu Leu Lys Asp Lys Ile Asp Lys Ile Ala Ala Met Gly
                325                 330                 335

Lys Leu Ile Gln Ser Thr Lys Asn Glu Leu Asn Gly Asp Leu Thr Ile
            340                 345                 350

Thr Tyr Thr Asp Gly Ser His Asp Thr Ile Lys Lys Gly Glu Lys Gly
        355                 360                 365

Asp Arg Gly Glu Lys Gly Glu Arg Gly Glu Thr Gly Pro Ala Gly Pro
    370                 375                 380

Ala Gly Pro Arg Gly Glu Pro Gly Pro Lys Gly Glu Gln Gly Pro Ala
385                 390                 395                 400

Gly Pro Ile Gly Pro Val Gly Pro Ala Gly Ala Ala Gly Ala Thr Gly
                405                 410                 415

Pro Gln Gly Pro Thr Gly Pro Val Gly Pro Ile Gly Pro Gln Gly Val
            420                 425                 430

Pro Gly Pro Lys Gly Asp Lys Gly Glu Gln Gly Leu Arg Gly Glu Gln
        435                 440                 445

Gly Pro Ala Gly Glu Arg Gly Glu Thr Gly Pro Ala Gly Ala Ala Gly
    450                 455                 460

Pro Lys Gly Glu Gln Gly Pro Glu Gly Lys Gln Gly Ile Gln Gly Pro
465                 470                 475                 480

Thr Gly Pro Ala Gly Pro Arg Gly Pro Ala Gly Pro Val Gly Ala Gln
                485                 490                 495

Gly Pro Met Gly Pro Ala Gly Pro Ala Gly Ala Gln Gly Ile Gln Gly
            500                 505                 510

Pro Lys Gly Asp Arg Gly Pro Lys Gly Asp Thr Gly Glu Arg Gly Ala
        515                 520                 525

Thr Gly Pro Ala Gly Pro Val Gly Pro Ala Gly Pro Val Gly Pro Val
    530                 535                 540

Gly Ala Gln Gly Pro Ala Gly Pro Arg Gly Glu Ala Gly Pro Ala Gly
545                 550                 555                 560

Ala Thr Gly Pro Gln Gly Ala Thr Gly Pro Ala Gly Glu Pro Gly Lys
                565                 570                 575
```

-continued

```
Gln Gly Pro Arg Gly Glu Gln Gly Ala Pro Gly Pro Ala Gly Pro Lys
            580                 585                 590

Gly Glu Ala Gly Ala Lys Gly Asp Lys Gly Asp Pro Gly Glu Ala Gly
        595                 600                 605

Pro Val Gly Pro Gln Gly Pro Val Gly Ala Thr Gly Pro Val Gly Pro
    610                 615                 620

Ala Gly Pro Ala Gly Glu Arg Gly Glu Gln Gly Pro Arg Gly Asp Lys
625                 630                 635                 640

Gly Asp Thr Gly Gln Lys Gly Glu Ala Gly Pro Ala Gly Glu Arg Gly
                645                 650                 655

Glu Ile Gly Pro Ala Gly Pro Ala Gly Pro Arg Gly Pro Glu Gly Pro
            660                 665                 670

Ala Gly Ala Lys Gly Glu Gln Gly Pro Arg Gly Asp Lys Gly Glu Thr
        675                 680                 685

Gly Pro Val Gly Pro Lys Gly Glu Ala Gly Ala Lys Gly Asp Arg Gly
    690                 695                 700

Glu Thr Gly Pro Ala Gly Pro Ala Gly Pro Ile Gly Pro Gln Gly Ala
705                 710                 715                 720

Pro Gly Pro Ala Gly Pro Lys Gly Glu Ala Gly Ala Lys Gly Asp Lys
                725                 730                 735

Gly Asp Thr Gly Glu Ala Gly Pro Met Gly Pro Gln Gly Pro Ala Gly
            740                 745                 750

Ala Ala Gly Pro Ala Gly Pro Ala Gly Glu Arg Gly Glu Gln Gly Pro
        755                 760                 765

Arg Gly Asp Lys Gly Glu Thr Gly Pro Ala Gly Pro Ala Gly Ala Lys
    770                 775                 780

Gly Glu Pro Gly Pro Arg Gly Glu Gln Gly Ile Gln Gly Pro Ala Gly
785                 790                 795                 800

Pro Thr Gly Pro Gln Gly Pro Gln Gly Thr Ala Gly Ile Gln Gly Pro
                805                 810                 815

Lys Gly Asp Arg Gly Glu Thr Gly Pro Ala Gly Ala Ala Gly Pro Val
            820                 825                 830

Gly Pro Ala Gly Pro Arg Gly Glu Gln Gly Pro Lys Gly Glu Gln Gly
        835                 840                 845

Ile Gln Gly Pro Thr Gly Pro Thr Gly Pro Gln Gly Pro Gln Gly Thr
    850                 855                 860

Ala Gly Ile Gln Gly Pro Lys Gly Glu Arg Gly Asn Val Ser Val Ser
865                 870                 875                 880

Gly Leu Pro Met Glu Tyr Thr Thr Glu Asp Gly Lys Ser Ile Ile Asn
                885                 890                 895

Met Gly Gly Asn Phe Tyr Leu Glu Glu Pro Ala Lys Asp Gly Ser Ile
            900                 905                 910

Lys Leu Ile Pro Val Val Asn Val Lys Gly Lys Phe Ser Thr Lys Thr
        915                 920                 925

Gln Asn Pro Asp Gly Ser Ile Thr Leu Lys Ser Leu Ala Val Lys Val
    930                 935                 940

Asn Leu Ala Asn Glu Thr Pro Met Val Leu Gly Asn Val Ala Glu Gly
945                 950                 955                 960

Val Ala Asp Thr Asp Ala Val Asn Val Lys Gln Leu Lys Ser Ala Lys
                965                 970                 975

Thr Glu Val Glu Ser Thr Asp His Ser Val Val Ile Lys Glu Arg Gln
            980                 985                 990

Gly Asp Asn Gln Gln Ile Val Tyr  Asp Leu Ala Val Ala  Lys Thr Lys
        995                 1000                1005
```

```
Leu Thr  Ala Ser Lys Asp Lys  Arg Thr Ile Ser Ala  Ala Asp Lys
    1010                 1015                 1020

Ser Asn  His Phe Ala Thr Gly  Asp Glu Val Ala Val  Ala Ile Asn
    1025                 1030                 1035

Thr Ala  Thr Ala Ala Ala Arg  Thr Glu Val Glu Ala  Gly Lys Asn
    1040                 1045                 1050

Val Lys  Val Thr Ser Lys Thr  Gly Ala Asn Gly Gln  Asn Ile Tyr
    1055                 1060                 1065

Asn Val  Ser Val Ser Gly Asp  Leu Ser Asp Ile Thr  Ser Ile Ser
    1070                 1075                 1080

Asn Gly  Asp Thr Lys Val Ser  Leu Gly Lys Asp Lys  Gln Gly Asn
    1085                 1090                 1095

Pro Val  Val Asn Met Asn Gly  Ala Arg Ile Thr Asn  Val Gly Asp
    1100                 1105                 1110

Gly Ser  Ala Glu Gly Asp Ile  Val Asn Val Arg Gln  Leu Asn Lys
    1115                 1120                 1125

Val Val  Ser Ser Val Asn Thr  Gly Phe Asn Gln Leu  Ser Arg Asp
    1130                 1135                 1140

Ile Gly  Arg Val Asp Val Asn  Ala Arg Ala Gly Ile  Ala Ser Ala
    1145                 1150                 1155

Val Ala  Met Ala Asn Leu Pro  Gln Ile Phe Leu Pro  Gly Lys Ser
    1160                 1165                 1170

Ala Ile  Ser Val Ser Asn Ala  Gln Tyr Arg Gly Gln  Ser Ala Tyr
    1175                 1180                 1185

Ala Ile  Gly Tyr Ser Arg Ile  Ser Asp Asn Gly Lys  Trp Leu Ile
    1190                 1195                 1200

Arg Ala  Ser Val Gly Ser Asn  Thr Gln Arg Asp Thr  Ala Ile Gly
    1205                 1210                 1215

Gly Gly  Val Ser Phe Val Trp
    1220                 1225
```

<210> SEQ ID NO 5
<211> LENGTH: 4500
<212> TYPE: DNA
<213> ORGANISM: Haemophilus parasuis

<400> SEQUENCE: 5

```
atgaataaaa tatttagagt tatttggagt catgctcaac aggcttgggt ggttgtatct     60

gagttagtaa agtcttatac caaaacatcc gcttacacgg ataaaagagc tcaagtatgc    120

acctcagatt attttttaga taaacagcaa gataaattta aattaagtct tttaagtcta    180

gtattactgg gtatattttt tagtccagta gcaggttcaa ttactgattc atcatatttt    240

caacatggtg ctacttacgg gactaaacat aaatctgacg ccggtactat tggtattggt    300

agacagagta cggctgggcc tggttctatt gccatcggtc agcatacaaa agctgatggt    360

aggactgttg ttgcgatagg ttattcagca gtaacgacag atataggctc ccctgttgcg    420

ataggcggcc acactagcgc aaatggggag agcgcaattg ccatagggct taagtcaagt    480

tcgggaggaa aggaatctat tgtcttaggc aacaacgcca atacgacaac tggtcaaaca    540

gttgtaatag gtgcacatgc tagtgcaaaa gggcaacaat ctgttgctat cggggcagat    600

accaaagcgg atgggtatgg ctccatatca atcggtggag atgatttaaa aacaacgaaa    660

tatcacaagg gtagccattc cagcacaact gcgaaaggta aggcctctgt tgctattggg    720

ggtatgtctt tggctggggg cgaaggatct attgttttag gtcctgtagc atctgcaagt    780
```

-continued

```
catgttgaag gcattgctat cggtgcgaga agtaagtcta ccgctgatta cggtattgcg    840
gttggtggtg gtgcaactgc tggaaagaac gccgttgctg ttggtaggga gtcgaaaggt    900
actgggacaa attccattgc gataggtaat tctgcgagaa caacaggggc agactctgtt    960
gttgtgggtg ccaatatcaa tgtgacagat ggacaattag tggcaattgg ataccaagca   1020
agtgctaaaa gtcgttctac tgccttgggt tataaagcct ctgccggtgg taggagctct   1080
gttgctgtgg gtgaagaggc aaagacaaca ccagacagag caaccgcact tggtaataat   1140
accgttgtct ccgtgggtgg cggtgtggca ttaggttatg gatctaatgc aaatacagct   1200
ggcggtgtag aggggttaaa acaagctcat tctgtcacaa cggaaccaag cactgacaag   1260
aacggcttta aatccacaga aaaggttgat ggtaataaga ttggtgcggt ttctgtcggt   1320
gtaggctcag gtagtaaact catcaaacgc caaatcacca acgttgctgc aggtaaagaa   1380
ttaaccgatg cagtaaacgt ggcacagctt aaatcgctca ccatgctaat aggaggcgat   1440
aacagcagca gtggcaaggt aggcatttgg gatggcaaac ttgaagttaa aggcacaaat   1500
ggcgaaatca agaccaatgc gtctggctca accatcacaa tatcactaga cgataagatt   1560
aaaaaacaat tagctgatgc caaagcagga agtttgacat tcaaaggcga aaaaacaggt   1620
acaggtacaa taacaaatga tgtttcgggt caaaaatgga atgccaacca agataagacc   1680
gttaccatta caagtaaaga aacataccaa aatggtggtg ttcgatacaa aggcgataac   1740
attgaaattt atcgtaaaaa tcttaacaat ggaaacacag aattccatgt gttgatgaaa   1800
gatacaccaa cattcagcag cgttcaatat ggcaataatg gacctaagat taccagcact   1860
ggcggtaatc taaaagtaac aggtgcaaac ggcacttccc cagttaagat caccaattta   1920
gcacaaggta cacaaaataa cgatgcggtg aactacatgc aattttcaaa tgctggttgg   1980
aaacttgcaa ttgctcaggg aacggggggg caagcaactc cacctacggc acatcttatc   2040
aaaataggcg ataccgcaac ctttaccgct ggaaataata ttaaattaga acaaaataac   2100
ggaaatatta cgatttctac gattggtaag ttaattaaaa agactgaaag cctagcaaat   2160
ggtgatttga aaattactta tacggatgac acccatgata ctattgctaa ggggaaagac   2220
ggtaaaaatg gtgcgaaagg tgatggaggg gaacaaggct cagcagggcc tagaggcgaa   2280
gcaggtccag caggatcaca aggtgcaact ggtcctgtag gtccaaaagg agatgcagga   2340
gtaaaaggcg ataggggtga gcgtggtgaa gcaggagcag tgggccctca agatcctgcg   2400
ggtgcaactg gctctgcggg tccagcaggg gctaggggtg aacagggttc taaaggagat   2460
acaggtccta aggagatac aggtccaaaa ggcgaagctg gttcaacagg ttcgatgggt   2520
ccagtggatc cgaaaggtga aaaaggagat caagattcga tgggtccagc agaaccacaa   2580
ggacctacgg gtccaacggg accacaagga cctacgggtc caacgggacc acaaggacct   2640
acggggccaa cgggaccaca aggccctgcg agtccaacgg gatcacaagg ccctgcgagt   2700
ccaacgggat cacaaggacc tgcgggtcca acgggtccag caggaccaca aggacctacg   2760
ggtccaacgg ggcctgcggg tccaacggga ccacaaggac ctgcgggtcc agcaggacca   2820
caaggaccgc agggtccagc aggaccacaa ggacctgcgg gtccaacggg gcctgctggt   2880
ccaaaaggag aaaatgtggg aagtggttta ggtttgaaag atgatgctga atcaaataaa   2940
acggcactta cccctacaga tgcacaaaaa gctattgctg gtgataacaa agacggtaaa   3000
ggtggcttat tggctcaaac gggtaatgcg ttaaataatg cagcgacagt aaaagactta   3060
caagccattg cacaagcggg cttagacttg acgggtaaca acgccgatac cactgtacat   3120
cgtccattgg gtacgaagtt aaccgttgag ggtgaaggca aatggaatgg taaggactca   3180
```

-continued

```
gcggctaata acctttatgt ggaagcacaa gaggcagata acaaacttgt tgtgaaaatg   3240

aacagggatt taacgaactt aaattctgtg actttaggca ctgcgacaat gactggtgat   3300

aagaatacaa tcaaccttac tggtgcagga gagaaagtcg aggaagagtt tgttaaatgg   3360

gacccagtga ctaaacaacc tattcttgat gagaatggca atctccagaa atataaagag   3420

aaagttgatc ctcgtgtgaa actgagtggt attgctgatg gtgatatttc accaaatagt   3480

actgatgcag tgaatggtcg ccaagtttat gttttaacca atcgtatcag gttcttccac   3540

accaatgatg gtcataatgc agaggagcaa attaaccata agtcgaatac agtggactca   3600

atagcttcag gttcatactc tactgcagtt ggttacaaag ctcacgcgaa aggggataga   3660

gcggtcgcat ttggtaacag tacattagct ggcatacaat cggtggctat tggtaacgtt   3720

gcaattgctt caggcgaaaa atcgatagct attggtgata atgctaaggc tgtgggcaac   3780

caatctatct ctatcggtac gggtaacgta gtgaacggca ataactccgg tgcatttggt   3840

gacccaagtg tgattaatgc tgataactct tattctgtgg gtaacaataa tacgattgag   3900

aacgaaaatg tctttgcatt gggtaacaag attaccaata caaccaacaa ctcggtattc   3960

ttgggaacaa actcaggcta tgtggcagca ggtgcaacca ctgcgggagc gggtgcttta   4020

gaataccaag taataggtgg tgtgtataac gcttatgccg gcggtaaagc aactgaagtt   4080

gtaggcgtgg tgagcgtggg taatgtagac agtgatggca aaatggaaac tcgtcgtatt   4140

caaaacgttg cacctggttt aatctctgag caaagtaccg atgcgattaa tggtagccag   4200

ttgtatagct taatatctca gcacaaggtg catatgggcg atattcacaa taagatcaac   4260

cgtaataata aagctctgcg tgcgggtatt gcaggttcta acgccgcagc aggtttacca   4320

caggtttatc tcccaggtaa gtcaatgatt gcagcatcag cggggacttt caaaggtcaa   4380

tctgcattag cagtgggtta ctcaagagca tcagataacg gcaagctgat ccttaaatta   4440

caaggtaatg caaatactag tggtgaaatg ggcggctctg tgggggtagg ttatcagtgg   4500
```

<210> SEQ ID NO 6
<211> LENGTH: 1500
<212> TYPE: PRT
<213> ORGANISM: haemophilus parasuis

<400> SEQUENCE: 6

```
Met Asn Lys Ile Phe Arg Val Ile Trp Ser His Ala Gln Gln Ala Trp
1               5                   10                  15

Val Val Val Ser Glu Leu Val Lys Ser Tyr Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Gly
    50                  55                  60

Ile Phe Phe Ser Pro Val Ala Gly Ser Ile Thr Asp Ser Ser Tyr Phe
65                  70                  75                  80

Gln His Gly Ala Thr Tyr Gly Thr Lys His Lys Ser Asp Ala Gly Thr
                85                  90                  95

Ile Gly Ile Gly Arg Gln Ser Thr Ala Gly Pro Gly Ser Ile Ala Ile
            100                 105                 110

Gly Gln His Thr Lys Ala Asp Gly Arg Thr Val Val Ala Ile Gly Tyr
        115                 120                 125

Ser Ala Val Thr Thr Asp Ile Gly Ser Pro Val Ala Ile Gly Gly His
    130                 135                 140

Thr Ser Ala Asn Gly Glu Ser Ala Ile Ala Ile Gly Leu Lys Ser Ser
```

-continued

```
145                 150                 155                 160

Ser Gly Gly Lys Glu Ser Ile Val Leu Gly Asn Asn Ala Asn Thr Thr
                165                 170                 175

Thr Gly Gln Thr Val Val Ile Gly Ala His Ala Ser Ala Lys Gly Gln
            180                 185                 190

Gln Ser Val Ala Ile Gly Ala Asp Thr Lys Ala Asp Gly Tyr Gly Ser
        195                 200                 205

Ile Ser Ile Gly Gly Asp Asp Leu Lys Thr Thr Lys Tyr His Lys Gly
    210                 215                 220

Ser His Ser Ser Thr Thr Ala Lys Gly Lys Ala Ser Val Ala Ile Gly
225                 230                 235                 240

Gly Met Ser Leu Ala Gly Gly Glu Gly Ser Ile Val Leu Gly Pro Val
                245                 250                 255

Ala Ser Ala Ser His Val Glu Gly Ile Ala Ile Gly Ala Arg Ser Lys
            260                 265                 270

Ser Thr Ala Asp Tyr Gly Ile Ala Val Gly Gly Gly Ala Thr Ala Gly
        275                 280                 285

Lys Asn Ala Val Ala Val Gly Arg Glu Ser Lys Gly Thr Gly Thr Asn
    290                 295                 300

Ser Ile Ala Ile Gly Asn Ser Ala Arg Thr Thr Gly Ala Asp Ser Val
305                 310                 315                 320

Val Val Gly Ala Asn Ile Asn Val Thr Asp Gly Gln Leu Val Ala Ile
                325                 330                 335

Gly Tyr Gln Ala Ser Ala Lys Ser Arg Ser Thr Ala Leu Gly Tyr Lys
            340                 345                 350

Ala Ser Ala Gly Gly Arg Ser Ser Val Ala Val Gly Glu Glu Ala Lys
        355                 360                 365

Thr Thr Pro Asp Arg Ala Thr Ala Leu Gly Asn Asn Thr Val Val Ser
    370                 375                 380

Val Gly Gly Gly Val Ala Leu Gly Tyr Gly Ser Asn Ala Asn Thr Ala
385                 390                 395                 400

Gly Gly Val Glu Gly Leu Lys Gln Ala His Ser Val Thr Thr Glu Pro
                405                 410                 415

Ser Thr Asp Lys Asn Gly Phe Lys Ser Thr Glu Lys Val Asp Gly Asn
            420                 425                 430

Lys Ile Gly Ala Val Ser Val Gly Val Gly Ser Gly Ser Lys Leu Ile
        435                 440                 445

Lys Arg Gln Ile Thr Asn Val Ala Ala Gly Lys Glu Leu Thr Asp Ala
    450                 455                 460

Val Asn Val Ala Gln Leu Lys Ser Leu Thr Met Leu Ile Gly Gly Asp
465                 470                 475                 480

Asn Ser Ser Ser Gly Lys Val Gly Ile Trp Asp Gly Lys Leu Glu Val
                485                 490                 495

Lys Gly Thr Asn Gly Glu Ile Lys Thr Asn Ala Ser Gly Ser Thr Ile
            500                 505                 510

Thr Ile Ser Leu Asp Asp Lys Ile Lys Lys Gln Leu Ala Asp Ala Lys
        515                 520                 525

Ala Gly Ser Leu Thr Phe Lys Gly Glu Lys Thr Gly Thr Gly Thr Ile
    530                 535                 540

Thr Asn Asp Val Ser Gly Gln Lys Trp Asn Ala Asn Gln Asp Lys Thr
545                 550                 555                 560

Val Thr Ile Thr Ser Lys Glu Thr Tyr Gln Asn Gly Gly Val Arg Tyr
                565                 570                 575
```

-continued

```
Lys Gly Asp Asn Ile Glu Ile Tyr Arg Lys Asn Leu Asn Asn Gly Asn
            580                 585                 590

Thr Glu Phe His Val Leu Met Lys Asp Thr Pro Thr Phe Ser Ser Val
        595                 600                 605

Gln Tyr Gly Asn Asn Gly Pro Lys Ile Thr Ser Thr Gly Gly Asn Leu
    610                 615                 620

Lys Val Thr Gly Ala Asn Gly Thr Ser Pro Val Lys Ile Thr Asn Leu
625                 630                 635                 640

Ala Gln Gly Thr Gln Asn Asn Asp Ala Val Asn Tyr Met Gln Phe Ser
                645                 650                 655

Asn Ala Gly Trp Lys Leu Ala Ile Ala Gln Gly Thr Gly Gly Gln Ala
            660                 665                 670

Thr Pro Pro Thr Ala His Leu Ile Lys Ile Gly Asp Thr Ala Thr Phe
        675                 680                 685

Thr Ala Gly Asn Asn Ile Lys Leu Glu Gln Asn Asn Gly Asn Ile Thr
    690                 695                 700

Ile Ser Thr Ile Gly Lys Leu Ile Lys Lys Thr Glu Ser Leu Ala Asn
705                 710                 715                 720

Gly Asp Leu Lys Ile Thr Tyr Thr Asp Asp Thr His Asp Thr Ile Ala
                725                 730                 735

Lys Gly Lys Asp Gly Lys Asn Gly Ala Lys Gly Asp Gly Gly Glu Gln
            740                 745                 750

Gly Ser Ala Gly Pro Arg Gly Glu Ala Gly Pro Ala Gly Ser Gln Gly
        755                 760                 765

Ala Thr Gly Pro Val Gly Pro Lys Gly Asp Ala Gly Val Lys Gly Asp
    770                 775                 780

Arg Gly Glu Arg Gly Glu Ala Gly Ala Val Gly Pro Gln Asp Pro Ala
785                 790                 795                 800

Gly Ala Thr Gly Ser Ala Gly Pro Ala Gly Ala Arg Gly Glu Gln Gly
                805                 810                 815

Ser Lys Gly Asp Thr Gly Pro Lys Gly Asp Thr Gly Pro Lys Gly Glu
            820                 825                 830

Ala Gly Ser Thr Gly Ser Met Gly Pro Val Asp Pro Lys Gly Glu Lys
        835                 840                 845

Gly Asp Gln Asp Ser Met Gly Pro Ala Glu Pro Gln Gly Pro Thr Gly
    850                 855                 860

Pro Thr Gly Pro Gln Gly Pro Thr Gly Pro Thr Gly Pro Gln Gly Pro
865                 870                 875                 880

Thr Gly Pro Thr Gly Pro Gln Gly Pro Ala Ser Pro Thr Gly Ser Gln
                885                 890                 895

Gly Pro Ala Ser Pro Thr Gly Ser Gln Gly Pro Ala Gly Pro Thr Gly
            900                 905                 910

Pro Ala Gly Pro Gln Gly Pro Thr Gly Pro Thr Gly Pro Ala Gly Pro
        915                 920                 925

Thr Gly Pro Gln Gly Pro Ala Gly Pro Ala Gly Pro Gln Gly Pro Gln
    930                 935                 940

Gly Pro Ala Gly Pro Gln Gly Pro Ala Gly Pro Thr Gly Pro Ala Gly
945                 950                 955                 960

Pro Lys Gly Glu Asn Val Gly Ser Gly Leu Gly Leu Lys Asp Asp Ala
                965                 970                 975

Glu Ser Asn Lys Thr Ala Leu Thr Pro Thr Asp Ala Gln Lys Ala Ile
            980                 985                 990

Ala Gly Asp Asn Lys Asp Gly Lys  Gly Gly Leu Leu Ala  Gln Thr Gly
        995                 1000                1005
```

-continued

```
Asn Ala  Leu Asn Asn Ala Ala  Thr Val Lys Asp Leu  Gln Ala Ile
    1010                 1015                 1020

Ala Gln  Ala Gly Leu Asp Leu  Thr Gly Asn Asn Ala  Asp Thr Thr
    1025                 1030                 1035

Val His  Arg Pro Leu Gly Thr  Lys Leu Thr Val Glu  Gly Glu Gly
    1040                 1045                 1050

Lys Trp  Asn Gly Lys Asp Ser  Ala Ala Asn Asn Leu  Tyr Val Glu
    1055                 1060                 1065

Ala Gln  Glu Ala Asp Asn Lys  Leu Val Val Lys Met  Asn Arg Asp
    1070                 1075                 1080

Leu Thr  Asn Leu Asn Ser Val  Thr Leu Gly Thr Ala  Thr Met Thr
    1085                 1090                 1095

Gly Asp  Lys Asn Thr Ile Asn  Leu Thr Gly Ala Gly  Glu Lys Val
    1100                 1105                 1110

Glu Glu  Glu Phe Val Lys Trp  Asp Pro Val Thr Lys  Gln Pro Ile
    1115                 1120                 1125

Leu Asp  Glu Asn Gly Asn Leu  Gln Lys Tyr Lys Glu  Lys Val Asp
    1130                 1135                 1140

Pro Arg  Val Lys Leu Ser Gly  Ile Ala Asp Gly Asp  Ile Ser Pro
    1145                 1150                 1155

Asn Ser  Thr Asp Ala Val Asn  Gly Arg Gln Val Tyr  Val Leu Thr
    1160                 1165                 1170

Asn Arg  Ile Arg Phe Phe His  Thr Asn Asp Gly His  Asn Ala Glu
    1175                 1180                 1185

Glu Gln  Ile Asn His Lys Ser  Asn Thr Val Asp Ser  Ile Ala Ser
    1190                 1195                 1200

Gly Ser  Tyr Ser Thr Ala Val  Gly Tyr Lys Ala His  Ala Lys Gly
    1205                 1210                 1215

Asp Arg  Ala Val Ala Phe Gly  Asn Ser Thr Leu Ala  Gly Ile Gln
    1220                 1225                 1230

Ser Val  Ala Ile Gly Asn Val  Ala Ile Ala Ser Gly  Glu Lys Ser
    1235                 1240                 1245

Ile Ala  Ile Gly Asp Asn Ala  Lys Ala Val Gly Asn  Gln Ser Ile
    1250                 1255                 1260

Ser Ile  Gly Thr Gly Asn Val  Val Asn Gly Asn Asn  Ser Gly Ala
    1265                 1270                 1275

Phe Gly  Asp Pro Ser Val Ile  Asn Ala Asp Asn Ser  Tyr Ser Val
    1280                 1285                 1290

Gly Asn  Asn Asn Thr Ile Glu  Asn Glu Asn Val Phe  Ala Leu Gly
    1295                 1300                 1305

Asn Lys  Ile Thr Asn Thr Thr  Asn Asn Ser Val Phe  Leu Gly Thr
    1310                 1315                 1320

Asn Ser  Gly Tyr Val Ala Ala  Gly Ala Thr Thr Ala  Gly Ala Gly
    1325                 1330                 1335

Ala Leu  Glu Tyr Gln Val Ile  Gly Gly Val Tyr Asn  Ala Tyr Ala
    1340                 1345                 1350

Gly Gly  Lys Ala Thr Glu Val  Val Gly Val Val Ser  Val Gly Asn
    1355                 1360                 1365

Val Asp  Ser Asp Gly Lys Met  Glu Thr Arg Arg Ile  Gln Asn Val
    1370                 1375                 1380

Ala Pro  Gly Leu Ile Ser Glu  Gln Ser Thr Asp Ala  Ile Asn Gly
    1385                 1390                 1395

Ser Gln  Leu Tyr Ser Leu Ile  Ser Gln His Lys Val  His Met Gly
```

1400 1405 1410

Asp Ile His Asn Lys Ile Asn Arg Asn Asn Lys Ala Leu Arg Ala
1415 1420 1425

Gly Ile Ala Gly Ser Asn Ala Ala Ala Gly Leu Pro Gln Val Tyr
1430 1435 1440

Leu Pro Gly Lys Ser Met Ile Ala Ala Ser Ala Gly Thr Phe Lys
1445 1450 1455

Gly Gln Ser Ala Leu Ala Val Gly Tyr Ser Arg Ala Ser Asp Asn
1460 1465 1470

Gly Lys Leu Ile Leu Lys Leu Gln Gly Asn Ala Asn Thr Ser Gly
1475 1480 1485

Glu Met Gly Gly Ser Val Gly Val Gly Tyr Gln Trp
1490 1495 1500

<210> SEQ ID NO 7
<211> LENGTH: 7236
<212> TYPE: DNA
<213> ORGANISM: Haemophilus parasuis

<400> SEQUENCE: 7
atgaataaaa tatttagagt tatttggagt catgctcaac aggcttgggt ggttgtatct 60
gagttagtaa agtctcatac caaaacatcc gcttacacgg ataaaagagc tcaagtatgc 120
acctcagatt attttttaga taaacagcaa gataaattta aattaagtct tttaagtcta 180
gtattactag gtatattttt tagttcagta ggttcagctg catatcttca agatggtgct 240
aatgagggat cgaatatagg aactgacgac ggtactattg gtattggtca agagagtagg 300
gcttcgtatg gtgctgttgc tatcggtcag aaggcaaaag ctgaagctag gcataatatt 360
gcgataggtt atggagcaga ttcaggaaca caagtaaact ctcttgcgat aggctaccgc 420
actacagtaa gtgggactgg agcaattgcc ttaggcaaag aagccaattc gacaaatagt 480
caaacaattg ccatcgggag tgattcaaaa gcgagcggag atgaatctat tgccttaggc 540
ggacaagcca attcgacaaa taatcaaaca attgccatcg ggagtgattc aaaagcgagc 600
ggagaacaat ctattgtctt aggcacaggg gccagtgtga caggtactca aacaattgta 660
ataggcgcac gtgctagtgc aagtgggcac caatctgttg ctatcggggc aaatacccaa 720
gcgcaggggt atggctccat atcaatcggt ggagatgatt tagctacaac gaaatatcaa 780
gatgatgctc aagactattc ccaaacaaca attgcgagag gtgatgcctc tgttgctatt 840
gggggtaggt cttcggctag tggcgacgga tctattgttg taggtccttt agcatctgca 900
actcatgctg aaggcattgc tatcggtgcg agaagtaggt ctaacaatga gtacggtatt 960
gcggttggtg gtggtgcaca tgctggaaag cactccattg ctgttggtaa aagtgctact 1020
gcaagtcaaa gaggagcttc cgcattcggt gaagaggcac gagcagtcgg acagtttaca 1080
acagcattgg ggagttatgc ggaagcagaa acgcaagatg gcgttgctct aggttatcga 1140
tccaaaacta gtcgtcagtc agggcgagca ggttggaaac cagataatac aaattattct 1200
attaacggaa gtacattatc tgctacgcat gcagcggtag cagtaggtga tgacctcacc 1260
gtcactcgtc aaattaccag tgttgctgca gggacagcag atactgacgc agcaaacgtg 1320
gcgcaattaa aagcactgac tttaaagatc agtggcgata gaaatacgca gggtcacaca 1380
acattttata acgaaacgct ctcaattgta ggggctgatg gtattagtac ggcagttgag 1440
cagagaaatg gcaattcaaa aattaccatt actggctcaa aaacgtattt tcatactaac 1500
tataacgatc agtctcaagg tcggggagat cctacgacta atttcggcac aattactgac 1560

-continued

```
aaagctggag ctacaggaac ctatgcaata acagcagggg taaatgcctc tgcggctgga   1620
aattatggta ttgcgatggg gtataagagt aatgctagtg cttatgctgt tgctcttggt   1680
agtgaatcga aggtgctgg gacagattcc attgcgatag gtaatcttgc gagaacaaca   1740
ggggtagact ctgttgttgt gggtgcccat atcaatgtga caggtcaaaa atcagtggca   1800
gttggacgcc aagcaaatgc tagagattat tctactgcct tgggttataa agcctctgcc   1860
aatggtacgt actctgttgc tgtgggtgaa aatgccacga taaatgtaaa tgctgctaga   1920
tcaaccgcac ttggtcataa taccgttgtc accgtgggtg gcggtgtggc attaggttat   1980
ggatctagtg caagtacagc tggcggtgta gtggggttaa aacaagctca ttctgtcaca   2040
acgggaacaa gcactgaagc taacggcttt aaatccacac aaaaggttga tggtaataat   2100
attggtgcag tttctgtggg tggtacaacc atcaaacgcc aaatcgtcaa tgtggcggct   2160
ggtacacaag ataccgatgc ggtaaacgtg gcacagctta aatctttgac gatgaaaatt   2220
gctggtgata ccaatactaa tctacagcca aaagtggggt tgtgggatgg tacgcttaaa   2280
gtgctaggca caaatggcga aatcaagacc aatgcgtctg gctcaaccat tacaatatca   2340
ctagacgata cgattaaaaa taaattagct gatgccagag caggaagttt gatattcaag   2400
ggcgaaaaaa caaataacgg tacaacaaat gatgttttgg gtcaaaaatg gaatgccaac   2460
aaagatgaga ccgttaccat taaaagtgac gaaacatacc taaacggtgg tgttcgatac   2520
aaaggcgata acattgaaat ttatcgtaga aatctagaat tccatgtatt gatgaaagat   2580
gcaccaacat tcagcagcgt tcaatatggc gataatggac ctaagattac cagcaccact   2640
ggcggtaatc taaaagtaac aggtacagac ggcacttccc cagttaagat caccaattta   2700
gcacaaggta cacaaaataa cgatgcggtg aactacatgc aattttcaaa tgctggttgg   2760
aaacttgcaa ttgctccggg agcgggtggt caagcaactc cacctggggc acatcttatc   2820
aaaataaacg ataccgtaac ctttaccgct ggaaataata ttaaattaga acaagcgggc   2880
ggaaatatta cgatttctac gattggtaag ttaattaaag agactaaaac cttagataat   2940
ggcgatctaa aaattaccta tacagataat acggatagca tcatcaaaaa aggtgaaaaa   3000
ggagatacag gtcctagagg tgaaacaggc cctgcgggtc cgattggtcc agtgggtcca   3060
gcaggggcta ggggtgagcg aggccctgca ggtgtagctg gacctaaggg tgagaaaggt   3120
gatccaggac caaaaggcga aactggtcca acaggtccga gggggccagt gggtccacaa   3180
ggaccgcagg gaaaagcggg tgctcaggga cagaagggtg agcgaggaga aacaggccct   3240
gcaggtgcag ttggaccaca aggtgtacct ggccctgcgg gtccagcagg gcctaggggt   3300
gagcgaggcg aaccaggaca aacgggtcca gcaggcccag cgggagagcg aggcgagcgg   3360
ggtcctaaag gagatagagg tccaaaaggt gatacaggtg agagaggtgc aactggccct   3420
gcgggtccga tgggtccagc aggcccagcg ggagagcgag gtgcacctgg tcctgcgggt   3480
ccaaaaggag atgcaggaga aaaaggcgat aagggtgccc gtggtgaagc aggaccaatg   3540
ggccctcaag gtcctagagg tgagcaaggt ctaagaggtg aacgaggccc agcgggtcct   3600
agaggcgaaa ctggtttaac aggtccgagg ggtccagtgg gaccacaagg accgcaagga   3660
acaccgggta ctccgggaca gaagggggat aaaggcgatc caggacctgc gggtccagca   3720
gggcctaggg gtgagcgagg agaaactggc cctgcgggtc cgatgggtcc agcaggccca   3780
gcgggagagc gaggtgcacc tggtcctgcg ggtccaaaag gagatgcagg agaaaaaggc   3840
gataagggtg cccgtggtga agcaggacca atgggccctc aaggtcctag aggtgagcaa   3900
ggtctaagag gtgaacgagg cccagcgggt cctagaggcg aaactggttt aacaggtccg   3960
```

-continued

```
aggggtccag tgggaccaca aggaccgcaa ggaacaccgg gtactccggg acagaagggg   4020
gataaaggcg atccaggacc tgcgggtcca gcagggccta ggggtgagcg aggagaaact   4080
ggccctgcag gtgcagctgg tcctgcgggt cctagaggcg aacgagggct tccaggggta   4140
gcaggtccta agggcgatag aggcgaagct ggtcctagag gcgaagctgg tcctgctgga   4200
gcaacaggac cacaaggtcc aaaaggagat aatggagctc caggtcctag ggagagagaa   4260
ggtgaacctg gccctgcggg tccgattggt ccagtgggtc cagcaggggc tgctggtcca   4320
gcaggtccag cgggagagcg aggccctgcg ggtgagcgag gagaaactgg ccctgcaggt   4380
gcagctggtc ctgctggtcc agcaggagca gtgggccctc aaggtcctac gggtgcaact   4440
ggacctgcgg gtccagtagg gccacgagga ccacagggaa cagcgggtgc tcagggacct   4500
aagggtgagc gaggccctgc aggtgaaact ggacctaagg gtgagaaagg tgatccagga   4560
ccaaaaggcg aaactggtcc aacaggtcca gtgggtccag caggaccagc gggagagcga   4620
ggcgagcagg gtcctagggg ggaacaaggt gcaactggcc ctgcgggtcc aacggggcct   4680
aggggtgaac cgggtccaac gggaccacaa ggaccgcaag gaacaccggg tactccggga   4740
cagaaggggg ataaaggcga tccaggacaa gcgggtccag caggaccacg aggccctgca   4800
ggtgcagctg gacctgcggg cccagcaggg cctaggggtg accgaggaga aactggtcct   4860
gcgggtccaa caggggctaa gggtgaacag ggtcaaaaag gagatacagg tccaatgggg   4920
cctgctggtc caaaaggtga tgcaggtcct agaggcgaag ctggtcctgc tggagcaaca   4980
ggaccacaag gtccaaaagg agataatgga gctacaggtc ctaggggaga gaaaggtgaa   5040
cctggccctg cgggtccgat tggtccagtg ggtccagcag gggctgctgg tccagcagga   5100
ccacgaggac ctgcaggtgc agctggacct aagggtgaca aaggtgatac tggtcagaaa   5160
ggtgaaaaag gagatcgtgg tgaaaaaggt ctaaaaggcg atagaggtga aactggccct   5220
agaggcgaag ctggtcctag aggcgaagct ggtcctgctg gagcaacagg accacaaggt   5280
ccaaaaggag ataatggagc tccaggtcct aggggagaga aaggtgaacc tggccctgcg   5340
ggtccgattg gtccagtggg tccagcaggg gctgctggtc cagcaggtcc agcgggagag   5400
cgaggccctg cgggtgagcg aggagaaact ggccctgcgg gtccaacagg ggctaagggt   5460
gaacagggtc ctgaaggtaa acaaggtatt caaggacctg cgggtccagc agggcctagg   5520
ggtgagcgag gagaaactgg ccctgcaggt gcagctggtc ctgctggtcc agcaggagca   5580
gtgggccctc aaggtcctac gggtgcaact ggacctgcgg gtccagtagg gccacgagga   5640
ccacagggaa cagcgggtgc tcagggacct aagggtgagc gaggccctgc aggtgaaact   5700
ggacctaagg gtgagaaagg tgatccagga ccaaaaggcg aaactggtcc aacaggtcca   5760
gtgggtccag caggaccagc gggagagcga ggcgagcagg gtcctagggg ggaacaaggt   5820
gcaactggcc ctgcgggtcc agcaggacca cgaggccctg caggtgcagc tggacctaag   5880
ggtgacaaag gtgatactgg tcagaaaggt gaaactggcc ctgcgggtcc agtaggtcca   5940
actggaccac aaggtgcacc tggtcctgcg ggcccagcag gcccagcggg agagcgaggc   6000
cctacgggtc ctaaaggaga tgcaggtcca aaaggagata caggtcagaa aggagaaact   6060
ggccctgcgg gtccagcagg ggctaagggt gaaccgggtc ctagaggtga gcaaggtatt   6120
caaggaccta cgggtccaac gggaccacaa ggaccgcagg gaacagcggg tattcaggga   6180
cctaagggtg agcgaggaaa tgtgagtgtc agcggtttac cgatcgagta tgcaacggaa   6240
gacggcaaat caattatcaa tatgggcggt aatttctatt tggaagaacc tgctaaagat   6300
ggttcgatta agttaattcc agtggtgaat gttaaaggta aattctcaac caaaacgcaa   6360
```

-continued aatccagatg gcagtattac gcttaagtca ttagcagtaa aagtgaattt ggcaaatgaa 6420
actccgatgg tattaggtaa tgtcgctgaa ggggtagcag atacggacgc tgttaatgtg 6480
aaacagttga aatctgcgaa aactgaagtg gaatctaccg atcacagtgt ggtgattaaa 6540
gagcgtcagg gcgataatca gcaaatcgtg tatgatttgg cggttgctaa aacgaaactc 6600
actgcctcta aggataaacg caccattagt gcagcagata aaggcaacca ttttgcgaca 6660
ggagatgaag tcgcagtagc aattaatacc gcaacagcag ccgcaagaac tgaagttgaa 6720
gcgggtaaaa atgtgaaagt gacttcaaaa acgggggcaa atggtcagaa tatttacaat 6780
gtgagcgtgt ttggagattt aagcgacatt acttcaatta gtaatggcga taccaaagta 6840
tctttaggta aagataagca aggaaatcca gttgtaaata tgaatggtgc cagaattacc 6900
aacgttggag atggtagtgc tgagggcgat attgtgaatg tgcgtcagct caacaaagtg 6960
gtttcttctg tgaatacagg atttaatcaa ttatcaagag atattgttaa tgcaagagcg 7020
ggtattgctt ctgctggggc gatggctaat ttgccacaaa tttctttacc aggtaaaagt 7080
gctatttctg tttctaatgc acaatatcgc gggcaatctg cctatgctat aggttattcc 7140
aaaatttctg ataatggcaa atggcttatt cgagcgtctg ttagcagtaa tactcagcgg 7200
gatactatga ttggaggagg ggtaggtttt gtgtgg 7236

<210> SEQ ID NO 8
<211> LENGTH: 2412
<212> TYPE: PRT
<213> ORGANISM: haemophilus parasuis

<400> SEQUENCE: 8

Met Asn Lys Ile Phe Arg Val Ile Trp Ser His Ala Gln Gln Ala Trp
1 5 10 15

Val Val Val Ser Glu Leu Val Lys Ser His Thr Lys Thr Ser Ala Tyr
20 25 30

Thr Asp Lys Arg Ala Gln Val Cys Thr Ser Asp Tyr Phe Leu Asp Lys
35 40 45

Gln Gln Asp Lys Phe Lys Leu Ser Leu Leu Ser Leu Val Leu Leu Gly
50 55 60

Ile Phe Phe Ser Ser Val Gly Ser Ala Ala Tyr Leu Gln Asp Gly Ala
65 70 75 80

Asn Glu Gly Ser Asn Ile Gly Thr Asp Asp Gly Thr Ile Gly Ile Gly
85 90 95

Gln Glu Ser Arg Ala Ser Tyr Gly Ala Val Ala Ile Gly Gln Lys Ala
100 105 110

Lys Ala Glu Ala Arg His Asn Ile Ala Ile Gly Tyr Gly Ala Asp Ser
115 120 125

Gly Thr Gln Val Asn Ser Leu Ala Ile Gly Tyr Arg Thr Thr Val Ser
130 135 140

Gly Thr Gly Ala Ile Ala Leu Gly Lys Glu Ala Asn Ser Thr Asn Ser
145 150 155 160

Gln Thr Ile Ala Ile Gly Ser Asp Ser Lys Ala Ser Gly Asp Glu Ser
165 170 175

Ile Ala Leu Gly Gly Gln Ala Asn Ser Thr Asn Asn Gln Thr Ile Ala
180 185 190

Ile Gly Ser Asp Ser Lys Ala Ser Gly Glu Gln Ser Ile Val Leu Gly
195 200 205

Thr Gly Ala Ser Val Thr Gly Thr Gln Thr Ile Val Ile Gly Ala Arg
210 215 220

-continued

```
Ala Ser Ala Ser Gly His Gln Ser Val Ala Ile Gly Ala Asn Thr Gln
225                 230                 235                 240

Ala Gln Gly Tyr Gly Ser Ile Ser Ile Gly Gly Asp Asp Leu Ala Thr
                245                 250                 255

Thr Lys Tyr Gln Asp Asp Ala Gln Asp Tyr Ser Gln Thr Thr Ile Ala
            260                 265                 270

Arg Gly Asp Ala Ser Val Ala Ile Gly Gly Arg Ser Ser Ala Ser Gly
        275                 280                 285

Asp Gly Ser Ile Val Val Gly Pro Leu Ala Ser Ala Thr His Ala Glu
    290                 295                 300

Gly Ile Ala Ile Gly Ala Arg Ser Arg Ser Asn Asn Glu Tyr Gly Ile
305                 310                 315                 320

Ala Val Gly Gly Gly Ala His Ala Gly Lys His Ser Ile Ala Val Gly
                325                 330                 335

Lys Ser Ala Thr Ala Ser Gln Arg Gly Ala Ser Ala Phe Gly Glu Glu
            340                 345                 350

Ala Arg Ala Val Gly Gln Phe Thr Thr Ala Leu Gly Ser Tyr Ala Glu
        355                 360                 365

Ala Glu Thr Gln Asp Gly Val Ala Leu Gly Tyr Arg Ser Lys Thr Ser
    370                 375                 380

Arg Gln Ser Gly Arg Ala Gly Trp Lys Pro Asp Asn Thr Asn Tyr Ser
385                 390                 395                 400

Ile Asn Gly Ser Thr Leu Ser Ala Thr His Ala Ala Val Ala Val Gly
                405                 410                 415

Asp Asp Leu Thr Val Thr Arg Gln Ile Thr Ser Val Ala Ala Gly Thr
            420                 425                 430

Ala Asp Thr Asp Ala Ala Asn Val Ala Gln Leu Lys Ala Leu Thr Leu
        435                 440                 445

Lys Ile Ser Gly Asp Arg Asn Thr Gln Gly His Thr Thr Phe Tyr Asn
    450                 455                 460

Glu Thr Leu Ser Ile Val Gly Ala Asp Gly Ile Ser Thr Ala Val Glu
465                 470                 475                 480

Gln Arg Asn Gly Asn Ser Lys Ile Thr Ile Thr Gly Ser Lys Thr Tyr
                485                 490                 495

Phe His Thr Asn Tyr Asn Asp Gln Ser Gln Gly Arg Gly Asp Pro Thr
            500                 505                 510

Thr Asn Phe Gly Thr Ile Thr Asp Lys Ala Gly Ala Thr Gly Thr Tyr
        515                 520                 525

Ala Ile Thr Ala Gly Val Asn Ala Ser Ala Ala Gly Asn Tyr Gly Ile
    530                 535                 540

Ala Met Gly Tyr Lys Ser Asn Ala Ser Ala Tyr Ala Val Ala Leu Gly
545                 550                 555                 560

Ser Glu Ser Lys Gly Ala Gly Thr Asp Ser Ile Ala Ile Gly Asn Leu
                565                 570                 575

Ala Arg Thr Thr Gly Val Asp Ser Val Val Val Gly Ala His Ile Asn
            580                 585                 590

Val Thr Gly Gln Lys Ser Val Ala Val Gly Arg Gln Ala Asn Ala Arg
        595                 600                 605

Asp Tyr Ser Thr Ala Leu Gly Tyr Lys Ala Ser Ala Asn Gly Thr Tyr
    610                 615                 620

Ser Val Ala Val Gly Glu Asn Ala Thr Ile Asn Val Asn Ala Ala Arg
625                 630                 635                 640

Ser Thr Ala Leu Gly His Asn Thr Val Val Thr Val Gly Gly Gly Val
                645                 650                 655
```

-continued

```
Ala Leu Gly Tyr Gly Ser Ser Ala Ser Thr Ala Gly Gly Val Val Gly
            660                 665                 670

Leu Lys Gln Ala His Ser Val Thr Thr Gly Thr Ser Thr Glu Ala Asn
        675                 680                 685

Gly Phe Lys Ser Thr Gln Lys Val Asp Gly Asn Asn Ile Gly Ala Val
    690                 695                 700

Ser Val Gly Gly Thr Thr Ile Lys Arg Gln Ile Val Asn Val Ala Ala
705                 710                 715                 720

Gly Thr Gln Asp Thr Asp Ala Val Asn Val Ala Gln Leu Lys Ser Leu
                725                 730                 735

Thr Met Lys Ile Ala Gly Asp Thr Asn Thr Asn Leu Gln Pro Lys Val
            740                 745                 750

Gly Leu Trp Asp Gly Thr Leu Lys Val Leu Gly Thr Asn Gly Glu Ile
        755                 760                 765

Lys Thr Asn Ala Ser Gly Ser Thr Ile Thr Ile Ser Leu Asp Asp Thr
    770                 775                 780

Ile Lys Asn Lys Leu Ala Asp Ala Arg Ala Gly Ser Leu Ile Phe Lys
785                 790                 795                 800

Gly Glu Lys Thr Asn Asn Gly Thr Thr Asn Asp Val Leu Gly Gln Lys
                805                 810                 815

Trp Asn Ala Asn Lys Asp Glu Thr Val Thr Ile Lys Ser Asp Glu Thr
            820                 825                 830

Tyr Leu Asn Gly Gly Val Arg Tyr Lys Gly Asp Asn Ile Glu Ile Tyr
        835                 840                 845

Arg Arg Asn Leu Glu Phe His Val Leu Met Lys Asp Ala Pro Thr Phe
    850                 855                 860

Ser Ser Val Gln Tyr Gly Asp Asn Gly Pro Lys Ile Thr Ser Thr Thr
865                 870                 875                 880

Gly Gly Asn Leu Lys Val Thr Gly Thr Asp Gly Thr Ser Pro Val Lys
                885                 890                 895

Ile Thr Asn Leu Ala Gln Gly Thr Gln Asn Asn Asp Ala Val Asn Tyr
            900                 905                 910

Met Gln Phe Ser Asn Ala Gly Trp Lys Leu Ala Ile Ala Pro Gly Ala
        915                 920                 925

Gly Gly Gln Ala Thr Pro Pro Gly Ala His Leu Ile Lys Ile Asn Asp
    930                 935                 940

Thr Val Thr Phe Thr Ala Gly Asn Asn Ile Lys Leu Glu Gln Ala Gly
945                 950                 955                 960

Gly Asn Ile Thr Ile Ser Thr Ile Gly Lys Leu Ile Lys Glu Thr Lys
                965                 970                 975

Thr Leu Asp Asn Gly Asp Leu Lys Ile Thr Tyr Thr Asp Asn Thr Asp
            980                 985                 990

Ser Ile Ile Lys Lys Gly Glu Lys  Gly Asp Thr Gly Pro  Arg Gly Glu
        995                 1000                1005

Thr Gly  Pro Ala Gly Pro Ile  Gly Pro Val Gly Pro  Ala Gly Ala
    1010                1015                1020

Arg Gly  Glu Arg Gly Pro Ala  Gly Val Ala Gly Pro  Lys Gly Glu
    1025                1030                1035

Lys Gly  Asp Pro Gly Pro Lys  Gly Glu Thr Gly Pro  Thr Gly Pro
    1040                1045                1050

Arg Gly  Pro Val Gly Pro Gln  Gly Pro Gln Gly Lys  Ala Gly Ala
    1055                1060                1065

Gln Gly  Gln Lys Gly Glu Arg  Gly Glu Thr Gly Pro  Ala Gly Ala
```

```
    1070                1075                1080

Val Gly Pro Gln Gly Val Pro Gly Pro Ala Gly Pro Ala Gly Pro
    1085                1090                1095

Arg Gly Glu Arg Gly Glu Pro Gly Gln Thr Gly Pro Ala Gly Pro
    1100                1105                1110

Ala Gly Glu Arg Gly Glu Arg Gly Pro Lys Gly Asp Arg Gly Pro
    1115                1120                1125

Lys Gly Asp Thr Gly Glu Arg Gly Ala Thr Gly Pro Ala Gly Pro
    1130                1135                1140

Met Gly Pro Ala Gly Pro Ala Gly Glu Arg Gly Ala Pro Gly Pro
    1145                1150                1155

Ala Gly Pro Lys Gly Asp Ala Gly Glu Lys Gly Asp Lys Gly Ala
    1160                1165                1170

Arg Gly Glu Ala Gly Pro Met Gly Pro Gln Gly Pro Arg Gly Glu
    1175                1180                1185

Gln Gly Leu Arg Gly Glu Arg Gly Pro Ala Gly Pro Arg Gly Glu
    1190                1195                1200

Thr Gly Leu Thr Gly Pro Arg Gly Pro Val Gly Pro Gln Gly Pro
    1205                1210                1215

Gln Gly Thr Pro Gly Thr Pro Gly Gln Lys Gly Asp Lys Gly Asp
    1220                1225                1230

Pro Gly Pro Ala Gly Pro Ala Gly Pro Arg Gly Glu Arg Gly Glu
    1235                1240                1245

Thr Gly Pro Ala Gly Pro Met Gly Pro Ala Gly Pro Ala Gly Glu
    1250                1255                1260

Arg Gly Ala Pro Gly Pro Ala Gly Pro Lys Gly Asp Ala Gly Glu
    1265                1270                1275

Lys Gly Asp Lys Gly Ala Arg Gly Glu Ala Gly Pro Met Gly Pro
    1280                1285                1290

Gln Gly Pro Arg Gly Glu Gln Gly Leu Arg Gly Glu Arg Gly Pro
    1295                1300                1305

Ala Gly Pro Arg Gly Glu Thr Gly Leu Thr Gly Pro Arg Gly Pro
    1310                1315                1320

Val Gly Pro Gln Gly Pro Gln Gly Thr Pro Gly Thr Pro Gly Gln
    1325                1330                1335

Lys Gly Asp Lys Gly Asp Pro Gly Pro Ala Gly Pro Ala Gly Pro
    1340                1345                1350

Arg Gly Glu Arg Gly Glu Thr Gly Pro Ala Gly Ala Ala Gly Pro
    1355                1360                1365

Ala Gly Pro Arg Gly Glu Arg Gly Leu Pro Gly Val Ala Gly Pro
    1370                1375                1380

Lys Gly Asp Arg Gly Glu Ala Gly Pro Arg Gly Glu Ala Gly Pro
    1385                1390                1395

Ala Gly Ala Thr Gly Pro Gln Gly Pro Lys Gly Asp Asn Gly Ala
    1400                1405                1410

Pro Gly Pro Arg Gly Glu Lys Gly Glu Pro Gly Pro Ala Gly Pro
    1415                1420                1425

Ile Gly Pro Val Gly Pro Ala Gly Ala Ala Gly Pro Ala Gly Pro
    1430                1435                1440

Ala Gly Glu Arg Gly Pro Ala Gly Glu Arg Gly Glu Thr Gly Pro
    1445                1450                1455

Ala Gly Ala Ala Gly Pro Ala Gly Pro Ala Gly Ala Val Gly Pro
    1460                1465                1470
```

-continued

```
Gln Gly  Pro Thr Gly Ala Thr  Gly Pro Ala Gly Pro  Val Gly Pro
    1475                 1480                 1485

Arg Gly  Pro Gln Gly Thr Ala  Gly Ala Gln Gly Pro  Lys Gly Glu
    1490                 1495                 1500

Arg Gly  Pro Ala Gly Glu Thr  Gly Pro Lys Gly Glu  Lys Gly Asp
    1505                 1510                 1515

Pro Gly  Pro Lys Gly Glu Thr  Gly Pro Thr Gly Pro  Val Gly Pro
    1520                 1525                 1530

Ala Gly  Pro Ala Gly Glu Arg  Gly Glu Gln Gly Pro  Arg Gly Glu
    1535                 1540                 1545

Gln Gly  Ala Thr Gly Pro Ala  Gly Pro Thr Gly Pro  Arg Gly Glu
    1550                 1555                 1560

Pro Gly  Pro Thr Gly Pro Gln  Gly Pro Gln Gly Thr  Pro Gly Thr
    1565                 1570                 1575

Pro Gly  Gln Lys Gly Asp Lys  Gly Asp Pro Gly Gln  Ala Gly Pro
    1580                 1585                 1590

Ala Gly  Pro Arg Gly Pro Ala  Gly Ala Ala Gly Pro  Ala Gly Pro
    1595                 1600                 1605

Ala Gly  Pro Arg Gly Asp Arg  Gly Glu Thr Gly Pro  Ala Gly Pro
    1610                 1615                 1620

Thr Gly  Ala Lys Gly Glu Gln  Gly Gln Lys Gly Asp  Thr Gly Pro
    1625                 1630                 1635

Met Gly  Pro Ala Gly Pro Lys  Gly Asp Ala Gly Pro  Arg Gly Glu
    1640                 1645                 1650

Ala Gly  Pro Ala Gly Ala Thr  Gly Pro Gln Gly Pro  Lys Gly Asp
    1655                 1660                 1665

Asn Gly  Ala Thr Gly Pro Arg  Gly Glu Lys Gly Glu  Pro Gly Pro
    1670                 1675                 1680

Ala Gly  Pro Ile Gly Pro Val  Gly Pro Ala Gly Ala  Ala Gly Pro
    1685                 1690                 1695

Ala Gly  Pro Arg Gly Pro Ala  Gly Ala Ala Gly Pro  Lys Gly Asp
    1700                 1705                 1710

Lys Gly  Asp Thr Gly Gln Lys  Gly Glu Lys Gly Asp  Arg Gly Glu
    1715                 1720                 1725

Lys Gly  Leu Lys Gly Asp Arg  Gly Glu Thr Gly Pro  Arg Gly Glu
    1730                 1735                 1740

Ala Gly  Pro Arg Gly Glu Ala  Gly Pro Ala Gly Ala  Thr Gly Pro
    1745                 1750                 1755

Gln Gly  Pro Lys Gly Asp Asn  Gly Ala Pro Gly Pro  Arg Gly Glu
    1760                 1765                 1770

Lys Gly  Glu Pro Gly Pro Ala  Gly Pro Ile Gly Pro  Val Gly Pro
    1775                 1780                 1785

Ala Gly  Ala Ala Gly Pro Ala  Gly Pro Ala Gly Glu  Arg Gly Pro
    1790                 1795                 1800

Ala Gly  Glu Arg Gly Glu Thr  Gly Pro Ala Gly Pro  Thr Gly Ala
    1805                 1810                 1815

Lys Gly  Glu Gln Gly Pro Glu  Gly Lys Gln Gly Ile  Gln Gly Pro
    1820                 1825                 1830

Ala Gly  Pro Ala Gly Pro Arg  Gly Glu Arg Gly Glu  Thr Gly Pro
    1835                 1840                 1845

Ala Gly  Ala Ala Gly Pro Ala  Gly Pro Ala Gly Ala  Val Gly Pro
    1850                 1855                 1860

Gln Gly  Pro Thr Gly Ala Thr  Gly Pro Ala Gly Pro  Val Gly Pro
    1865                 1870                 1875
```

-continued

```
Arg Gly  Pro Gln Gly Thr Ala  Gly Ala Gln Gly Pro  Lys Gly Glu
    1880                 1885                 1890

Arg Gly  Pro Ala Gly Glu Thr  Gly Pro Lys Gly Glu  Lys Gly Asp
    1895                 1900                 1905

Pro Gly  Pro Lys Gly Glu Thr  Gly Pro Thr Gly Pro  Val Gly Pro
    1910                 1915                 1920

Ala Gly  Pro Ala Gly Glu Arg  Gly Glu Gln Gly Pro  Arg Gly Glu
    1925                 1930                 1935

Gln Gly  Ala Thr Gly Pro Ala  Gly Pro Ala Gly Pro  Arg Gly Pro
    1940                 1945                 1950

Ala Gly  Ala Ala Gly Pro Lys  Gly Asp Lys Gly Asp  Thr Gly Gln
    1955                 1960                 1965

Lys Gly  Glu Thr Gly Pro Ala  Gly Pro Val Gly Pro  Thr Gly Pro
    1970                 1975                 1980

Gln Gly  Ala Pro Gly Pro Ala  Gly Pro Ala Gly Pro  Ala Gly Glu
    1985                 1990                 1995

Arg Gly  Pro Thr Gly Pro Lys  Gly Asp Ala Gly Pro  Lys Gly Asp
    2000                 2005                 2010

Thr Gly  Gln Lys Gly Glu Thr  Gly Pro Ala Gly Pro  Ala Gly Ala
    2015                 2020                 2025

Lys Gly  Glu Pro Gly Pro Arg  Gly Glu Gln Gly Ile  Gln Gly Pro
    2030                 2035                 2040

Thr Gly  Pro Thr Gly Pro Gln  Gly Pro Gln Gly Thr  Ala Gly Ile
    2045                 2050                 2055

Gln Gly  Pro Lys Gly Glu Arg  Gly Asn Val Ser Val  Ser Gly Leu
    2060                 2065                 2070

Pro Ile  Glu Tyr Ala Thr Glu  Asp Gly Lys Ser Ile  Ile Asn Met
    2075                 2080                 2085

Gly Gly  Asn Phe Tyr Leu Glu  Glu Pro Ala Lys Asp  Gly Ser Ile
    2090                 2095                 2100

Lys Leu  Ile Pro Val Val Asn  Val Lys Gly Lys Phe  Ser Thr Lys
    2105                 2110                 2115

Thr Gln  Asn Pro Asp Gly Ser  Ile Thr Leu Lys Ser  Leu Ala Val
    2120                 2125                 2130

Lys Val  Asn Leu Ala Asn Glu  Thr Pro Met Val Leu  Gly Asn Val
    2135                 2140                 2145

Ala Glu  Gly Val Ala Asp Thr  Asp Ala Val Asn Val  Lys Gln Leu
    2150                 2155                 2160

Lys Ser  Ala Lys Thr Glu Val  Glu Ser Thr Asp His  Ser Val Val
    2165                 2170                 2175

Ile Lys  Glu Arg Gln Gly Asp  Asn Gln Gln Ile Val  Tyr Asp Leu
    2180                 2185                 2190

Ala Val  Ala Lys Thr Lys Leu  Thr Ala Ser Lys Asp  Lys Arg Thr
    2195                 2200                 2205

Ile Ser  Ala Ala Asp Lys Gly  Asn His Phe Ala Thr  Gly Asp Glu
    2210                 2215                 2220

Val Ala  Val Ala Ile Asn Thr  Ala Thr Ala Ala Ala  Arg Thr Glu
    2225                 2230                 2235

Val Glu  Ala Gly Lys Asn Val  Lys Val Thr Ser Lys  Thr Gly Ala
    2240                 2245                 2250

Asn Gly  Gln Asn Ile Tyr Asn  Val Ser Val Phe Gly  Asp Leu Ser
    2255                 2260                 2265

Asp Ile  Thr Ser Ile Ser Asn  Gly Asp Thr Lys Val  Ser Leu Gly
```

-continued

```
    2270                2275                2280

Lys Asp  Lys Gln Gly Asn Pro  Val Val Asn Met Asn  Gly Ala Arg
    2285                2290                2295

Ile Thr  Asn Val Gly Asp Gly  Ser Ala Glu Gly Asp  Ile Val Asn
    2300                2305                2310

Val Arg  Gln Leu Asn Lys Val  Val Ser Ser Val Asn  Thr Gly Phe
    2315                2320                2325

Asn Gln  Leu Ser Arg Asp Ile  Val Asn Ala Arg Ala  Gly Ile Ala
    2330                2335                2340

Ser Ala  Gly Ala Met Ala Asn  Leu Pro Gln Ile Ser  Leu Pro Gly
    2345                2350                2355

Lys Ser  Ala Ile Ser Val Ser  Asn Ala Gln Tyr Arg  Gly Gln Ser
    2360                2365                2370

Ala Tyr  Ala Ile Gly Tyr Ser  Lys Ile Ser Asp Asn  Gly Lys Trp
    2375                2380                2385

Leu Ile  Arg Ala Ser Val Ser  Ser Asn Thr Gln Arg  Asp Thr Met
    2390                2395                2400

Ile Gly  Gly Gly Val Gly Phe  Val Trp
    2405                2410
```

<210> SEQ ID NO 9
<211> LENGTH: 3024
<212> TYPE: DNA
<213> ORGANISM: Haemophilus parasuis

<400> SEQUENCE: 9

```
atgaataaaa tatttagagt tatttggagt catgctcaac aggcttgggt ggttgtatct     60
gagttagtaa agtctcatac taaaacatcc gcttacacgg ataaaagagc tcaagtatgc    120
acctcagatt attttttaga taaacagcaa gataaattta aattaagttt tttaagtcta    180
gtattactag gtatattttt tagtccagta ggttcagcaa ggctttttct agatgaggct    240
cgtcaaggga gtgcaggagt tgacgatggt tctattggta ttggtagaga gagtaaggtt    300
gggcctggtt ctattactat tggtcagaaa tcagaagctg aaggtaggac tgctgttgcg    360
ataggttatt cagcaaagac aggttcagag cacgacaacg ctattgcgat aggcaacagc    420
tctaaagcaa ctgggcctgg aacagttacc gtggggcata gttcacaagc gaaagatagg    480
tctgttgtct taggcgcaaa cgccgagggg aaaaatgctc aaacagttgt aataggtacc    540
cttgctaaag caagtgcgtc acaatctatt gctattgggg cagataccaa agcggagggg    600
tatggctcca tatcaatcgg tggagatgat ttagatcaaa cgaaatataa cgataataat    660
agtacaaacc aaccccgcca cacaacaact gcgaaaggta aggcctctgt tgctattggg    720
ggtctgtctt tggctgaggg cgacggatct attgttgtag gtcctttagc atctgcaagt    780
gatgttgaag gcattgctat cggtgcgaga agtaagtcta ccaatgagta cggtattgcg    840
gttggtggtg gtgcaactgc tggaaaaaac gccgttgctc ttggtaggga gtcgaaaggt    900
gctgggacag attccattgc gataggtaat tctgcgagaa caacaggggc agactctgtt    960
gttgtgggtg ccaatatcga tgtgacagat gaaaaattag tggccattgg ataccaagca   1020
agtgctaaaa gtcatgctac tgccttgggt tatatggcct ctgccggtgg tatgcactct   1080
gttgctgtgg gtgaaagtgc catgacaaat gatggtgctg ctagagcaac cgcacttggt   1140
aataataccg ttgtcaccgt gggtggcggt gtggcattgg gttatggatc aagagcagaa   1200
acgagagggg gtattgaagg ggcaaaacag tcttattctg taacaacagg gacaagcagt   1260
gttgataacg gctttaaatc tacaggaagt gttgataaca attctattcc tattggtgcg   1320
```

-continued gtttctgtgg gtaataacaa aatcaaacgt caaatcgtca atgtggcggc aggtaaagaa 1380
ttaaccgatg cagtaaacgt ggcacagctt aaatctttaa ccctgaaaat tgcaggcaat 1440
accagcgaac aaacacaacc agcggttggc ttatgggaag gtacgctgaa agtaatgggt 1500
acaagcggtg agattaagac ttccgcaagc ggtgatacca tcacattgaa attagatgaa 1560
acattgaaaa ataaaattaa tacgattgac aatttaggtt ggaacctgaa gattgcgaaa 1620
ggggctggtg aagcaaatcc acctaatgca gcacatctta tcaaaatgag cgatacggca 1680
accgtaacct ttaccgctgg aaataatatt aaattagaac aaacgaacgg aaatattacg 1740
atttctacga ttggtaagtt aattgcaaag actgaatggg aaaatgatgg tttgaaaatt 1800
acttatacgg atggtatgca tgacattatc aagaaaggtg aaaaaggaga tcgtggtgag 1860
cgaggtctaa gaggtgaaac aggccctgcg ggtccagcgg gtcctatggg tccagcaggg 1920
gctgctggtc tagtaggacc aatgggccct caaggtcctg cgggtccacc tggtcctgtg 1980
ggtccagcag gggctgctgg tcctaagggg gataaaggcg aaccaggaca agcgggtcca 2040
actggaccac gaggccctgc gggtcctaaa ggagatgcag gtccaaaagg tgatacaggt 2100
cagagaggtg aaactggccc tgcgggtcca gcgggaccac aaggtcctgc gggtccaacg 2160
gggcctaggg gtgacaaagg tgatacgggt ccagcaggac cacaaggccc tgcgggtcca 2220
acgggaccac aaggccctgc gggtccaacg ggatcacaag accctgcggg tccaactgga 2280
aattcggaat taaaaggcat tacctcgatt gccaatggta acgacgccac caaggcgaat 2340
ggggctaaga ttaccttgtc tgcaggttct acagataaaa cagttaatgt taatgatgcg 2400
aaaattacca atgtggcggc tggtacagca gatactgatg cggtgaatgt gagccagtta 2460
aatactaagg cagcagcggc gagaactgag gttgaagcgg gtaaaaatgt gaaagtgact 2520
tcaaaaacgg gggcaaatgg tcagaatatt tacaatgtga gcgtgtctgg agatttaagc 2580
gacattactt caattagtaa tggcgatacg aaagtatctt taggtaaaga taagcaagga 2640
aatccagttg taaatatgaa tggtgccaga attaccaacg ttggagatgg tagtgctgag 2700
ggcgatattg tgaatgttcg tcagctcaac aaagtggttt cttctgtgaa tacaggattt 2760
aatcaattat caagagatat tggtcgtgtt gatgttaatg caagagcggg gattgcttct 2820
gctggggcga tggctaattt gccacaaatt tctttaccag gtaaaagtgc tatttctgtt 2880
tctaatgcac aatatcgcgg gcaatctgcc tatgctatag gttattccag aatttctgat 2940
aatggcaaat ggcttattcg agcgtctgtt agcagtaata ctcagcggga tactatgatt 3000
ggaggagggg taggttttgt gtgg 3024

<210> SEQ ID NO 10
<211> LENGTH: 1008
<212> TYPE: PRT
<213> ORGANISM: haemophilus parasuis

<400> SEQUENCE: 10

Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Phe Leu Ser Leu Val Leu Leu Gly
    50                  55                  60

Ile Phe Phe Ser Pro Val Gly Ser Ala Arg Leu Phe Leu Asp Glu Ala

-continued

```
65                  70                  75                  80

Arg Gln Gly Ser Ala Gly Val Asp Asp Gly Ser Ile Gly Ile Gly Arg
                85                  90                  95

Glu Ser Lys Val Gly Pro Gly Ser Ile Thr Ile Gly Gln Lys Ser Glu
            100                 105                 110

Ala Glu Gly Arg Thr Ala Val Ala Ile Gly Tyr Ser Ala Lys Thr Gly
        115                 120                 125

Ser Glu His Asp Asn Ala Ile Ala Ile Gly Asn Ser Ser Lys Ala Thr
    130                 135                 140

Gly Pro Gly Thr Val Thr Val Gly His Ser Ser Gln Ala Lys Asp Arg
145                 150                 155                 160

Ser Val Val Leu Gly Ala Asn Ala Glu Gly Lys Asn Ala Gln Thr Val
                165                 170                 175

Val Ile Gly Thr Leu Ala Lys Ala Ser Ala Ser Gln Ser Ile Ala Ile
            180                 185                 190

Gly Ala Asp Thr Lys Ala Glu Gly Tyr Gly Ser Ile Ser Ile Gly Gly
        195                 200                 205

Asp Asp Leu Asp Gln Thr Lys Tyr Asn Asp Asn Asn Ser Thr Asn Gln
    210                 215                 220

Pro Arg His Thr Thr Thr Ala Lys Gly Lys Ala Ser Val Ala Ile Gly
225                 230                 235                 240

Gly Leu Ser Leu Ala Glu Gly Asp Gly Ser Ile Val Val Gly Pro Leu
                245                 250                 255

Ala Ser Ala Ser Asp Val Glu Gly Ile Ala Ile Gly Ala Arg Ser Lys
            260                 265                 270

Ser Thr Asn Glu Tyr Gly Ile Ala Val Gly Gly Gly Ala Thr Ala Gly
        275                 280                 285

Lys Asn Ala Val Ala Leu Gly Arg Glu Ser Lys Gly Ala Gly Thr Asp
    290                 295                 300

Ser Ile Ala Ile Gly Asn Ser Ala Arg Thr Thr Gly Ala Asp Ser Val
305                 310                 315                 320

Val Val Gly Ala Asn Ile Asp Val Thr Asp Glu Lys Leu Val Ala Ile
                325                 330                 335

Gly Tyr Gln Ala Ser Ala Lys Ser His Ala Thr Ala Leu Gly Tyr Met
            340                 345                 350

Ala Ser Ala Gly Gly Met His Ser Val Ala Val Gly Glu Ser Ala Met
        355                 360                 365

Thr Asn Asp Gly Ala Ala Arg Ala Thr Ala Leu Gly Asn Asn Thr Val
    370                 375                 380

Val Thr Val Gly Gly Gly Val Ala Leu Gly Tyr Gly Ser Arg Ala Glu
385                 390                 395                 400

Thr Arg Gly Gly Ile Glu Gly Ala Lys Gln Ser Tyr Ser Val Thr Thr
                405                 410                 415

Gly Thr Ser Ser Val Asp Asn Gly Phe Lys Ser Thr Gly Ser Val Asp
            420                 425                 430

Asn Asn Ser Ile Pro Ile Gly Ala Val Ser Val Gly Asn Asn Lys Ile
        435                 440                 445

Lys Arg Gln Ile Val Asn Val Ala Ala Gly Lys Glu Leu Thr Asp Ala
    450                 455                 460

Val Asn Val Ala Gln Leu Lys Ser Leu Thr Leu Lys Ile Ala Gly Asn
465                 470                 475                 480

Thr Ser Glu Gln Thr Gln Pro Ala Val Gly Leu Trp Glu Gly Thr Leu
                485                 490                 495
```

-continued

```
Lys Val Met Gly Thr Ser Gly Glu Ile Lys Thr Ser Ala Ser Gly Asp
            500                 505                 510

Thr Ile Thr Leu Lys Leu Asp Glu Thr Leu Lys Asn Lys Ile Asn Thr
        515                 520                 525

Ile Asp Asn Leu Gly Trp Asn Leu Lys Ile Ala Lys Gly Ala Gly Glu
    530                 535                 540

Ala Asn Pro Pro Asn Ala Ala His Leu Ile Lys Met Ser Asp Thr Ala
545                 550                 555                 560

Thr Val Thr Phe Thr Ala Gly Asn Asn Ile Lys Leu Glu Gln Thr Asn
                565                 570                 575

Gly Asn Ile Thr Ile Ser Thr Ile Gly Lys Leu Ile Ala Lys Thr Glu
            580                 585                 590

Trp Glu Asn Asp Gly Leu Lys Ile Thr Tyr Thr Asp Gly Met His Asp
        595                 600                 605

Ile Ile Lys Lys Gly Glu Lys Gly Asp Arg Gly Glu Arg Gly Leu Arg
    610                 615                 620

Gly Glu Thr Gly Pro Ala Gly Pro Ala Gly Pro Met Gly Pro Ala Gly
625                 630                 635                 640

Ala Ala Gly Leu Val Gly Pro Met Gly Pro Gln Gly Pro Ala Gly Pro
                645                 650                 655

Pro Gly Pro Val Gly Pro Ala Gly Ala Ala Gly Pro Lys Gly Asp Lys
            660                 665                 670

Gly Glu Pro Gly Gln Ala Gly Pro Thr Gly Pro Arg Gly Pro Ala Gly
        675                 680                 685

Pro Lys Gly Asp Ala Gly Pro Lys Gly Asp Thr Gly Gln Arg Gly Glu
    690                 695                 700

Thr Gly Pro Ala Gly Pro Ala Gly Pro Gln Gly Pro Ala Gly Pro Thr
705                 710                 715                 720

Gly Pro Arg Gly Asp Lys Gly Asp Thr Gly Pro Ala Gly Pro Gln Gly
                725                 730                 735

Pro Ala Gly Pro Thr Gly Pro Gln Gly Pro Ala Gly Pro Thr Gly Ser
            740                 745                 750

Gln Asp Pro Ala Gly Pro Thr Gly Asn Ser Glu Leu Lys Gly Ile Thr
        755                 760                 765

Ser Ile Ala Asn Gly Asn Asp Ala Thr Lys Ala Asn Gly Ala Lys Ile
    770                 775                 780

Thr Leu Ser Ala Gly Ser Thr Asp Lys Thr Val Asn Val Asn Asp Ala
785                 790                 795                 800

Lys Ile Thr Asn Val Ala Ala Gly Thr Ala Asp Thr Asp Ala Val Asn
                805                 810                 815

Val Ser Gln Leu Asn Thr Lys Ala Ala Ala Ala Arg Thr Glu Val Glu
            820                 825                 830

Ala Gly Lys Asn Val Lys Val Thr Ser Lys Thr Gly Ala Asn Gly Gln
        835                 840                 845

Asn Ile Tyr Asn Val Ser Val Ser Gly Asp Leu Ser Asp Ile Thr Ser
    850                 855                 860

Ile Ser Asn Gly Asp Thr Lys Val Ser Leu Gly Lys Asp Lys Gln Gly
865                 870                 875                 880

Asn Pro Val Val Asn Met Asn Gly Ala Arg Ile Thr Asn Val Gly Asp
                885                 890                 895

Gly Ser Ala Glu Gly Asp Ile Val Asn Val Arg Gln Leu Asn Lys Val
            900                 905                 910

Val Ser Ser Val Asn Thr Gly Phe Asn Gln Leu Ser Arg Asp Ile Gly
        915                 920                 925
```

```
Arg Val Asp Val Asn Ala Arg Ala Gly Ile Ala Ser Ala Gly Ala Met
    930                 935                 940

Ala Asn Leu Pro Gln Ile Ser Leu Pro Gly Lys Ser Ala Ile Ser Val
945                 950                 955                 960

Ser Asn Ala Gln Tyr Arg Gly Gln Ser Ala Tyr Ala Ile Gly Tyr Ser
                965                 970                 975

Arg Ile Ser Asp Asn Gly Lys Trp Leu Ile Arg Ala Ser Val Ser Ser
            980                 985                 990

Asn Thr Gln Arg Asp Thr Met Ile  Gly Gly Gly Val Gly  Phe Val Trp
        995                 1000                 1005


<210> SEQ ID NO 11
<211> LENGTH: 4944
<212> TYPE: DNA
<213> ORGANISM: Haemophilus parasuis

<400> SEQUENCE: 11

atgaataaaa tatttagagt tatttggagt catgctcaac aggcttgggt ggttgtatct     60

gagttagtaa agtctcatac caaaacatcc gcttacacgg ataaaagagc tcaagtatgc    120

acctcagatt attttttag taaacagcaa gataaattta aattaagtct tttaagtcta    180

gtattactag gtatattttt tagttcagta ggttcagctg catatcttga atatggtgct    240

cgagcagtga atagtggaag ccgcggttct attggtattg gtatagggag tacggttggg    300

tatgcttcta ttggtattgg tgacaacgca aacgctagag gtgaggttgc tgttgcgata    360

ggttatggag ctcaatcaat caataacgat gccacagccg ttgggagagc ttcacaagca    420

ggctatcgtt ctgcggctta tggttttgat gcaaaagcac aaggagaagg ctctgttgcg    480

ataggcaacc aggctacagt aaatgggaat gctagagcaa ttgccatcgg tcagcagtca    540

aaagctgaag gtcagaatgt tattgcgata ggttatttag caaaggcagg attagctggc    600

tctgttgtga tgggcaacaa tgctacgtgg gtagaagggg aaaatttacg tcagtattca    660

acaaagggaa gagggaacga tactgttatt atcggtgcta atgcgaaagc agcacatagt    720

tcgactgcat taggtagttc agctgaagca aaagcatttt ctgcaacagc actaggaaga    780

ttggctaaag ctaaaggaga gttctctatt gctatagggg ggggagacag tgacaatagt    840

acagctatag caaatgggta tgcagcaatt gccgtgggga gaggttcaag agcgggagag    900

gaatctattg ccttaggcag agatgccgat gcgacaacta ctcaaacagt tgtaataggt    960

ctacaggcta gtgcaagtaa gtcacactct gttgttatcg gtgcgaatag taactctacc   1020

gctaattacg gtattgcggt tggtggtggt gcaaatgctg ctggaggcaa cgccgttgct   1080

cttggtaggg agtcgaaagg tgctgggaca gattccattg cgataggtta ttctgcgaaa   1140

acaacagggg cagactctgt tgttgtcggt gccaatatca atgtgacaga tggacaatta   1200

gtggcagttg gataccaagc aagtgctaaa agtcattcta ctgccttggg ttataaagcc   1260

tctgccggtg gtaggggctc tgttgctgtg ggtgaagagg caaagacaac accagacaga   1320

tcaaccgcac ttggtaataa taccgttgtc agcgtgggtg gcggtgtggc attaggttat   1380

ggatctaatg caaatacagc tggcggtgta gaggggttaa aacaaactca ttcagttgtt   1440

actgatgaga aatcggaagc taatggcttt aaatcaacag aaaaggttag taataatgct   1500

attggtgcgg tttctgtggg taatgacaac atcaaacgcc aaatcgtcaa tgtggcggct   1560

ggtacacaag ataccgatgc agtaaacgtg gcacagctta aatctttaac catgaaaatt   1620

gcagggaata ccaacgaaca accacaacca gcggttgact tgtggagtgg tacgctcact   1680
```

-continued

```
gtaaaaggag aaaatggtat tacttcctct gctaatggca gtacgattac agttagatta   1740
gagcaacaac tcaaagataa aattgatacg attgccgcta tgggtaagtt aattaaaagt   1800
gcggaaaatg aatcaaatgg cgatctaaaa attacctata cagataattc gtttagcatt   1860
atcaagaaag gtgaaaaagg agatcgtggt gaaaaaggag atcgtggcga aactggccct   1920
gcgggtccag caggtccaat gggtcctagg ggtgagcgag gagaagctgg ccctgcgggt   1980
gcagctggtc cagcaggggc taggggtgaa gctggtccag tgggtccaga aggaccgcga   2040
ggacctgcgg gtccaaccgg tgctcaaggt ccagcagggc ctaggggtga acagggtcta   2100
aaaggagata caggtccagc gggagagcca ggcaagcagg gtcctagggg agagaaaggt   2160
gaaattggtc ctgcaggtcc aaaaggagag gcaggagcaa aaggcgataa gggtgacact   2220
ggtgaagcag gaccaatagg ccctcaaggt cctgcaggtg cagctggacc taagggtgaa   2280
cagggtccta aaggtgaaca aggtattcag ggacctaagg gtgacaaagg tgataccggt   2340
cagaaaggtg aaacaggccc tgcgggtcca gtaggtccag ctggaccaca aggtgtacct   2400
ggtcctgcag gtccaaaagg agaggcagga ccagtgggcc ctcaaggtcc tgcgggtgca   2460
actggtccta aggggataa aggcgatcca ggacaagcgg gtcctaaagg agatacaggt   2520
ccaaaaggcg atagaggcga agctggtcca atggggcctg ctggtccaaa aggagaaact   2580
ggctctgcgg gcccagcagg tgctgacggt acaagcattg ttcagaaaga tgcagaaggt   2640
aatgacttaa caacaaccgt taaagcagat ggcgtaacgg caacggataa agactctaaa   2700
aatactgtca atgcagatgg tatgactgtt ggtccgaaag acgaaaatca aacggataaa   2760
tcagctgcga cttataacag agatggtgta acggttaaag gaaatgacgg tgcagatgca   2820
attgtcttaa ctagcaaaga aggtcaagat ggtaaaacaa ctaacacctt ggcacttaaa   2880
ggccaaaatg gcaaagatgc agtaagcatt acttcggggg cagatggcac agcaccagaa   2940
attagctttg ctaaaaatgg tgagggtacg gatgctaaag gcacgggctc tatcactggc   3000
ttaaaagatg ttgaacgtaa tccagacggc acggcgaaag acagaacggc tgcagcgaat   3060
gcgggttatg tcgatgatcg cttaaaagaa atgaacgatc gaaaaccgtt tgagtacttt   3120
gagaaagatt ctgtaacagg cgaagtaaaa actgaaactg taaatggtaa acaagtacca   3180
gttacgcttg ttcgcggaaa agatggtaaa ttctataaag agagtgactt aaaagggaaa   3240
gttttcgatc ctgcaacaaa tacatataaa aatgcagatg gtacacctgc aacattaact   3300
gaggttgctt caaataatgt tactgttcaa gcaatgccat cggatgcaag caatacacca   3360
attgcgatga gcaatgtggg aagtggttta ggtttgaaag atgatgctga atcaaataaa   3420
acggcactta cccctacaga tgcacaaaaa gctattgctg gtgataacaa agacggtaaa   3480
ggcggcttat tggctcaaac gggtaatgcg ttaaataatg tagcgacagt gaaagattta   3540
caagccattg cacaagcggg cttagacttg acgggtaaca acgccgatac cactgtacat   3600
cgtccattgg gtacgaagtt aaccgttgag ggtgaaggca aatggaatgg taaggactca   3660
gcggctaata acctttatgt ggaagcgcaa gaggcagata acaaacttgt tgtgaaaatg   3720
aacagggatt taacgaactt aaattctgtg actttaggca ctgcgacaat gactggtgat   3780
aagaatacaa tcaaccttac tggtgcagga gagaaagtcg aggaagagtt tgttaaatgg   3840
gacccagtga ctaaacaacc tattcttgat gagaatggca atctccagaa atataaagag   3900
aaagttgatc ctcgtgtgaa actgagtggt attgctgatg gtgatatttc accaaatagt   3960
actgatgcag tgaatggtcg ccaagtttat gttttaaccg atcgtatcag gttcttccac   4020
accaatgatg gtcataatgc agaggagcaa attaaccata agtcgaatac agtggactct   4080
```

-continued cgtgcaacag gttcatactc tactgcagtt ggctacaaag ctcacgcgaa aggggagagt 4140
tctgttgctt taggtaacgg ggctacagct ggagagcaag gcgtggctat tggtcacggt 4200
gctgtggcgt caggtaaaca atctatttcg attggtaccg gcaatgtggt gagtggtaat 4260
aactcaggtg ctattggtga ccctaataca attaaagcag atcgctctta tgcattaggt 4320
aataataacc aagtgaatgc aggtcaatct gatgtgtttg ttgtcggtaa caacgtgaaa 4380
aacacaacca gcaactcggt attcttggga acaaactcag gctatgtggc agcaggtgca 4440
accactgcgg gggcgggtgc tttagaaagc caagtaatag gtggtgtgta taacgcttac 4500
gcaggtggca aagctactga agtgaaaggc gtggtgagcg tgggtaatgt agacagtaat 4560
ggcaaaatgg aaactcgccg tattcaaaac gttgcaccag gtttaatctc tgagcaaagt 4620
accgatgcga ttaatggtag ccagttgtat agcttaatat ctcagcacaa ggtgcatatg 4680
ggcgatattc acaataagat caaccgtaat aataaagctc tgcgtgcggg tattgcaggt 4740
tctaacgccg cagcaggttt accacaggtt tatctcccag gtaagtcaat gattgcagca 4800
tcagcgggga ctttcaaagg tcaatctgca ttggctgtgg gttactcaag agcatcagat 4860
aacggcaagc tgatccttaa attacaaggt aatgcaaata ctagtggtga aatgggcggc 4920
tctgtggggg taggttatca gtgg 4944

<210> SEQ ID NO 12
<211> LENGTH: 1648
<212> TYPE: PRT
<213> ORGANISM: haemophilus parasuis

<400> SEQUENCE: 12

Met Asn Lys Ile Phe Arg Val Ile Trp Ser His Ala Gln Gln Ala Trp
1 5 10 15

Val Val Val Ser Glu Leu Val Lys Ser His Thr Lys Thr Ser Ala Tyr
20 25 30

Thr Asp Lys Arg Ala Gln Val Cys Thr Ser Asp Tyr Phe Phe Ser Lys
35 40 45

Gln Gln Asp Lys Phe Lys Leu Ser Leu Leu Ser Leu Val Leu Leu Gly
50 55 60

Ile Phe Phe Ser Ser Val Gly Ser Ala Ala Tyr Leu Glu Tyr Gly Ala
65 70 75 80

Arg Ala Val Asn Ser Gly Ser Arg Gly Ser Ile Gly Ile Gly Ile Gly
85 90 95

Ser Thr Val Gly Tyr Ala Ser Ile Gly Ile Gly Asp Asn Ala Asn Ala
100 105 110

Arg Gly Glu Val Ala Val Ala Ile Gly Tyr Gly Ala Gln Ser Ile Asn
115 120 125

Asn Asp Ala Thr Ala Val Gly Arg Ala Ser Gln Ala Gly Tyr Arg Ser
130 135 140

Ala Ala Tyr Gly Phe Asp Ala Lys Ala Gln Gly Glu Gly Ser Val Ala
145 150 155 160

Ile Gly Asn Gln Ala Thr Val Asn Gly Asn Ala Arg Ala Ile Ala Ile
165 170 175

Gly Gln Gln Ser Lys Ala Glu Gly Gln Asn Val Ile Ala Ile Gly Tyr
180 185 190

Leu Ala Lys Ala Gly Leu Ala Gly Ser Val Val Met Gly Asn Asn Ala
195 200 205

Thr Trp Val Glu Gly Glu Asn Leu Arg Gln Tyr Ser Thr Lys Gly Arg
210 215 220

```
Gly Asn Asp Thr Val Ile Ile Gly Ala Asn Ala Lys Ala Ala His Ser
225                 230                 235                 240

Ser Thr Ala Leu Gly Ser Ser Ala Glu Ala Lys Ala Phe Ser Ala Thr
                245                 250                 255

Ala Leu Gly Arg Leu Ala Lys Ala Lys Gly Glu Phe Ser Ile Ala Ile
            260                 265                 270

Gly Gly Gly Asp Ser Asp Asn Ser Thr Ala Ile Ala Asn Gly Tyr Ala
        275                 280                 285

Ala Ile Ala Val Gly Arg Gly Ser Arg Ala Gly Glu Glu Ser Ile Ala
    290                 295                 300

Leu Gly Arg Asp Ala Asp Ala Thr Thr Thr Gln Thr Val Val Ile Gly
305                 310                 315                 320

Leu Gln Ala Ser Ala Ser Lys Ser His Ser Val Val Ile Gly Ala Asn
                325                 330                 335

Ser Asn Ser Thr Ala Asn Tyr Gly Ile Ala Val Gly Gly Gly Ala Asn
            340                 345                 350

Ala Ala Gly Gly Asn Ala Val Ala Leu Gly Arg Glu Ser Lys Gly Ala
        355                 360                 365

Gly Thr Asp Ser Ile Ala Ile Gly Tyr Ser Ala Lys Thr Thr Gly Ala
    370                 375                 380

Asp Ser Val Val Val Gly Ala Asn Ile Asn Val Thr Asp Gly Gln Leu
385                 390                 395                 400

Val Ala Val Gly Tyr Gln Ala Ser Ala Lys Ser His Ser Thr Ala Leu
                405                 410                 415

Gly Tyr Lys Ala Ser Ala Gly Gly Arg Gly Ser Val Ala Val Gly Glu
            420                 425                 430

Glu Ala Lys Thr Thr Pro Asp Arg Ser Thr Ala Leu Gly Asn Asn Thr
        435                 440                 445

Val Val Ser Val Gly Gly Gly Val Ala Leu Gly Tyr Gly Ser Asn Ala
    450                 455                 460

Asn Thr Ala Gly Gly Val Glu Gly Leu Lys Gln Thr His Ser Val Val
465                 470                 475                 480

Thr Asp Glu Lys Ser Glu Ala Asn Gly Phe Lys Ser Thr Glu Lys Val
                485                 490                 495

Ser Asn Asn Ala Ile Gly Ala Val Ser Val Gly Asn Asp Asn Ile Lys
            500                 505                 510

Arg Gln Ile Val Asn Val Ala Ala Gly Thr Gln Asp Thr Asp Ala Val
        515                 520                 525

Asn Val Ala Gln Leu Lys Ser Leu Thr Met Lys Ile Ala Gly Asn Thr
    530                 535                 540

Asn Glu Gln Pro Gln Pro Ala Val Asp Leu Trp Ser Gly Thr Leu Thr
545                 550                 555                 560

Val Lys Gly Glu Asn Gly Ile Thr Ser Ser Ala Asn Gly Ser Thr Ile
                565                 570                 575

Thr Val Arg Leu Glu Gln Gln Leu Lys Asp Lys Ile Asp Thr Ile Ala
            580                 585                 590

Ala Met Gly Lys Leu Ile Lys Ser Ala Glu Asn Glu Ser Asn Gly Asp
        595                 600                 605

Leu Lys Ile Thr Tyr Thr Asp Asn Ser Phe Ser Ile Ile Lys Lys Gly
    610                 615                 620

Glu Lys Gly Asp Arg Gly Glu Lys Gly Asp Arg Gly Glu Thr Gly Pro
625                 630                 635                 640

Ala Gly Pro Ala Gly Pro Met Gly Pro Arg Gly Glu Arg Gly Glu Ala
                645                 650                 655
```

```
Gly Pro Ala Gly Ala Ala Gly Pro Ala Gly Ala Arg Gly Glu Ala Gly
            660                 665                 670

Pro Val Gly Pro Glu Gly Pro Arg Gly Pro Ala Gly Pro Thr Gly Ala
        675                 680                 685

Gln Gly Pro Ala Gly Pro Arg Gly Glu Gln Gly Leu Lys Gly Asp Thr
    690                 695                 700

Gly Pro Ala Gly Glu Pro Gly Lys Gln Gly Pro Arg Gly Glu Lys Gly
705                 710                 715                 720

Glu Ile Gly Pro Ala Gly Pro Lys Gly Glu Ala Gly Ala Lys Gly Asp
                725                 730                 735

Lys Gly Asp Thr Gly Glu Ala Gly Pro Ile Gly Pro Gln Gly Pro Ala
            740                 745                 750

Gly Ala Ala Gly Pro Lys Gly Glu Gln Gly Pro Lys Gly Glu Gln Gly
        755                 760                 765

Ile Gln Gly Pro Lys Gly Asp Lys Gly Asp Thr Gly Gln Lys Gly Glu
    770                 775                 780

Thr Gly Pro Ala Gly Pro Val Gly Pro Ala Gly Pro Gln Gly Val Pro
785                 790                 795                 800

Gly Pro Ala Gly Pro Lys Gly Glu Ala Gly Pro Val Gly Pro Gln Gly
                805                 810                 815

Pro Ala Gly Ala Thr Gly Pro Lys Gly Asp Lys Gly Asp Pro Gly Gln
            820                 825                 830

Ala Gly Pro Lys Gly Asp Thr Gly Pro Lys Gly Asp Arg Gly Glu Ala
        835                 840                 845

Gly Pro Met Gly Pro Ala Gly Pro Lys Gly Glu Thr Gly Ser Ala Gly
    850                 855                 860

Pro Ala Gly Ala Asp Gly Thr Ser Ile Val Gln Lys Asp Ala Glu Gly
865                 870                 875                 880

Asn Asp Leu Thr Thr Thr Val Lys Ala Asp Gly Val Thr Ala Thr Asp
                885                 890                 895

Lys Asp Ser Lys Asn Thr Val Asn Ala Asp Gly Met Thr Val Gly Pro
            900                 905                 910

Lys Asp Glu Asn Gln Thr Asp Lys Ser Ala Ala Thr Tyr Asn Arg Asp
        915                 920                 925

Gly Val Thr Val Lys Gly Asn Asp Gly Ala Asp Ala Ile Val Leu Thr
    930                 935                 940

Ser Lys Glu Gly Gln Asp Gly Lys Thr Thr Asn Thr Leu Ala Leu Lys
945                 950                 955                 960

Gly Gln Asn Gly Lys Asp Ala Val Ser Ile Thr Ser Gly Ala Asp Gly
                965                 970                 975

Thr Ala Pro Glu Ile Ser Phe Ala Lys Asn Gly Glu Gly Thr Asp Ala
            980                 985                 990

Lys Gly Thr Gly Ser Ile Thr Gly  Leu Lys Asp Val Glu  Arg Asn Pro
        995                 1000                1005

Asp Gly  Thr Ala Lys Asp Arg  Thr Ala Ala Ala Asn  Ala Gly Tyr
    1010                1015                1020

Val Asp  Asp Arg Leu Lys Glu  Met Asn Asp Arg Lys  Pro Phe Glu
    1025                1030                1035

Tyr Phe  Glu Lys Asp Ser Val  Thr Gly Glu Val Lys  Thr Glu Thr
    1040                1045                1050

Val Asn  Gly Lys Gln Val Pro  Val Thr Leu Val Arg  Gly Lys Asp
    1055                1060                1065

Gly Lys  Phe Tyr Lys Glu Ser  Asp Leu Lys Gly Lys  Val Phe Asp
```

-continued

```
    1070                1075                1080

Pro Ala  Thr Asn Thr Tyr Lys  Asn Ala Asp Gly Thr  Pro Ala Thr
    1085                1090                1095

Leu Thr  Glu Val Ala Ser Asn  Asn Val Thr Val Gln  Ala Met Pro
    1100                1105                1110

Ser Asp  Ala Ser Asn Thr Pro  Ile Ala Met Ser Asn  Val Gly Ser
    1115                1120                1125

Gly Leu  Gly Leu Lys Asp Asp  Ala Glu Ser Asn Lys  Thr Ala Leu
    1130                1135                1140

Thr Pro  Thr Asp Ala Gln Lys  Ala Ile Ala Gly Asp  Asn Lys Asp
    1145                1150                1155

Gly Lys  Gly Gly Leu Leu Ala  Gln Thr Gly Asn Ala  Leu Asn Asn
    1160                1165                1170

Val Ala  Thr Val Lys Asp Leu  Gln Ala Ile Ala Gln  Ala Gly Leu
    1175                1180                1185

Asp Leu  Thr Gly Asn Asn Ala  Asp Thr Thr Val His  Arg Pro Leu
    1190                1195                1200

Gly Thr  Lys Leu Thr Val Glu  Gly Glu Gly Lys Trp  Asn Gly Lys
    1205                1210                1215

Asp Ser  Ala Ala Asn Asn Leu  Tyr Val Glu Ala Gln  Glu Ala Asp
    1220                1225                1230

Asn Lys  Leu Val Val Lys Met  Asn Arg Asp Leu Thr  Asn Leu Asn
    1235                1240                1245

Ser Val  Thr Leu Gly Thr Ala  Thr Met Thr Gly Asp  Lys Asn Thr
    1250                1255                1260

Ile Asn  Leu Thr Gly Ala Gly  Glu Lys Val Glu Glu  Glu Phe Val
    1265                1270                1275

Lys Trp  Asp Pro Val Thr Lys  Gln Pro Ile Leu Asp  Glu Asn Gly
    1280                1285                1290

Asn Leu  Gln Lys Tyr Lys Glu  Lys Val Asp Pro Arg  Val Lys Leu
    1295                1300                1305

Ser Gly  Ile Ala Asp Gly Asp  Ile Ser Pro Asn Ser  Thr Asp Ala
    1310                1315                1320

Val Asn  Gly Arg Gln Val Tyr  Val Leu Thr Asp Arg  Ile Arg Phe
    1325                1330                1335

Phe His  Thr Asn Asp Gly His  Asn Ala Glu Glu Gln  Ile Asn His
    1340                1345                1350

Lys Ser  Asn Thr Val Asp Ser  Arg Ala Thr Gly Ser  Tyr Ser Thr
    1355                1360                1365

Ala Val  Gly Tyr Lys Ala His  Ala Lys Gly Glu Ser  Ser Val Ala
    1370                1375                1380

Leu Gly  Asn Gly Ala Thr Ala  Gly Glu Gln Gly Val  Ala Ile Gly
    1385                1390                1395

His Gly  Ala Val Ala Ser Gly  Lys Gln Ser Ile Ser  Ile Gly Thr
    1400                1405                1410

Gly Asn  Val Val Ser Gly Asn  Asn Ser Gly Ala Ile  Gly Asp Pro
    1415                1420                1425

Asn Thr  Ile Lys Ala Asp Arg  Ser Tyr Ala Leu Gly  Asn Asn Asn
    1430                1435                1440

Gln Val  Asn Ala Gly Gln Ser  Asp Val Phe Val Val  Gly Asn Asn
    1445                1450                1455

Val Lys  Asn Thr Thr Ser Asn  Ser Val Phe Leu Gly  Thr Asn Ser
    1460                1465                1470
```

-continued

```
Gly Tyr  Val Ala Ala Gly Ala  Thr Thr Ala Gly Ala  Gly Ala Leu
    1475                 1480                 1485

Glu Ser  Gln Val Ile Gly Gly  Val Tyr Asn Ala Tyr  Ala Gly Gly
    1490                 1495                 1500

Lys Ala  Thr Glu Val Lys Gly  Val Val Ser Val Gly  Asn Val Asp
    1505                 1510                 1515

Ser Asn  Gly Lys Met Glu Thr  Arg Arg Ile Gln Asn  Val Ala Pro
    1520                 1525                 1530

Gly Leu  Ile Ser Glu Gln Ser  Thr Asp Ala Ile Asn  Gly Ser Gln
    1535                 1540                 1545

Leu Tyr  Ser Leu Ile Ser Gln  His Lys Val His Met  Gly Asp Ile
    1550                 1555                 1560

His Asn  Lys Ile Asn Arg Asn  Asn Lys Ala Leu Arg  Ala Gly Ile
    1565                 1570                 1575

Ala Gly  Ser Asn Ala Ala Ala  Gly Leu Pro Gln Val  Tyr Leu Pro
    1580                 1585                 1590

Gly Lys  Ser Met Ile Ala Ala  Ser Ala Gly Thr Phe  Lys Gly Gln
    1595                 1600                 1605

Ser Ala  Leu Ala Val Gly Tyr  Ser Arg Ala Ser Asp  Asn Gly Lys
    1610                 1615                 1620

Leu Ile  Leu Lys Leu Gln Gly  Asn Ala Asn Thr Ser  Gly Glu Met
    1625                 1630                 1635

Gly Gly  Ser Val Gly Val Gly  Tyr Gln Trp
    1640                 1645
```

```
<210> SEQ ID NO 13
<211> LENGTH: 4206
<212> TYPE: DNA
<213> ORGANISM: Haemophilus parasuis

<400> SEQUENCE: 13

atgaataaaa tatttagagt tatttggagt catgctcaac aggcttgggt ggttgtgtct     60

gagttagtaa agtctcacac caaaacatcc gcttacacgg ataaaagagc tcaagtatgc    120

acctcagatt attttttaga taaacagcaa gataaattta aattaagtct tttaagtcta    180

gtattactag gtatattttt tagtccatca gctgctgcta acacaacaaa taccgcaaaa    240

ccatatcttc aagatgatgc tactacatcg aataatggat atgacaacgg tactattggt    300

attggtaaag agagtaaggc ttcgtatggt gctattgcta tcggtcagta ttcaaaagct    360

gaagctaggc ataatattgc gataggttat gatacacaag caggaaacca caaagaccac    420

tcaaactctg ttgcggtagg caacaatatt aaaatagatg ggaaggaagc agttgccatc    480

gggagtgctt caaaagcggg agagggatct gttgtcttag gcagacaagc cagtgcggaa    540

aagattaatc acgcagttgt aataggtcac aatactgtag tagatgggac ggaagcagtt    600

gccatcggga aaaaatcaaa agcgggaaag ggatctgttg tcttaggctc agatgccagt    660

gcgaaaaata ttgaacaagc agttgtaata ggtcactctg ctactgcaag taagtcaaaa    720

tctattgtta tcggggcaaa tgccaaagcg gatgggtatg gctccatatc aatcggtgga    780

gatgatttaa aaacaacgaa atatcaacct gatgttacag tccaaggcca agtccaaccc    840

caaccccaaa aaacaaaaat aacaactgcg agtggtggag cctctattgc tattgggggt    900

ggttctttgg ctaagggcga aggatctatt gttttaggtg ctttagcatc tgcaagtaaa    960

gatgaaggca ttgctatcgg tgcgaatagt aagtctacca atgagtacgg tattgcggtt   1020

ggtggtagtg caactgctac tggaaactac gccgttgctc ttggttggaa ctcgaaaggt   1080
```

-continued

```
gttgggacag attccattgc gataggtaag tctgcgacaa cagcaggggc atcttctgtt   1140
gttgtgggtg cccatatcgg tgtgacaggt caaaacttag tggcagttgg aagcctagca   1200
agtgctgaaa gtcatgctac tgccttgggt tataaagcct ctgctggtgg tatgagctct   1260
gttgctgtgg gtgataatgc caaaacaaat ggtagtgctg ctagagcaac cgcacttggt   1320
aataataccg ttgtcaccgt gggtggcggt gtggcattag gttatggatc taatgcaagt   1380
acagctggcg gtgtagaggg gttaaaacaa actcattctg tcacaacggg agaaagcact   1440
gaagctaacg gctttaaatc cacagaaaag gttgatggta ataagattgg tgcagtttct   1500
gtcggtttag caggtaataa actcatcaaa cgccaaatca ccaacgttgc tgcaggtaaa   1560
gaattaaccg atgcagtaaa cgtggcacag cttaaatcgc tcaccatgct aataggaggc   1620
gataacaaca gcagtggcaa ggtaggcatt tgggaaggta agctcactgt aaaaggagaa   1680
aatggtatta cttcctatgc tcagggcagt acgattacgg ttaaattaga gaaagatctc   1740
aaagataaaa ttgataagat tgccgctatg ggtaagttaa ttaaaagtgc ggaaaaagaa   1800
tcaaatggca atctaaaaat tacctataca gataattcgc atagcattat cgagaaaggt   1860
gaaaaaggag atcgtggcga aactggccct gcgggtccag caggtccagt aggtccagct   1920
ggaccacaag gtaaaactgg tcctgcaggt ccagcgggtc ctgctggagc aacaggacca   1980
caaggtccaa aaggacctaa gggcgataat ggtgatccag gaccaaaagg cgaagctggt   2040
ccaacaggtc cgaggggtcc ggcaggtcca gcgggtgctc agggcataca aggtccaaaa   2100
ggaaatgatg gagctccagg tgctagggga gagaaaggtg aaactggccc tgcgggtcca   2160
gagggaccta agggtgaaac tggccctgcg ggtccagcgg gacctaaggg tgaaccgggt   2220
cctaaaggtg aacaaggtct tccaggacct gcgggtccag caggggctaa gggtgacaaa   2280
ggtgatacgg gtccagcagg accacaagga cctacgggtc caacgggacc acaaggacct   2340
acggggccaa cgggaccaca aggacctacg gggccaacgg gaccacaagg acctgcgagt   2400
ccaacgggat cacaaggccc tgcgagtcca acgggatcac aaggacctgc gggtccaacg   2460
ggtccagcag gaccacaagg acctacgggt ccaacggggc ctgcgggtcc aacgggacca   2520
caaggacctg cgggtccagc aggaccacaa ggaccgcagg gtccagcagg accacaagga   2580
cctgcgggtc caatggggcc tgctggtcca aaaggagaaa atgtgggaag tggtttaggt   2640
ttgaaagatg atgctgaatc aaataaaacg gcacttaccc ctacagatgc acaaaaagct   2700
attgctggtg ataacaaaga cggtaaaggc ggcttattgg ctcaaacggg taatgcgtta   2760
aataatgtag cgacagtaaa agacttacaa gccattgcac aagcgggctt agacttgacg   2820
ggtaacaacg ccgataccac tgtacatcgt ccattgggta cgaagttaac cgttgagggt   2880
gaaggcaaat ggaatggtaa ggactcagcg gctaataacc tttatgtgga agcgcaagag   2940
gcagataaca aacttgttgt gaaaatgaac aaggatttaa cgaacttaaa ttctgtgact   3000
ttaggcactg cgacaatgac tggtgataag aatacaatca accttactgg tgcaggagag   3060
aaagtcgagg aagagtttgt taaatgggac ccagtgacta aacaacctat tcttgatgag   3120
aatggcaatc tccagaaata taaagagaaa gttgatcctc gtgtgaaact gagtggtatt   3180
gctgatggtg atatttcacc aaatagtact gatgcagtga atggtcgcca agtttatgtt   3240
ttaaccgatc gtatcaggtt cttccacacc aatgatggtc ataatgcaga ggagcaaatt   3300
aaccataagt cgaatacagt ggactcaaga gcttcaggtt catactctac tgcagttggt   3360
tacaaagctc acgcgaaagg ggatagagcg gtcgcatttg gtaacagtac attagctggc   3420
atacaatcgg tggctattgg taacgttgca attgcttcag gcgaaaaatc gatagctatt   3480
```

```
ggtgataatg ctaaggctgt gggcaaccaa tctatctcta tcggtacggg taacgtagtg   3540

aacggcaata actccggtgc atttggtgac ccaagtgtga ttaatgctga taactcttat   3600

tctgtgggta acaataatac gattgagaac gaaaatgtct ttgcattggg taacaagatt   3660

accaatacaa ccaacaactc ggtattcttg ggaacaaact caggctatgt ggcagcaggt   3720

gcaaccactg cgggagcggg tgctttagaa agccaagtaa caggtggtgt gtataacgct   3780

tacgcaggtg gcaaagctac tgaagtgaaa ggcgtggtga gcgtgggtaa tgtagacagt   3840

gatggcaaaa tggaaactcg tcgtattcaa aacgttgcac ctggtttaat ctctgagcaa   3900

agtaccgatg cgattaatgg tagccagttg tataatgttg cacatagatt gggtgcgaag   3960

ttagagagag aagggcgtca acttcgtgcg gggattgctg caacaacggc tatgagcaat   4020

attccacaag tgactttacc aggtaaaagc acattgggtg ctggtattgg tactttcgag   4080

ggacaaaatg cagttgctgt tggattctca agaatgtctg ataatggtcg tgtgattctt   4140

aaagtttctg caggtgcaac ttcgcaaggc aaatacaatg ctggtgcagg tattgcatta   4200

cagtgg                                                              4206
```

```
<210> SEQ ID NO 14
<211> LENGTH: 1402
<212> TYPE: PRT
<213> ORGANISM: haemophilus parasuis

<400> SEQUENCE: 14

Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Gly
    50                  55                  60

Ile Phe Phe Ser Pro Ser Ala Ala Ala Asn Thr Thr Asn Thr Ala Lys
65                  70                  75                  80

Pro Tyr Leu Gln Asp Asp Ala Thr Thr Ser Asn Asn Gly Tyr Asp Asn
                85                  90                  95

Gly Thr Ile Gly Ile Gly Lys Glu Ser Lys Ala Ser Tyr Gly Ala Ile
            100                 105                 110

Ala Ile Gly Gln Tyr Ser Lys Ala Glu Ala Arg His Asn Ile Ala Ile
        115                 120                 125

Gly Tyr Asp Thr Gln Ala Gly Asn His Lys Asp His Ser Asn Ser Val
    130                 135                 140

Ala Val Gly Asn Asn Ile Lys Ile Asp Gly Lys Glu Ala Val Ala Ile
145                 150                 155                 160

Gly Ser Ala Ser Lys Ala Gly Glu Gly Ser Val Val Leu Gly Arg Gln
                165                 170                 175

Ala Ser Ala Glu Lys Ile Asn His Ala Val Val Ile Gly His Asn Thr
            180                 185                 190

Val Val Asp Gly Thr Glu Ala Val Ala Ile Gly Lys Lys Ser Lys Ala
        195                 200                 205

Gly Lys Gly Ser Val Val Leu Gly Ser Asp Ala Ser Ala Lys Asn Ile
    210                 215                 220

Glu Gln Ala Val Val Ile Gly His Ser Ala Thr Ala Ser Lys Ser Lys
225                 230                 235                 240

Ser Ile Val Ile Gly Ala Asn Ala Lys Ala Asp Gly Tyr Gly Ser Ile
```

-continued

```
                245                 250                 255

Ser Ile Gly Gly Asp Asp Leu Lys Thr Thr Lys Tyr Gln Pro Asp Val
            260                 265                 270

Thr Val Gln Gly Gln Val Gln Pro Gln Pro Gln Lys Thr Lys Ile Thr
        275                 280                 285

Thr Ala Ser Gly Gly Ala Ser Ile Ala Ile Gly Gly Gly Ser Leu Ala
    290                 295                 300

Lys Gly Glu Gly Ser Ile Val Leu Gly Ala Leu Ala Ser Ala Ser Lys
305                 310                 315                 320

Asp Glu Gly Ile Ala Ile Gly Ala Asn Ser Lys Ser Thr Asn Glu Tyr
                325                 330                 335

Gly Ile Ala Val Gly Gly Ser Ala Thr Ala Thr Gly Asn Tyr Ala Val
            340                 345                 350

Ala Leu Gly Trp Asn Ser Lys Gly Val Gly Thr Asp Ser Ile Ala Ile
        355                 360                 365

Gly Lys Ser Ala Thr Thr Ala Gly Ala Ser Ser Val Val Val Gly Ala
    370                 375                 380

His Ile Gly Val Thr Gly Gln Asn Leu Val Ala Val Gly Ser Leu Ala
385                 390                 395                 400

Ser Ala Glu Ser His Ala Thr Ala Leu Gly Tyr Lys Ala Ser Ala Gly
                405                 410                 415

Gly Met Ser Ser Val Ala Val Gly Asp Asn Ala Lys Thr Asn Gly Ser
            420                 425                 430

Ala Ala Arg Ala Thr Ala Leu Gly Asn Asn Thr Val Val Thr Val Gly
        435                 440                 445

Gly Gly Val Ala Leu Gly Tyr Gly Ser Asn Ala Ser Thr Ala Gly Gly
    450                 455                 460

Val Glu Gly Leu Lys Gln Thr His Ser Val Thr Thr Gly Glu Ser Thr
465                 470                 475                 480

Glu Ala Asn Gly Phe Lys Ser Thr Glu Lys Val Asp Gly Asn Lys Ile
                485                 490                 495

Gly Ala Val Ser Val Gly Leu Ala Gly Asn Lys Leu Ile Lys Arg Gln
            500                 505                 510

Ile Thr Asn Val Ala Ala Gly Lys Glu Leu Thr Asp Ala Val Asn Val
        515                 520                 525

Ala Gln Leu Lys Ser Leu Thr Met Leu Ile Gly Gly Asp Asn Asn Ser
    530                 535                 540

Ser Gly Lys Val Gly Ile Trp Glu Gly Lys Leu Thr Val Lys Gly Glu
545                 550                 555                 560

Asn Gly Ile Thr Ser Tyr Ala Gln Gly Ser Thr Ile Thr Val Lys Leu
                565                 570                 575

Glu Lys Asp Leu Lys Asp Lys Ile Asp Lys Ile Ala Ala Met Gly Lys
            580                 585                 590

Leu Ile Lys Ser Ala Glu Lys Glu Ser Asn Gly Asn Leu Lys Ile Thr
        595                 600                 605

Tyr Thr Asp Asn Ser His Ser Ile Ile Glu Lys Gly Glu Lys Gly Asp
    610                 615                 620

Arg Gly Glu Thr Gly Pro Ala Gly Pro Ala Gly Pro Val Gly Pro Ala
625                 630                 635                 640

Gly Pro Gln Gly Lys Thr Gly Pro Ala Gly Pro Ala Gly Pro Ala Gly
                645                 650                 655

Ala Thr Gly Pro Gln Gly Pro Lys Gly Pro Lys Gly Asp Asn Gly Asp
            660                 665                 670
```

```
Pro Gly Pro Lys Gly Glu Ala Gly Pro Thr Gly Pro Arg Gly Pro Ala
        675                 680                 685

Gly Pro Ala Gly Ala Gln Gly Ile Gln Gly Pro Lys Gly Asn Asp Gly
    690                 695                 700

Ala Pro Gly Ala Arg Gly Glu Lys Gly Glu Thr Gly Pro Ala Gly Pro
705                 710                 715                 720

Glu Gly Pro Lys Gly Glu Thr Gly Pro Ala Gly Pro Ala Gly Pro Lys
                725                 730                 735

Gly Glu Pro Gly Pro Lys Gly Glu Gln Gly Leu Pro Gly Pro Ala Gly
            740                 745                 750

Pro Ala Gly Ala Lys Gly Asp Lys Gly Asp Thr Gly Pro Ala Gly Pro
        755                 760                 765

Gln Gly Pro Thr Gly Pro Thr Gly Pro Gln Gly Pro Thr Gly Pro Thr
    770                 775                 780

Gly Pro Gln Gly Pro Thr Gly Pro Thr Gly Pro Gln Gly Pro Ala Ser
785                 790                 795                 800

Pro Thr Gly Ser Gln Gly Pro Ala Ser Pro Thr Gly Ser Gln Gly Pro
                805                 810                 815

Ala Gly Pro Thr Gly Pro Ala Gly Pro Gln Gly Pro Thr Gly Pro Thr
            820                 825                 830

Gly Pro Ala Gly Pro Thr Gly Pro Gln Gly Pro Ala Gly Pro Ala Gly
        835                 840                 845

Pro Gln Gly Pro Gln Gly Pro Ala Gly Pro Gln Gly Pro Ala Gly Pro
    850                 855                 860

Met Gly Pro Ala Gly Pro Lys Gly Glu Asn Val Gly Ser Gly Leu Gly
865                 870                 875                 880

Leu Lys Asp Asp Ala Glu Ser Asn Lys Thr Ala Leu Thr Pro Thr Asp
                885                 890                 895

Ala Gln Lys Ala Ile Ala Gly Asp Asn Lys Asp Gly Lys Gly Gly Leu
            900                 905                 910

Leu Ala Gln Thr Gly Asn Ala Leu Asn Asn Val Ala Thr Val Lys Asp
        915                 920                 925

Leu Gln Ala Ile Ala Gln Ala Gly Leu Asp Leu Thr Gly Asn Asn Ala
    930                 935                 940

Asp Thr Thr Val His Arg Pro Leu Gly Thr Lys Leu Thr Val Glu Gly
945                 950                 955                 960

Glu Gly Lys Trp Asn Gly Lys Asp Ser Ala Ala Asn Asn Leu Tyr Val
                965                 970                 975

Glu Ala Gln Glu Ala Asp Asn Lys Leu Val Val Lys Met Asn Lys Asp
            980                 985                 990

Leu Thr Asn Leu Asn Ser Val Thr  Leu Gly Thr Ala Thr  Met Thr Gly
        995                 1000                 1005

Asp Lys  Asn Thr Ile Asn Leu  Thr Gly Ala Gly Glu  Lys Val Glu
    1010                 1015                 1020

Glu Glu  Phe Val Lys Trp Asp  Pro Val Thr Lys Gln  Pro Ile Leu
    1025                 1030                 1035

Asp Glu  Asn Gly Asn Leu Gln  Lys Tyr Lys Glu Lys  Val Asp Pro
    1040                 1045                 1050

Arg Val  Lys Leu Ser Gly Ile  Ala Asp Gly Asp Ile  Ser Pro Asn
    1055                 1060                 1065

Ser Thr  Asp Ala Val Asn Gly  Arg Gln Val Tyr Val  Leu Thr Asp
    1070                 1075                 1080

Arg Ile  Arg Phe Phe His Thr  Asn Asp Gly His Asn  Ala Glu Glu
    1085                 1090                 1095
```

```
Gln Ile  Asn His Lys Ser Asn  Thr Val Asp Ser Arg  Ala Ser Gly
    1100                 1105                 1110

Ser Tyr  Ser Thr Ala Val Gly  Tyr Lys Ala His Ala  Lys Gly Asp
    1115                 1120                 1125

Arg Ala  Val Ala Phe Gly Asn  Ser Thr Leu Ala Gly  Ile Gln Ser
    1130                 1135                 1140

Val Ala  Ile Gly Asn Val Ala  Ile Ala Ser Gly Glu  Lys Ser Ile
    1145                 1150                 1155

Ala Ile  Gly Asp Asn Ala Lys  Ala Val Gly Asn Gln  Ser Ile Ser
    1160                 1165                 1170

Ile Gly  Thr Gly Asn Val Val  Asn Gly Asn Asn Ser  Gly Ala Phe
    1175                 1180                 1185

Gly Asp  Pro Ser Val Ile Asn  Ala Asp Asn Ser Tyr  Ser Val Gly
    1190                 1195                 1200

Asn Asn  Asn Thr Ile Glu Asn  Glu Asn Val Phe Ala  Leu Gly Asn
    1205                 1210                 1215

Lys Ile  Thr Asn Thr Thr Asn  Asn Ser Val Phe Leu  Gly Thr Asn
    1220                 1225                 1230

Ser Gly  Tyr Val Ala Ala Gly  Ala Thr Thr Ala Gly  Ala Gly Ala
    1235                 1240                 1245

Leu Glu  Ser Gln Val Thr Gly  Gly Val Tyr Asn Ala  Tyr Ala Gly
    1250                 1255                 1260

Gly Lys  Ala Thr Glu Val Lys  Gly Val Val Ser Val  Gly Asn Val
    1265                 1270                 1275

Asp Ser  Asp Gly Lys Met Glu  Thr Arg Arg Ile Gln  Asn Val Ala
    1280                 1285                 1290

Pro Gly  Leu Ile Ser Glu Gln  Ser Thr Asp Ala Ile  Asn Gly Ser
    1295                 1300                 1305

Gln Leu  Tyr Asn Val Ala His  Arg Leu Gly Ala Lys  Leu Glu Arg
    1310                 1315                 1320

Glu Gly  Arg Gln Leu Arg Ala  Gly Ile Ala Ala Thr  Thr Ala Met
    1325                 1330                 1335

Ser Asn  Ile Pro Gln Val Thr  Leu Pro Gly Lys Ser  Thr Leu Gly
    1340                 1345                 1350

Ala Gly  Ile Gly Thr Phe Glu  Gly Gln Asn Ala Val  Ala Val Gly
    1355                 1360                 1365

Phe Ser  Arg Met Ser Asp Asn  Gly Arg Val Ile Leu  Lys Val Ser
    1370                 1375                 1380

Ala Gly  Ala Thr Ser Gln Gly  Lys Tyr Asn Ala Gly  Ala Gly Ile
    1385                 1390                 1395

Ala Leu  Gln Trp
    1400
```

<210> SEQ ID NO 15
<211> LENGTH: 3298
<212> TYPE: DNA
<213> ORGANISM: Haemophilus parasuis

<400> SEQUENCE: 15

```
atgaataaaa tatttagagt tatttggagt catgctcaac aggcttgggt ggttgtatct      60

gagttagtaa agtctcatac taaaacatcc gcttacacgg ataaaagagc tcaagtatgc     120

acctcagatt attttttaga taaacagcaa gataaattta aattaagtct tttaagtcta     180

gtattactag gtatattttt tagtccagta ggttcagcag catggttggt agatggttct     240
```

-continued

```
gaaaaaggaa gtgacgctga cgctggtact attggtattg gtattgatag tagggttggg    300
cctggttcta ttgtcatcgg tcagtacgca aaagctgaag gtaggacttc tattgcgata    360
ggttatcgag ctgaaacaac cggtgacaaa gccgtagccg ttggggcaac tgcacaagca    420
ttcaattatt ctgcggctta tggttatgga gcacaagcaa aagcaatagg cgctgttgca    480
gtcggtcaag aagctattgc aaatcaaaat ggaggcgttg cattgggtta ccaatcatct    540
gttaacgtta ccaatggtgt tgcattgggt tctttctcta gagcagatac gaaagggggt    600
attgaaggaa caaaacaacc tttttctgtg acagagggag aaagcactgt tgagaatgga    660
tttaaatcca cagaaaatcc tgatattggt gcggtttctg ttggtagcag ttttggttgg    720
aagaattcaa ataaactaat caaacgccaa atcaccaacg ttgcggcagg tacacaagat    780
accgatgcgg taaacgtggc acagcttaaa tctttgacga tgaaaattgc aggcaatacc    840
agcgaacaaa cacaaccaaa agtggggttg tgggatggta cgctcactgt aaaaggagaa    900
aatggtatta cttcccatgc taatggcagt acgattacgg ttaaattaga gcaagaactc    960
aaagataaaa ttgataagat tgccgctatg ggtaagttaa ttcaaagtgc ggaaaaagaa   1020
gcaaatggcg atctaaaaat tacctataca gatggttcga gtgacactat caagaaaggt   1080
gaaaaaggag atcaaggtcc gatgggtccg gcaggcccag cgggtgctca gggcatacaa   1140
ggtcctaaag gagatagagg tccaaaaggt gatacaggtg agagaggtgc aactggccct   1200
gcgggtccag taggtccagc tggccctgtg ggtccagtcg gtgctcaagg tccagcaggt   1260
cctagaggcg aagcaggtcc tgctggagca acaggaccac aaggtgcaac aggtccagcg   1320
ggagagccag gcaagcaggg tcctaggggg gaacaaggtg cacctggtcc tgcaggtcca   1380
aaaggagagg caggagcaaa aggcgataag ggtgaccctg gtgaagcggg accagtcggc   1440
cctcaaggtc ctgtgggtgc aactggccct gtgggtccgg caggcccagc gggagagcga   1500
ggcgagcagg gtcctagggg agataaaggt gaaactggtc ctgcgggtcc agcaggtcca   1560
attggaccac aaggtgaaac tggtcctaag gggggataaag gcgaacaagg tctaagaggt   1620
gaacaaggcc ctgcgggtga gcgaggagaa ataggccctg cgggtccaat tggaccacaa   1680
ggtgtacctg gtcctaaggg ggataaaggc gaacaaggtc taagaggtga aactggccct   1740
gcgggtgagc gaggagaaat aggccctgcg ggtccagcgg gaccacgagg acctgagggt   1800
ccagcagggg ctaagggtga acagggtcaa aaaggagata caggtccaaa aggtgataga   1860
ggccaacaag ggattccggg ggtagcaggt cctaagggcg atagaggcga tgttggtccg   1920
atgggtccag tgggtccaac tggaccacaa ggtgcacctg gtcctgcggg tccagcggga   1980
gagccaggca agcagggtcc taggggagag aaaggtgaaa ttggtcctgt gggtccaacg   2040
ggaccacaag gaccgcaagg aataccgggt attcagggac agaagggtga gcgaggagaa   2100
acaggctctg caggtgcagc tggacctgcg ggcccagcag gggctaaggg tgaaccgggt   2160
caaaaaggag atacaggtcc agtgggtcca acggggccta ggggtgaacc aggtccaacg   2220
ggaccacaag gaccgcaagg aataccgggt gctcagggac ctaaggggga taaaggcgat   2280
ccaggacaag cgggtcctaa aggagaaaaa ggagatacag gtcctagagg tgaaactggt   2340
cctgcgggtc cagcaggggc taagggtgaa cagggtccta gaggtgaaca agggcttcca   2400
ggggtagcag gtcctaaggg cgatagaggc gaagctggcc ctgcgggtcc agtaggtcca   2460
gctggaccac aaggaccgca gggaacagcg ggtgctcagg gacagaaggg ggataaaggc   2520
gaaccaggac aagcgggtcc aaaaggagat acaggtcaga aaggtgaaac tggccctgcg   2580
ggtccaacgg gacctaaggg tgacaaaggt gatacgggtc cagcaggatc acaaggacct   2640
```

```
acgggtccaa ctggaaattc ggaattaaaa ggcattacgt cgattgccaa tggtaacgac   2700

gccaccaagg cgaatggggc taagattacc ttgtctacag gttctacaaa taaaacagtt   2760

aatgttaatg atgcgaaaat taccaatgtg gcggctggta cagcagatac cgatgcggtg   2820

aatgtgaaac agttgaaatc tgcgaaaact gaagtggaat ctaccgatca cagtgtggtg   2880

attaaagagc gtcagggcga taatcagcaa atcgtgtatg atttggcggt tgctaaaacg   2940

aaactcactg cctctaagga taaacgcacc attagtgcag cagataaagg caaccatttt   3000

gcgacaggag atgaagtcgc agtagcaatt aataccgcaa cagcagccgc aagaactgaa   3060

gttgaagcgg gtaaaaatgt gaaagtgact tcaaaaacgg gggcaaatgg tcagaatatt   3120

tacaaggtga gcgtgtctgg agatttaagc gacattactt caattagtaa tggcgatacg   3180

aaagtatctt taggtaaaga taagcaagga aatccagttg taaatatgaa tggtgccaga   3240

attaccaacg ttggagatgg tagtgctgag ggcgatattg tgaatgttcg tcagctca     3298
```

<210> SEQ ID NO 16
<211> LENGTH: 1099
<212> TYPE: PRT
<213> ORGANISM: haemophilus parasuis

<400> SEQUENCE: 16

```
Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Gly
    50                  55                  60

Ile Phe Phe Ser Pro Val Gly Ser Ala Ala Trp Leu Val Asp Gly Ser
65                  70                  75                  80

Glu Lys Gly Ser Asp Ala Asp Ala Gly Thr Ile Gly Ile Gly Ile Asp
                85                  90                  95

Ser Arg Val Gly Pro Gly Ser Ile Val Ile Gly Gln Tyr Ala Lys Ala
            100                 105                 110

Glu Gly Arg Thr Ser Ile Ala Ile Gly Tyr Arg Ala Glu Thr Thr Gly
        115                 120                 125

Asp Lys Ala Val Ala Val Gly Ala Thr Ala Gln Ala Phe Asn Tyr Ser
    130                 135                 140

Ala Ala Tyr Gly Tyr Gly Ala Gln Ala Lys Ala Ile Gly Ala Val Ala
145                 150                 155                 160

Val Gly Gln Glu Ala Ile Ala Asn Gln Asn Gly Gly Val Ala Leu Gly
                165                 170                 175

Tyr Gln Ser Ser Val Asn Val Thr Asn Gly Val Ala Leu Gly Ser Phe
            180                 185                 190

Ser Arg Ala Asp Thr Lys Gly Gly Ile Glu Gly Thr Lys Gln Pro Phe
        195                 200                 205

Ser Val Thr Glu Gly Glu Ser Thr Val Glu Asn Gly Phe Lys Ser Thr
    210                 215                 220

Glu Asn Pro Asp Ile Gly Ala Val Ser Val Gly Ser Ser Phe Gly Trp
225                 230                 235                 240

Lys Asn Ser Asn Lys Leu Ile Lys Arg Gln Ile Thr Asn Val Ala Ala
                245                 250                 255

Gly Thr Gln Asp Thr Asp Ala Val Asn Val Ala Gln Leu Lys Ser Leu
            260                 265                 270
```

```
Thr Met Lys Ile Ala Gly Asn Thr Ser Glu Gln Thr Gln Pro Lys Val
        275                 280                 285

Gly Leu Trp Asp Gly Thr Leu Thr Val Lys Gly Glu Asn Gly Ile Thr
    290                 295                 300

Ser His Ala Asn Gly Ser Thr Ile Thr Val Lys Leu Glu Gln Glu Leu
305                 310                 315                 320

Lys Asp Lys Ile Asp Lys Ile Ala Ala Met Gly Lys Leu Ile Gln Ser
                325                 330                 335

Ala Glu Lys Glu Ala Asn Gly Asp Leu Lys Ile Thr Tyr Thr Asp Gly
            340                 345                 350

Ser Ser Asp Thr Ile Lys Lys Gly Glu Lys Gly Asp Gln Gly Pro Met
        355                 360                 365

Gly Pro Ala Gly Pro Ala Gly Ala Gln Gly Ile Gln Gly Pro Lys Gly
    370                 375                 380

Asp Arg Gly Pro Lys Gly Asp Thr Gly Glu Arg Gly Ala Thr Gly Pro
385                 390                 395                 400

Ala Gly Pro Val Gly Pro Ala Gly Pro Val Gly Pro Val Gly Ala Gln
                405                 410                 415

Gly Pro Ala Gly Pro Arg Gly Glu Ala Gly Pro Ala Gly Ala Thr Gly
            420                 425                 430

Pro Gln Gly Ala Thr Gly Pro Ala Gly Glu Pro Gly Lys Gln Gly Pro
        435                 440                 445

Arg Gly Glu Gln Gly Ala Pro Gly Pro Ala Gly Pro Lys Gly Glu Ala
    450                 455                 460

Gly Ala Lys Gly Asp Lys Gly Asp Pro Gly Glu Ala Gly Pro Val Gly
465                 470                 475                 480

Pro Gln Gly Pro Val Gly Ala Thr Gly Pro Val Gly Pro Ala Gly Pro
                485                 490                 495

Ala Gly Glu Arg Gly Glu Gln Gly Pro Arg Gly Asp Lys Gly Glu Thr
            500                 505                 510

Gly Pro Ala Gly Pro Ala Gly Pro Ile Gly Pro Gln Gly Glu Thr Gly
        515                 520                 525

Pro Lys Gly Asp Lys Gly Glu Gln Gly Leu Arg Gly Glu Gln Gly Pro
    530                 535                 540

Ala Gly Glu Arg Gly Glu Ile Gly Pro Ala Gly Pro Ile Gly Pro Gln
545                 550                 555                 560

Gly Val Pro Gly Pro Lys Gly Asp Lys Gly Glu Gln Gly Leu Arg Gly
                565                 570                 575

Glu Thr Gly Pro Ala Gly Glu Arg Gly Glu Ile Gly Pro Ala Gly Pro
            580                 585                 590

Ala Gly Pro Arg Gly Pro Glu Gly Pro Ala Gly Ala Lys Gly Glu Gln
        595                 600                 605

Gly Gln Lys Gly Asp Thr Gly Pro Lys Gly Asp Arg Gly Gln Gln Gly
    610                 615                 620

Ile Pro Gly Val Ala Gly Pro Lys Gly Asp Arg Gly Asp Val Gly Pro
625                 630                 635                 640

Met Gly Pro Val Gly Pro Thr Gly Pro Gln Gly Ala Pro Gly Pro Ala
                645                 650                 655

Gly Pro Ala Gly Glu Pro Gly Lys Gln Gly Pro Arg Gly Glu Lys Gly
            660                 665                 670

Glu Ile Gly Pro Val Gly Pro Thr Gly Pro Gln Gly Pro Gln Gly Ile
        675                 680                 685

Pro Gly Ile Gln Gly Gln Lys Gly Glu Arg Gly Glu Thr Gly Ser Ala
```

-continued

```
    690                 695                 700

Gly Ala Ala Gly Pro Ala Gly Pro Ala Gly Ala Lys Gly Glu Pro Gly
705                 710                 715                 720

Gln Lys Gly Asp Thr Gly Pro Val Gly Pro Thr Gly Pro Arg Gly Glu
                725                 730                 735

Pro Gly Pro Thr Gly Pro Gln Gly Pro Gln Gly Ile Pro Gly Ala Gln
            740                 745                 750

Gly Pro Lys Gly Asp Lys Gly Asp Pro Gly Gln Ala Gly Pro Lys Gly
        755                 760                 765

Glu Lys Gly Asp Thr Gly Pro Arg Gly Glu Thr Gly Pro Ala Gly Pro
    770                 775                 780

Ala Gly Ala Lys Gly Glu Gln Gly Pro Arg Gly Glu Gln Gly Leu Pro
785                 790                 795                 800

Gly Val Ala Gly Pro Lys Gly Asp Arg Gly Glu Ala Gly Pro Ala Gly
                805                 810                 815

Pro Val Gly Pro Ala Gly Pro Gln Gly Pro Gln Gly Thr Ala Gly Ala
            820                 825                 830

Gln Gly Gln Lys Gly Asp Lys Gly Glu Pro Gly Gln Ala Gly Pro Lys
        835                 840                 845

Gly Asp Thr Gly Gln Lys Gly Glu Thr Gly Pro Ala Gly Pro Thr Gly
    850                 855                 860

Pro Lys Gly Asp Lys Gly Asp Thr Gly Pro Ala Gly Ser Gln Gly Pro
865                 870                 875                 880

Thr Gly Pro Thr Gly Asn Ser Glu Leu Lys Gly Ile Thr Ser Ile Ala
                885                 890                 895

Asn Gly Asn Asp Ala Thr Lys Ala Asn Gly Ala Lys Ile Thr Leu Ser
            900                 905                 910

Thr Gly Ser Thr Asn Lys Thr Val Asn Val Asn Asp Ala Lys Ile Thr
        915                 920                 925

Asn Val Ala Ala Gly Thr Ala Asp Thr Asp Ala Val Asn Val Lys Gln
    930                 935                 940

Leu Lys Ser Ala Lys Thr Glu Val Glu Ser Thr Asp His Ser Val Val
945                 950                 955                 960

Ile Lys Glu Arg Gln Gly Asp Asn Gln Gln Ile Val Tyr Asp Leu Ala
                965                 970                 975

Val Ala Lys Thr Lys Leu Thr Ala Ser Lys Asp Lys Arg Thr Ile Ser
            980                 985                 990

Ala Ala Asp Lys Gly Asn His Phe  Ala Thr Gly Asp Glu  Val Ala Val
        995                 1000                1005

Ala Ile  Asn Thr Ala Thr Ala  Ala Ala Arg Thr Glu  Val Glu Ala
    1010                1015                1020

Gly Lys  Asn Val Lys Val Thr  Ser Lys Thr Gly Ala  Asn Gly Gln
    1025                1030                1035

Asn Ile  Tyr Lys Val Ser Val  Ser Gly Asp Leu Ser  Asp Ile Thr
    1040                1045                1050

Ser Ile  Ser Asn Gly Asp Thr  Lys Val Ser Leu Gly  Lys Asp Lys
    1055                1060                1065

Gln Gly  Asn Pro Val Val Asn  Met Asn Gly Ala Arg  Ile Thr Asn
    1070                1075                1080

Val Gly  Asp Gly Ser Ala Glu  Gly Asp Ile Val Asn  Val Arg Gln
    1085                1090                1095

Leu
```

-continued

<210> SEQ ID NO 17
<211> LENGTH: 5043
<212> TYPE: DNA
<213> ORGANISM: Haemophilus parasuis

<400> SEQUENCE: 17
atgaataaaa tatttagagt tatttggagt catgctcaac aggcttgggt tgttgtatct 60
gaattagtaa agtctcatac caaaacatcc acttacacga ataaaagagc tcaagtatgc 120
acctcacatt attttttaga taaacagcaa gataaattta aattaagttt tttaagtcta 180
gtattattaa gtatattttt tagtccagta ggttcagcaa ggctttttct agatggtgct 240
ggtgaagcga gtggaggagt tgacgatggt tctattggta ttggtcaaga tagtagggtt 300
gggcatggtt ctattgctat tggtcagcac tcaaaagctg aaggtaggac taatgttgcg 360
ataggttata gagcacattc aggaacagga ttgcatggtg ttgcggtagg gtataatagt 420
ttgtctagtg ctaattctgt tactcttggt ggtaacacga aagctgctgg ggcaaattcc 480
gttgcgatag gtaattctgt gcaaataaca gggagtaact ctgttgttgt gggttcccag 540
atcatcgata tgacaggtga aaatttagtg gcaattggac acggagcaag tgctggaaat 600
tattctactg ccttcggtta tagagcctct gccaatggta taggctctgt tgctgtgggt 660
gaccgggcaa ataccaacca aacaagtaga gcaaccgcac ttggtaacaa ttcaattgtt 720
cttgttggtg gtggcgtggc gttaggttat ggttcgacag cacaaacgaa tgggggtata 780
gatggagtga gacaatccca ttctgtaata acagatgcaa gtactgttaa caatggtttt 840
aaatcaacac aaagtgttga tgacagtcct gagggtcatc ctaaaggttc taatgacttt 900
cttatcggtg cagtttctgt gggtaataat aaaatcaaac gccaaatcgt caacgttgcg 960
gcaggtaaag atttaactga tgcagtaaac gtggcgcagc ttcaatcgct cacaatgaaa 1020
attggtggag attccaacgc tgaagaacaa ccaaaagttg gtttatgggc aggtacgctc 1080
aacgtaaaag gcgaaaatgg tcttacttcc gaggctagcg gcgatacgat tacggttaaa 1140
ttaaccgacg atattaaacg aaaaattgat aatgccgctg aaccaggtac gtttcacttt 1200
aatactgatg gcaaattgtc aatggggaat ccaggagttg caactattca gactgtagtc 1260
aatgctgtaa ataatgcagg ctggaaactg aatgtcactc agagagacgg tggtcaaggt 1320
acttctattc attttgatcc atatcttatc aaaatgggtg agactgtaac ctttatcgcc 1380
ggaaataata ttaaattaca acaaacgaac gaaaatatta cgatttctac gcttggtaag 1440
ttaattaaag aaacgcaaac cttagcgggt ggcggtttga aaattactta tactgataat 1500
acatccgata ctattagcgg tggtgcacca ggtcctgcgg gcccagtggg tcctcggggc 1560
cctgcgggtc caaagggaga gcggggtgaa ccaggtccta gaggtgaacg aggagaacaa 1620
ggactaacgg gtccagcagg accacaaggt gtaccaggtc cagcaggtcc agtaggtcct 1680
gcgggagagc gcggtcctgc gggcccagtt ggtccagttg gtcctcgggg ccctgctggt 1740
gaaacaggtc ctagaggtga acgaggagaa caaggactac aaggtgcaac aggtccagcg 1800
ggtccagcag gggctccagg agtagctggt cctaagggcg atagaggtga agctggtccg 1860
aaaggtgaag caggtccaac aggtccaagg ggagagcggg gtccagcagg tgataagggt 1920
gataaaggtg atacgggtcc gatgggtcct ccgggtccag taggtccagc aggtcctacg 1980
ggcccagaag gtcctagagg tgaaaagggt cctaaaggtg aacagggtga tcagggacta 2040
aaaggtgaaa ctggtccagc aggtccagca ggtcctgcgg gtccagtggg tccagttggt 2100
ccacaaggtg ctaagggtga gcaaggtcct agaggtgaac gaggagaaca aggagcagcg 2160
ggtccaacag gaccacaagg tgcaccaggt ccagtaggtc ctgcgggtgc agcaggtcca 2220
gcaggaccta ggggtcctaa aggtgatcca ggtcagaaag gggatgctgg tctgcaaggt 2280
cctgcgggag agcgaggtga gcgcggtcct gagggtccac aaggtcctag aggtgaacga 2340
ggagaaccag gagcaccagg tccaatgggt ccacaaggac cgcaagggaa agagggtcca 2400
gttggtcctc ggggccctgc tggtcctgca ggtgagcaag gtccagcagg ccctagaggt 2460
gaaaagggtc ttaaaggtga caaaggtgaa cagggtgatc gaggaccaac aggtgaagcg 2520
ggtccgaaag gtgaagcagg tccagcaggt gctaagggtg atcaaggtcc accgggagag 2580
cgaggtgagc gcggtcctgc gggtgcaaca ggacaaacag gtccagcagg acctaggggt 2640
cctaaaggtg atccaggtca gaaaggggat gctggtctgc aaggtcctgc gggagagcga 2700
ggtgagcgcg gagaaacagg tgagcgcggt cctgcgggcc cagttggtcc agttggtcct 2760
cggggccctg ctggtgaaac aggtcctaga ggtgaacgag gagaacaagg actacaaggt 2820
gcaacaggtc cagcaggtcc tccgggtcca gcaggggctc ggggtgaagc aggtcctaga 2880
ggtgaacgag gagaaccagg actagcgggt ccaacaggac cacaaggtgc accaggtcca 2940
gtaggtcctg cgggtgcagc aggtccagca ggacctaggg gtcctaaagg tgatccaggt 3000
cagaaagggg atgctggtct gcaaggtccg atgggtcctg cgggtcctgc tggtgcaata 3060
ggtcctgcgg gcccagcagg tcctaaagga gatcaaggtc tagttggtcc gcaaggtcct 3120
acaggtgcta agggtgagca aggtcctaga ggtgaaccag gtattcaagg accaagaggt 3180
gaagctggtc cgaaaggtga agttggtcca gcaggtccga caggtcctac tggtgctagg 3240
ggagaaaaag gcgacactgg ccctgcgggt ccagcagggg ctcagggtga acaaggtcct 3300
ataggtccag caggacctaa gggtgataaa ggtgaacagg gtgatcaagg accaagaggt 3360
gaagctggtc cagcaggtcc tcagggccct gctggtgcaa caggtcctga gggtccagtt 3420
ggtccgacag gtcctgcggg tccaacaggt ccgaaaggcg atacaggccc agaaggtcct 3480
aaaggagagc aaggtccagt gggtccacaa ggtcctacag gtgctaagga tttaacgaac 3540
ttaaattctg tgactttagg cactgcgaca atgactggtg ataagaatac aatcaacctt 3600
actggtgcag gagagaaagt cgaggaagag tttgttaaat gggatccagt gaccaaacaa 3660
cctatttatg ataaggatgg caatctccag aaatataaag agaaagttga tcctcgtgtg 3720
aaattgagtg gtattgctga tggtgatatt tcaccgaata gtactgatgc agtgaatggt 3780
cgccaagttt acgctttaac caatggtaac caagttgaac agaaaaaaga tggttctaca 3840
gtaacctatg ctaaggacaa agatggttca gtcattactg aagttaaacg cgataagaat 3900
ggcaatcctg aattggatgc tgatggtaac gagattgtac aagctaaaga gtacacactt 3960
accacttaca acgtgaaagg tcaaactgag tttgttacaa actctgtgat tactgcgatt 4020
cataatatga acgaacaagg tatcaagttc ttccatacaa atgatggtgt agcagagcct 4080
attaaccaag catctaacga tattgactca agtgcttcag gtacttatgc aacagctata 4140
ggttataaag ctgttgcggc gggtgataat gcattagcta taggtaaagg tgcaaccgca 4200
tcgggtaaaa actcaattgc tatcggtact ggtaaccaag taattgcgaa taaatcaggt 4260
gcgtttggtg acccgaatat cattcgtggt gttcaaattg gtactgacag tgcaggtaat 4320
ccaatctata aaggcattga tggaagctat gcattcggta atgataatgt aattacatca 4380
agcaatacct ttgttcttgg taataatgtg aataataagc gtgatagtaa tggtgcatta 4440
acttggatgt ctgcaactcc tgaagggacg gttgagaatt ccgtttattt aggtaacaat 4500
acgacggcta cagctggtga tggtagtcaa acaggctctc tcaaaaactg gaaacaagat 4560
ggttctagag gttcaacgac tacagcagga tcgactggta cagtatcaag tgtaacggtg 4620
ggtaacatga tttatgatgg cttcgctggt gcaaccgcaa acggtgtggt ttccgtaggt 4680
gctgcaggtg atgagcgccg tatccaaaat gttgcaacag gggaaatttc ttctacttca 4740
accgatgcga ttaatggtag ccagttgtat aatgttgcac atagattggg tgcgaagtta 4800
gagagagaag ggcgtcaact tcgtgcgggt attgctgcaa caacggctat gagcaatatt 4860
ccacaagtga ctttaccagg taaaagcaca ttgggtgctg gtattggtac tttcgaggga 4920
caaaatgcag ttgctgttgg attctcaaga atgtctgata atggtcgtgt gattcttaaa 4980
gtttctgcag gtgcaacttc gcaaggcaaa tacaatgctg gtgcaggtat tgcattacag 5040
tgg 5043

<210> SEQ ID NO 18
<211> LENGTH: 1681
<212> TYPE: PRT
<213> ORGANISM: haemophilus parasuis

<400> SEQUENCE: 18

Met Asn Lys Ile Phe Arg Val Ile Trp Ser His Ala Gln Gln Ala Trp
1 5 10 15

Val Val Val Ser Glu Leu Val Lys Ser His Thr Lys Thr Ser Thr Tyr
20 25 30

Thr Asn Lys Arg Ala Gln Val Cys Thr Ser His Tyr Phe Leu Asp Lys
35 40 45

Gln Gln Asp Lys Phe Lys Leu Ser Phe Leu Ser Leu Val Leu Leu Ser
50 55 60

Ile Phe Phe Ser Pro Val Gly Ser Ala Arg Leu Phe Leu Asp Gly Ala
65 70 75 80

Gly Glu Ala Ser Gly Gly Val Asp Asp Gly Ser Ile Gly Ile Gly Gln
85 90 95

Asp Ser Arg Val Gly His Gly Ser Ile Ala Ile Gly Gln His Ser Lys
100 105 110

Ala Glu Gly Arg Thr Asn Val Ala Ile Gly Tyr Arg Ala His Ser Gly
115 120 125

Thr Gly Leu His Gly Val Ala Val Gly Tyr Asn Ser Leu Ser Ser Ala
130 135 140

Asn Ser Val Thr Leu Gly Gly Asn Thr Lys Ala Ala Gly Ala Asn Ser
145 150 155 160

Val Ala Ile Gly Asn Ser Val Gln Ile Thr Gly Ser Asn Ser Val Val
165 170 175

Val Gly Ser Gln Ile Ile Asp Met Thr Gly Glu Asn Leu Val Ala Ile
180 185 190

Gly His Gly Ala Ser Ala Gly Asn Tyr Ser Thr Ala Phe Gly Tyr Arg
195 200 205

Ala Ser Ala Asn Gly Ile Gly Ser Val Ala Val Gly Asp Arg Ala Asn
210 215 220

Thr Asn Gln Thr Ser Arg Ala Thr Ala Leu Gly Asn Asn Ser Ile Val
225 230 235 240

Leu Val Gly Gly Gly Val Ala Leu Gly Tyr Gly Ser Thr Ala Gln Thr
245 250 255

Asn Gly Gly Ile Asp Gly Val Arg Gln Ser His Ser Val Ile Thr Asp
260 265 270

Ala Ser Thr Val Asn Asn Gly Phe Lys Ser Thr Gln Ser Val Asp Asp
275 280 285

Ser Pro Glu Gly His Pro Lys Gly Ser Asn Asp Phe Leu Ile Gly Ala

-continued

```
    290                 295                 300

Val Ser Val Gly Asn Asn Lys Ile Lys Arg Gln Ile Val Asn Val Ala
305                 310                 315                 320

Ala Gly Lys Asp Leu Thr Asp Ala Val Asn Val Ala Gln Leu Gln Ser
                325                 330                 335

Leu Thr Met Lys Ile Gly Gly Asp Ser Asn Ala Glu Glu Gln Pro Lys
            340                 345                 350

Val Gly Leu Trp Ala Gly Thr Leu Asn Val Lys Gly Glu Asn Gly Leu
        355                 360                 365

Thr Ser Glu Ala Ser Gly Asp Thr Ile Thr Val Lys Leu Thr Asp Asp
    370                 375                 380

Ile Lys Arg Lys Ile Asp Asn Ala Ala Glu Pro Gly Thr Phe His Phe
385                 390                 395                 400

Asn Thr Asp Gly Lys Leu Ser Met Gly Asn Pro Gly Val Ala Thr Ile
                405                 410                 415

Gln Thr Val Val Asn Ala Val Asn Asn Ala Gly Trp Lys Leu Asn Val
            420                 425                 430

Thr Gln Arg Asp Gly Gly Gln Gly Thr Ser Ile His Phe Asp Pro Tyr
        435                 440                 445

Leu Ile Lys Met Gly Glu Thr Val Thr Phe Ile Ala Gly Asn Asn Ile
    450                 455                 460

Lys Leu Gln Gln Thr Asn Glu Asn Ile Thr Ile Ser Thr Leu Gly Lys
465                 470                 475                 480

Leu Ile Lys Glu Thr Gln Thr Leu Ala Gly Gly Gly Leu Lys Ile Thr
                485                 490                 495

Tyr Thr Asp Asn Thr Ser Asp Thr Ile Ser Gly Gly Ala Pro Gly Pro
            500                 505                 510

Ala Gly Pro Val Gly Pro Arg Gly Pro Ala Gly Pro Lys Gly Glu Arg
        515                 520                 525

Gly Glu Pro Gly Pro Arg Gly Glu Arg Gly Glu Gln Gly Leu Thr Gly
    530                 535                 540

Pro Ala Gly Pro Gln Gly Val Pro Gly Pro Ala Gly Pro Val Gly Pro
545                 550                 555                 560

Ala Gly Glu Arg Gly Pro Ala Gly Pro Val Gly Pro Val Gly Pro Arg
                565                 570                 575

Gly Pro Ala Gly Glu Thr Gly Pro Arg Gly Glu Arg Gly Glu Gln Gly
            580                 585                 590

Leu Gln Gly Ala Thr Gly Pro Ala Gly Pro Ala Gly Ala Pro Gly Val
        595                 600                 605

Ala Gly Pro Lys Gly Asp Arg Gly Glu Ala Gly Pro Lys Gly Glu Ala
    610                 615                 620

Gly Pro Thr Gly Pro Arg Gly Glu Arg Gly Pro Ala Gly Asp Lys Gly
625                 630                 635                 640

Asp Lys Gly Asp Thr Gly Pro Met Gly Pro Pro Gly Pro Val Gly Pro
                645                 650                 655

Ala Gly Pro Thr Gly Pro Glu Gly Pro Arg Gly Glu Lys Gly Pro Lys
            660                 665                 670

Gly Glu Gln Gly Asp Gln Gly Leu Lys Gly Glu Thr Gly Pro Ala Gly
        675                 680                 685

Pro Ala Gly Pro Ala Gly Pro Val Gly Pro Val Gly Pro Gln Gly Ala
    690                 695                 700

Lys Gly Glu Gln Gly Pro Arg Gly Glu Arg Gly Glu Gln Gly Ala Ala
705                 710                 715                 720
```

-continued

```
Gly Pro Thr Gly Pro Gln Gly Ala Pro Gly Pro Val Gly Pro Ala Gly
            725                 730                 735

Ala Ala Gly Pro Ala Gly Pro Arg Gly Pro Lys Gly Asp Pro Gly Gln
        740                 745                 750

Lys Gly Asp Ala Gly Leu Gln Gly Pro Ala Gly Glu Arg Gly Glu Arg
    755                 760                 765

Gly Pro Glu Gly Pro Gln Gly Pro Arg Gly Glu Arg Gly Glu Pro Gly
    770                 775                 780

Ala Pro Gly Pro Met Gly Pro Gln Gly Pro Gln Gly Lys Glu Gly Pro
785                 790                 795                 800

Val Gly Pro Arg Gly Pro Ala Gly Pro Ala Gly Glu Gln Gly Pro Ala
            805                 810                 815

Gly Pro Arg Gly Glu Lys Gly Leu Lys Gly Asp Lys Gly Glu Gln Gly
        820                 825                 830

Asp Arg Gly Pro Thr Gly Glu Ala Gly Pro Lys Gly Glu Ala Gly Pro
    835                 840                 845

Ala Gly Ala Lys Gly Asp Gln Gly Pro Pro Gly Glu Arg Gly Glu Arg
    850                 855                 860

Gly Pro Ala Gly Ala Thr Gly Gln Thr Gly Pro Ala Gly Pro Arg Gly
865                 870                 875                 880

Pro Lys Gly Asp Pro Gly Gln Lys Gly Asp Ala Gly Leu Gln Gly Pro
            885                 890                 895

Ala Gly Glu Arg Gly Glu Arg Gly Glu Thr Gly Glu Arg Gly Pro Ala
        900                 905                 910

Gly Pro Val Gly Pro Val Gly Pro Arg Gly Pro Ala Gly Glu Thr Gly
    915                 920                 925

Pro Arg Gly Glu Arg Gly Glu Gln Gly Leu Gln Gly Ala Thr Gly Pro
    930                 935                 940

Ala Gly Pro Pro Gly Pro Ala Gly Ala Arg Gly Glu Ala Gly Pro Arg
945                 950                 955                 960

Gly Glu Arg Gly Glu Pro Gly Leu Ala Gly Pro Thr Gly Pro Gln Gly
            965                 970                 975

Ala Pro Gly Pro Val Gly Pro Ala Gly Ala Ala Gly Pro Ala Gly Pro
        980                 985                 990

Arg Gly Pro Lys Gly Asp Pro Gly  Gln Lys Gly Asp Ala  Gly Leu Gln
    995                  1000                1005

Gly Pro  Met Gly Pro Ala Gly  Pro Ala Gly Ala Ile  Gly Pro Ala
    1010                 1015                1020

Gly Pro  Ala Gly Pro Lys Gly  Asp Gln Gly Leu Val  Gly Pro Gln
    1025                 1030                1035

Gly Pro  Thr Gly Ala Lys Gly  Glu Gln Gly Pro Arg  Gly Glu Pro
    1040                 1045                1050

Gly Ile  Gln Gly Pro Arg Gly  Glu Ala Gly Pro Lys  Gly Glu Val
    1055                 1060                1065

Gly Pro  Ala Gly Pro Thr Gly  Pro Thr Gly Ala Arg  Gly Glu Lys
    1070                 1075                1080

Gly Asp  Thr Gly Pro Ala Gly  Pro Ala Gly Ala Gln  Gly Glu Gln
    1085                 1090                1095

Gly Pro  Ile Gly Pro Ala Gly  Pro Lys Gly Asp Lys  Gly Glu Gln
    1100                 1105                1110

Gly Asp  Gln Gly Pro Arg Gly  Glu Ala Gly Pro Ala  Gly Pro Gln
    1115                 1120                1125

Gly Pro  Ala Gly Ala Thr Gly  Pro Glu Gly Pro Val  Gly Pro Thr
    1130                 1135                1140
```

```
Gly Pro  Ala Gly Pro Thr Gly  Pro Lys Gly Asp Thr  Gly Pro Glu
    1145                 1150                 1155

Gly Pro  Lys Gly Glu Gln Gly  Pro Val Gly Pro Gln  Gly Pro Thr
    1160                 1165                 1170

Gly Ala  Lys Asp Leu Thr Asn  Leu Asn Ser Val Thr  Leu Gly Thr
    1175                 1180                 1185

Ala Thr  Met Thr Gly Asp Lys  Asn Thr Ile Asn Leu  Thr Gly Ala
    1190                 1195                 1200

Gly Glu  Lys Val Glu Glu Glu  Phe Val Lys Trp Asp  Pro Val Thr
    1205                 1210                 1215

Lys Gln  Pro Ile Tyr Asp Lys  Asp Gly Asn Leu Gln  Lys Tyr Lys
    1220                 1225                 1230

Glu Lys  Val Asp Pro Arg Val  Lys Leu Ser Gly Ile  Ala Asp Gly
    1235                 1240                 1245

Asp Ile  Ser Pro Asn Ser Thr  Asp Ala Val Asn Gly  Arg Gln Val
    1250                 1255                 1260

Tyr Ala  Leu Thr Asn Gly Asn  Gln Val Glu Gln Lys  Lys Asp Gly
    1265                 1270                 1275

Ser Thr  Val Thr Tyr Ala Lys  Asp Lys Asp Gly Ser  Val Ile Thr
    1280                 1285                 1290

Glu Val  Lys Arg Asp Lys Asn  Gly Asn Pro Glu Leu  Asp Ala Asp
    1295                 1300                 1305

Gly Asn  Glu Ile Val Gln Ala  Lys Glu Tyr Thr Leu  Thr Thr Tyr
    1310                 1315                 1320

Asn Val  Lys Gly Gln Thr Glu  Phe Val Thr Asn Ser  Val Ile Thr
    1325                 1330                 1335

Ala Ile  His Asn Met Asn Glu  Gln Gly Ile Lys Phe  Phe His Thr
    1340                 1345                 1350

Asn Asp  Gly Val Ala Glu Pro  Ile Asn Gln Ala Ser  Asn Asp Ile
    1355                 1360                 1365

Asp Ser  Ser Ala Ser Gly Thr  Tyr Ala Thr Ala Ile  Gly Tyr Lys
    1370                 1375                 1380

Ala Val  Ala Ala Gly Asp Asn  Ala Leu Ala Ile Gly  Lys Gly Ala
    1385                 1390                 1395

Thr Ala  Ser Gly Lys Asn Ser  Ile Ala Ile Gly Thr  Gly Asn Gln
    1400                 1405                 1410

Val Ile  Ala Asn Lys Ser Gly  Ala Phe Gly Asp Pro  Asn Ile Ile
    1415                 1420                 1425

Arg Gly  Val Gln Ile Gly Thr  Asp Ser Ala Gly Asn  Pro Ile Tyr
    1430                 1435                 1440

Lys Gly  Ile Asp Gly Ser Tyr  Ala Phe Gly Asn Asp  Asn Val Ile
    1445                 1450                 1455

Thr Ser  Ser Asn Thr Phe Val  Leu Gly Asn Asn Val  Asn Asn Lys
    1460                 1465                 1470

Arg Asp  Ser Asn Gly Ala Leu  Thr Trp Met Ser Ala  Thr Pro Glu
    1475                 1480                 1485

Gly Thr  Val Glu Asn Ser Val  Tyr Leu Gly Asn Asn  Thr Thr Ala
    1490                 1495                 1500

Thr Ala  Gly Asp Gly Ser Gln  Thr Gly Ser Leu Lys  Asn Trp Lys
    1505                 1510                 1515

Gln Asp  Gly Ser Arg Gly Ser  Thr Thr Thr Ala Gly  Ser Thr Gly
    1520                 1525                 1530

Thr Val  Ser Ser Val Thr Val  Gly Asn Met Ile Tyr  Asp Gly Phe
```

```
    1535                1540                1545

Ala Gly  Ala Thr Ala Asn Gly  Val Val Ser Val Gly  Ala Ala Gly
    1550                1555                1560

Asp Glu  Arg Arg Ile Gln Asn  Val Ala Thr Gly Glu  Ile Ser Ser
    1565                1570                1575

Thr Ser  Thr Asp Ala Ile Asn  Gly Ser Gln Leu Tyr  Asn Val Ala
    1580                1585                1590

His Arg  Leu Gly Ala Lys Leu  Glu Arg Glu Gly Arg  Gln Leu Arg
    1595                1600                1605

Ala Gly  Ile Ala Ala Thr Thr  Ala Met Ser Asn Ile  Pro Gln Val
    1610                1615                1620

Thr Leu  Pro Gly Lys Ser Thr  Leu Gly Ala Gly Ile  Gly Thr Phe
    1625                1630                1635

Glu Gly  Gln Asn Ala Val Ala  Val Gly Phe Ser Arg  Met Ser Asp
    1640                1645                1650

Asn Gly  Arg Val Ile Leu Lys  Val Ser Ala Gly Ala  Thr Ser Gln
    1655                1660                1665

Gly Lys  Tyr Asn Ala Gly Ala  Gly Ile Ala Leu Gln  Trp
    1670                1675                1680


<210> SEQ ID NO 19
<211> LENGTH: 3216
<212> TYPE: DNA
<213> ORGANISM: Haemophilus parasuis

<400> SEQUENCE: 19

atgaataaaa tatttagagt tatttggagt catgatcaac aggcttgggt agttgtatct     60

gagttagtaa agtctcatac caaaacatcc gcttgcacgg ataaaagagc tcaagtatgc    120

acctcacatt attttttaga taaacagcaa gataaattta aattaagtct tttaagtcta    180

gtattactag gtatattttt tagtccaccg gcaggttcag ctactcactc aggaacacca    240

tatactgcag atggtggtag tagatcgaat ttaggatctg acgacggtac tattagtatt    300

ggtaaagaga gtaaggcttc gtatggtgct attgctatcg gtcagaggtc aaaagctgaa    360

ggtaggcatg gtattgcgat aggttatcaa acaaatgcag gaacacacgt aaactctgtt    420

gcggtaggca acgatattcg agtaagtggg gaggaagcag ttgccatcgg gagtagttca    480

aaagcgggaa agggatctgt tgtcttaggc agacaagccg atgcggcaaa tattgaacaa    540

gcagttgtaa taggtaacct tgctaaagca agtaaggcac aatctattgc tatcggggca    600

aataccaaag cggaggggta tggctccata tcaatcggtg gagatgattt aaaaacaacg    660

aaatatcaaa ctggtaatca aggccaatcc aaaacaacaa ctgcgaaagg taaagcctct    720

gttgctattg gggggctgtc tttggctacg ggcgacggat ctattgttgt aggtccttta    780

gcatctgcaa gtcatgttga aggcattgct atcggtgcga gaagtaagtc taccaatgag    840

tacggtattg cggttggtgg tggtgcaact gctggaaaaa acgccgttgc tgttggtagg    900

gactcgaacg gtggtgggac agattccatt gcgataggta attctgcgaa aacaacaggg    960

gcagactctg ttgttgtggg tgccaatatc aatgtgacag gtgaaaaatt agtggcaatt   1020

ggacgcgaag caaattctgg aagtcattct actgccttgg gttataaagc ctctgccggt   1080

ggtatgcact ctgttgctgt gggtgaaagt gccatgacaa atgatggtgc tgctagagca   1140

accgcacttg gtaataatac cgttgtcacc gtgggtggcg gtgtggcatt aggttatggg   1200

tctaatgcaa gtacagctgg cggtgtagag gggttaaaac aaactcattc tgtcacaacg   1260

gaaggaagca ctgtcgctaa cggctttaaa tcaacacaaa gtgttgataa taatgctatt   1320
```

-continued ggtgcggttt ctgtcggtgg aggctcaggt aataaactca tcaatcgcca aatcactaat 1380
gttgcggcag gtaaagaatt aaccgatgcg gtaaacgtgg cacagcttaa atctttaacc 1440
ctgaaaattg agggaaatga gaataagcat aacggtgtaa atgctaattt aagcagtgct 1500
gacagaccta aagtcggctt gtggagtggt acgctcaagg taaaaggcga caacggtctt 1560
acttcccatg ctagtggcga tacgattacg gttaaattaa ccgatgatac taaaagcaaa 1620
attgataaga ttgacaattt aggttggaaa cttaaaattg ctcagggaat gggggtaaa 1680 gcaacaaatc cacctacgga acatcttgtc aaaatgagcg atacggcaac cgtaaccttt 1740
accgctggaa ataatattaa attagaacaa acgaacggaa atattacgat ttctacgatt 1800
ggtaagttaa ttaaagagac taaaatggta aatggtaatt tgcaaattac ttatacggat 1860
ggcagcagta atactattac taggggagag aaaggagata caggtcctag aggtgaaact 1920
ggccctgcgg gtccacctgg tcctatgggt ccagcagggg ctgctggtcc agcaggggct 1980
gctggtctag taggaccaat gggccctcaa ggtcctgcgg gtccacctgg tcctgtgggt 2040
ccagcagggg ctgctggtcc taagggggat aaaggcgaac caggacaagc gggtccagca 2100
ggtcctagag gtgaaccagg acaagcgggt ccagcaggac cacgaggccc tgcgggtcct 2160
aaaggagatg caggtccaaa aggtgataca ggtcagagag gtgaaactgg ccctgcgggt 2220
ccagcgggac caaagggtga accgggtcct aaaggtgaac aaggtattcc aggccctgcg 2280
ggtccaacgg gacctaaggg tgacaaaggt gatacgggtc cagcaggacc acaaggccct 2340
gcgggtccaa cgggaccaca aggccctgcg ggtccagcag gggctaaggg tgacaaaggt 2400
gatacgggtc cagcaggacc acaaggacct acgggtccaa cgggatcaca agaccctgcg 2460
ggtccaactg gaaattcgga attaaaaggc attacgtcga tagccaatgg taacgacgcc 2520
accaaggcga atggggctaa gattaccttg tctgcagatt ctacagataa aacagttaat 2580
gttaatgatg cgaaaattac caatgtggcg gctggtacag cagatactga tgcggtaaat 2640
gtgagccagt taaatactaa ggcagcagct tcaaaaacag aggttgaagc gggtaaaaat 2700
gtgaaagtga cttcaaaaac gggggcaaat ggtcagaata tttacaatgt gagcgtgtct 2760
ggagatttaa gcgacattac ttcaattagt aatggcgata cgaaagtatc tttaggtaaa 2820
gataagcaag gaaatccagt tgtaaatatg aatggtgcca gaattaccaa cgttggagat 2880
ggtagtgctg agggcgatat tgtgaatgtt cgtcagctca acaaagtggt ttcttctgtg 2940
aatacaggat ttaatcaatt atcaagagat attggtcgtg ttgatgttaa tgcaagagcg 3000
ggtattgctt ctgctggggc gatggctaat ttgccacaaa tttctttacc aggtaaaagt 3060
gctatttctg tttctaatgc acaatatcgc gggcaatctg cctatgctat aggttattcc 3120
agaatttctg ataatggcaa atggcttatt cgagcgtctg ttagcagtaa tactcagcgg 3180
gatactatga ttggaggagg ggtaggtttt gtgtgg 3216

<210> SEQ ID NO 20
<211> LENGTH: 1072
<212> TYPE: PRT
<213> ORGANISM: haemophilus parasuis

<400> SEQUENCE: 20

Met Asn Lys Ile Phe Arg Val Ile Trp Ser His Asp Gln Gln Ala Trp
1 5 10 15

Val Val Val Ser Glu Leu Val Lys Ser His Thr Lys Thr Ser Ala Cys
20 25 30

Thr Asp Lys Arg Ala Gln Val Cys Thr Ser His Tyr Phe Leu Asp Lys

-continued

```
        35                  40                  45

Gln Gln Asp Lys Phe Lys Leu Ser Leu Leu Ser Leu Val Leu Leu Gly
    50                  55                  60

Ile Phe Phe Ser Pro Pro Ala Gly Ser Ala Thr His Ser Gly Thr Pro
65                  70                  75                  80

Tyr Thr Ala Asp Gly Gly Ser Arg Ser Asn Leu Gly Ser Asp Asp Gly
                85                  90                  95

Thr Ile Ser Ile Gly Lys Glu Ser Lys Ala Ser Tyr Gly Ala Ile Ala
            100                 105                 110

Ile Gly Gln Arg Ser Lys Ala Glu Gly Arg His Gly Ile Ala Ile Gly
        115                 120                 125

Tyr Gln Thr Asn Ala Gly Thr His Val Asn Ser Val Ala Val Gly Asn
    130                 135                 140

Asp Ile Arg Val Ser Gly Glu Glu Ala Val Ala Ile Gly Ser Ser Ser
145                 150                 155                 160

Lys Ala Gly Lys Gly Ser Val Val Leu Gly Arg Gln Ala Asp Ala Ala
                165                 170                 175

Asn Ile Glu Gln Ala Val Val Ile Gly Asn Leu Ala Lys Ala Ser Lys
            180                 185                 190

Ala Gln Ser Ile Ala Ile Gly Ala Asn Thr Lys Ala Glu Gly Tyr Gly
        195                 200                 205

Ser Ile Ser Ile Gly Gly Asp Asp Leu Lys Thr Thr Lys Tyr Gln Thr
    210                 215                 220

Gly Asn Gln Gly Gln Ser Lys Thr Thr Thr Ala Lys Gly Lys Ala Ser
225                 230                 235                 240

Val Ala Ile Gly Gly Leu Ser Leu Ala Thr Gly Asp Gly Ser Ile Val
                245                 250                 255

Val Gly Pro Leu Ala Ser Ala Ser His Val Glu Gly Ile Ala Ile Gly
            260                 265                 270

Ala Arg Ser Lys Ser Thr Asn Glu Tyr Gly Ile Ala Val Gly Gly Gly
        275                 280                 285

Ala Thr Ala Gly Lys Asn Ala Val Ala Val Gly Arg Asp Ser Asn Gly
    290                 295                 300

Gly Gly Thr Asp Ser Ile Ala Ile Gly Asn Ser Ala Lys Thr Thr Gly
305                 310                 315                 320

Ala Asp Ser Val Val Val Gly Ala Asn Ile Asn Val Thr Gly Glu Lys
                325                 330                 335

Leu Val Ala Ile Gly Arg Glu Ala Asn Ser Gly Ser His Ser Thr Ala
            340                 345                 350

Leu Gly Tyr Lys Ala Ser Ala Gly Gly Met His Ser Val Ala Val Gly
        355                 360                 365

Glu Ser Ala Met Thr Asn Asp Gly Ala Ala Arg Ala Thr Ala Leu Gly
    370                 375                 380

Asn Asn Thr Val Val Thr Val Gly Gly Gly Val Ala Leu Gly Tyr Gly
385                 390                 395                 400

Ser Asn Ala Ser Thr Ala Gly Gly Val Glu Gly Leu Lys Gln Thr His
                405                 410                 415

Ser Val Thr Thr Glu Gly Ser Thr Val Ala Asn Gly Phe Lys Ser Thr
            420                 425                 430

Gln Ser Val Asp Asn Asn Ala Ile Gly Ala Val Ser Val Gly Gly Gly
        435                 440                 445

Ser Gly Asn Lys Leu Ile Asn Arg Gln Ile Thr Asn Val Ala Ala Gly
    450                 455                 460
```

-continued

```
Lys Glu Leu Thr Asp Ala Val Asn Val Ala Gln Leu Lys Ser Leu Thr
465                 470                 475                 480

Leu Lys Ile Glu Gly Asn Glu Asn Lys His Asn Gly Val Asn Ala Asn
                485                 490                 495

Leu Ser Ser Ala Asp Arg Pro Lys Val Gly Leu Trp Ser Gly Thr Leu
            500                 505                 510

Lys Val Lys Gly Asp Asn Gly Leu Thr Ser His Ala Ser Gly Asp Thr
        515                 520                 525

Ile Thr Val Lys Leu Thr Asp Asp Thr Lys Ser Lys Ile Asp Lys Ile
    530                 535                 540

Asp Asn Leu Gly Trp Lys Leu Lys Ile Ala Gln Gly Met Gly Gly Lys
545                 550                 555                 560

Ala Thr Asn Pro Pro Thr Glu His Leu Val Lys Met Ser Asp Thr Ala
                565                 570                 575

Thr Val Thr Phe Thr Ala Gly Asn Asn Ile Lys Leu Glu Gln Thr Asn
            580                 585                 590

Gly Asn Ile Thr Ile Ser Thr Ile Gly Lys Leu Ile Lys Glu Thr Lys
        595                 600                 605

Met Val Asn Gly Asn Leu Gln Ile Thr Tyr Thr Asp Gly Ser Ser Asn
    610                 615                 620

Thr Ile Thr Arg Gly Glu Lys Gly Asp Thr Gly Pro Arg Gly Glu Thr
625                 630                 635                 640

Gly Pro Ala Gly Pro Pro Gly Pro Met Gly Pro Ala Gly Ala Ala Gly
                645                 650                 655

Pro Ala Gly Ala Ala Gly Leu Val Gly Pro Met Gly Pro Gln Gly Pro
            660                 665                 670

Ala Gly Pro Pro Gly Pro Val Gly Pro Ala Gly Ala Ala Gly Pro Lys
        675                 680                 685

Gly Asp Lys Gly Glu Pro Gly Gln Ala Gly Pro Ala Gly Pro Arg Gly
    690                 695                 700

Glu Pro Gly Gln Ala Gly Pro Ala Gly Pro Arg Gly Pro Ala Gly Pro
705                 710                 715                 720

Lys Gly Asp Ala Gly Pro Lys Gly Asp Thr Gly Gln Arg Gly Glu Thr
                725                 730                 735

Gly Pro Ala Gly Pro Ala Gly Pro Lys Gly Glu Pro Gly Pro Lys Gly
            740                 745                 750

Glu Gln Gly Ile Pro Gly Pro Ala Gly Pro Thr Gly Pro Lys Gly Asp
        755                 760                 765

Lys Gly Asp Thr Gly Pro Ala Gly Pro Gln Gly Pro Ala Gly Pro Thr
    770                 775                 780

Gly Pro Gln Gly Pro Ala Gly Pro Ala Gly Ala Lys Gly Asp Lys Gly
785                 790                 795                 800

Asp Thr Gly Pro Ala Gly Pro Gln Gly Pro Thr Gly Pro Thr Gly Ser
                805                 810                 815

Gln Asp Pro Ala Gly Pro Thr Gly Asn Ser Glu Leu Lys Gly Ile Thr
            820                 825                 830

Ser Ile Ala Asn Gly Asn Asp Ala Thr Lys Ala Asn Gly Ala Lys Ile
        835                 840                 845

Thr Leu Ser Ala Asp Ser Thr Asp Lys Thr Val Asn Val Asn Asp Ala
    850                 855                 860

Lys Ile Thr Asn Val Ala Ala Gly Thr Ala Asp Thr Asp Ala Val Asn
865                 870                 875                 880

Val Ser Gln Leu Asn Thr Lys Ala Ala Ala Ser Lys Thr Glu Val Glu
                885                 890                 895
```

-continued

```
Ala Gly Lys Asn Val Lys Val Thr Ser Lys Thr Gly Ala Asn Gly Gln
            900                 905                 910

Asn Ile Tyr Asn Val Ser Val Ser Gly Asp Leu Ser Asp Ile Thr Ser
        915                 920                 925

Ile Ser Asn Gly Asp Thr Lys Val Ser Leu Gly Lys Asp Lys Gln Gly
    930                 935                 940

Asn Pro Val Val Asn Met Asn Gly Ala Arg Ile Thr Asn Val Gly Asp
945                 950                 955                 960

Gly Ser Ala Glu Gly Asp Ile Val Asn Val Arg Gln Leu Asn Lys Val
                965                 970                 975

Val Ser Ser Val Asn Thr Gly Phe Asn Gln Leu Ser Arg Asp Ile Gly
            980                 985                 990

Arg Val Asp Val Asn Ala Arg Ala  Gly Ile Ala Ser Ala  Gly Ala Met
        995                 1000                 1005

Ala Asn  Leu Pro Gln Ile Ser  Leu Pro Gly Lys Ser  Ala Ile Ser
    1010                 1015                 1020

Val Ser  Asn Ala Gln Tyr Arg  Gly Gln Ser Ala Tyr  Ala Ile Gly
    1025                 1030                 1035

Tyr Ser  Arg Ile Ser Asp Asn  Gly Lys Trp Leu Ile  Arg Ala Ser
    1040                 1045                 1050

Val Ser  Ser Asn Thr Gln Arg  Asp Thr Met Ile Gly  Gly Gly Val
    1055                 1060                 1065

Gly Phe  Val Trp
    1070
```

<210> SEQ ID NO 21
<211> LENGTH: 3297
<212> TYPE: DNA
<213> ORGANISM: Haemophilus parasuis

<400> SEQUENCE: 21

```
atgaataaaa tatttagagt tatttggagt catgctcaac aggcttgggt ggttgtgtct     60

gagttagtaa agtctcacac caaaacatcc gcttacacgg ataaaagagc tcaagtatgc    120

acctcagatt attttttaga taaacagcaa gataaattta aattaagtct tttaagtcta    180

gtattactaa gtatattttt tagtccagta gcagtaggtg cacaacttca cacaggaaca    240

ccatatactg caggtggtgg tagtaaatcg gatagaggat ctgacgacgg tactattagt    300

attggtaaaa agagtaaggc ttcgtatggt gctattgcta tcggtgagga gtcaaaagct    360

gaagctaggc ataatgttgc gataggttat aaagcagatt caggaacaga cgcaaactct    420

attacgatag gctacaatac taaagtaagt ggggagcaag gaattgccat cgggaaacag    480

tcaaaagcgg gagggagatc tgttgtctta ggcggaggtg ccgaagggac aactactcaa    540

acagttgtaa taggtaacct tgctaaagca actgggtcac aatctattgc tatcggggca    600

aataccaaag cggaggggta tggctccata tcaatcggtg gagatgattt agatagcacg    660

gcttatcacg ataataatag tacaaaacag acccgccaaa caacaactgc gaaaggtaaa    720

gcctctgttg ctattggggg tctgtctttg gctacgggcg acggatctac tgttttaggt    780

cctttagcat ctgcaagtca tgttgaaggc attgctatcg gtgcgagaag taagtctacc    840

aatgagtacg gtattgcggt tggtggtagt gcaactgctg gaaaaaacgc cgttgctgtt    900

ggtagggact cgaaaggtgc tgggacagat tccattgcga taggtaattc tgcgaaaaca    960

acaggggcag actctgttgt tgtgggtgcc agtatcaatg tgacaggtga aaaattagtg   1020

gcaattggac gccaagcaaa tgctggaagt cattctactg ccttgggtta taaagcctct   1080
```

gccggtggta tgcactctgt tgctgtgggt gaaagtgcca tgacaaatga tggtgctgct 1140
agagcaaccg cacttggtaa taataccgtt gtcaccgtgg gtggcggtgt ggcattgggt 1200
tatgggtcaa gagcagaaac gagagggggt attgaaggag caaaacaaac ttattctgtc 1260
acaacgggag gaagcactgt cgagaacggc tttaaatcaa cagaaaatgt tgatggtaat 1320
aatattggtg cagtttctgt cggtggaggc tcaggtaata aactcatcaa tcgccaaatc 1380
accaacgttg cggctggtaa agaattaacc gatgcagtaa acgtggcaca gcttaaatct 1440
ttaacgatga aaattgcagg ggatacaggc aattctgata atgagaaagt gggtatttgg 1500
gaaggtacgc ttaaagtgct aggtacaagc ggtgagatta agacttccgc aagcaatgat 1560
accatcacat tgaaattaga tgaaacattg aaaaataaaa ttgataagat tgacaattta 1620
ggttggaaac ttaaaattgc tcagggaatg gggggtaaag caacaaatcc acctgcggaa 1680
cagcttatca aaatggacca gaccgtaacc tttaccgctg gaaagaatat taaattagaa 1740
caagcgggcg gaaatattac gatttctacg attggtaagt taattgaaaa gactgaatgg 1800
aaaaatggta atttgcaaat tacttatacg gatggcagct ctgatactat tgctaagggg 1860
aaagacggta aaaatggtga gaaaggtgat agaggggaac cgggtcctag aggtgaacca 1920
ggtattccag gacctgcggg tccagtaggt cctatgggtc cagcaggggc tgctggtcta 1980
gtaggaccaa tgggccctca aggtcctgcg ggtccacctg gtcctgtggg tccagcaggg 2040
gctgctggtc ctaaggggga taaaggcgaa ccaggacaag cgggtccagc aggaccacga 2100
ggccctgcgg gtccaaaagg tgatacaggt cagagaggtg aaactggctc tgcgggtcca 2160
gcgggaccaa agggtgaacc gggtcctaaa ggtgaacaag gtattccagg acaagcgggt 2220
ccagcaggac cacgaggacc gcagggaaca gcgggtgctc agggacctaa gggggataaa 2280
ggcgaaccag gagaagcggg tccagcagga ccacgaggcc ctgcgggtcc taaaggagat 2340
gcaggtccaa aaggtgatac aggtcagaga ggtgaaactg gctctgcggg tccaacggga 2400
cctaagggtg aaccgggtcc taaaggtgaa caaggtattc caggccctgc gggtccagcg 2460
ggacctaagg gtgacaaagg tgatacgggt ccagcgggac cacaaggtcc tgcgggtcca 2520
acgggaccac aagaccctgc gggtccaact ggaaattcgg aattaaaagg cattacctcg 2580
attgccaatg gtaacgacgc caccaaggcg aatggggcta agattacctt gtctgcaggt 2640
tctacagata aaacagttaa tgttaatgat gcgaaaatta ccaatgtggc ggctggtaca 2700
gcagatactg atgcggtgaa tgtgagccag ttaaatacta aggcagcagc ttcaaaaaca 2760
gaggttgaag cgggtaaaaa tgtgaaagtg acttcaaaaa cgggggcaaa tggtcagaat 2820
atttacaatg tgagcgtgtc tggagattta agcgacatta cttcaattag taatggcgat 2880
acgaaagtat ctttaggtaa agataagcaa ggaaatccag ttgtaaatat gaatggtgcc 2940
agaattacca acgttggaga tggtagtgct gagggcgata ttgtgaatgt gcgtcagctc 3000
aacaaagtgg tttcttctgt gaatacagga tttaatcaat tatcaagaga tattggtcgt 3060
gttgatgtta atgcaagagc ggggattgct tctgctgggg cgatggctaa tttgccacaa 3120
atttctttac caggtaaaag tgctatttct gtttctaatg cacaatatcg cgggcaatct 3180
gcctatgcta taggttattc cagaatttct gataatggca aatggcttat tcgagcgtct 3240
gttagcagta atactcagcg ggatactatg attggaggag ggtaggttt tgtgtgg 3297

<210> SEQ ID NO 22
<211> LENGTH: 1099
<212> TYPE: PRT
<213> ORGANISM: haemophilus parasuis

<400> SEQUENCE: 22

```
Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Ser
    50                  55                  60

Ile Phe Phe Ser Pro Val Ala Val Gly Ala Gln Leu His Thr Gly Thr
65                  70                  75                  80

Pro Tyr Thr Ala Gly Gly Gly Ser Lys Ser Asp Arg Gly Ser Asp Asp
                85                  90                  95

Gly Thr Ile Ser Ile Gly Lys Lys Ser Lys Ala Ser Tyr Gly Ala Ile
            100                 105                 110

Ala Ile Gly Glu Glu Ser Lys Ala Glu Ala Arg His Asn Val Ala Ile
        115                 120                 125

Gly Tyr Lys Ala Asp Ser Gly Thr Asp Ala Asn Ser Ile Thr Ile Gly
    130                 135                 140

Tyr Asn Thr Lys Val Ser Gly Glu Gln Gly Ile Ala Ile Gly Lys Gln
145                 150                 155                 160

Ser Lys Ala Gly Gly Arg Ser Val Val Leu Gly Gly Gly Ala Glu Gly
                165                 170                 175

Thr Thr Thr Gln Thr Val Val Ile Gly Asn Leu Ala Lys Ala Thr Gly
            180                 185                 190

Ser Gln Ser Ile Ala Ile Gly Ala Asn Thr Lys Ala Glu Gly Tyr Gly
        195                 200                 205

Ser Ile Ser Ile Gly Gly Asp Asp Leu Asp Ser Thr Ala Tyr His Asp
    210                 215                 220

Asn Asn Ser Thr Lys Gln Thr Arg Gln Thr Thr Thr Ala Lys Gly Lys
225                 230                 235                 240

Ala Ser Val Ala Ile Gly Gly Leu Ser Leu Ala Thr Gly Asp Gly Ser
                245                 250                 255

Thr Val Leu Gly Pro Leu Ala Ser Ala Ser His Val Glu Gly Ile Ala
            260                 265                 270

Ile Gly Ala Arg Ser Lys Ser Thr Asn Glu Tyr Gly Ile Ala Val Gly
        275                 280                 285

Gly Ser Ala Thr Ala Gly Lys Asn Ala Val Ala Val Gly Arg Asp Ser
    290                 295                 300

Lys Gly Ala Gly Thr Asp Ser Ile Ala Ile Gly Asn Ser Ala Lys Thr
305                 310                 315                 320

Thr Gly Ala Asp Ser Val Val Val Gly Ala Ser Ile Asn Val Thr Gly
                325                 330                 335

Glu Lys Leu Val Ala Ile Gly Arg Gln Ala Asn Ala Gly Ser His Ser
            340                 345                 350

Thr Ala Leu Gly Tyr Lys Ala Ser Ala Gly Gly Met His Ser Val Ala
        355                 360                 365

Val Gly Glu Ser Ala Met Thr Asn Asp Gly Ala Ala Arg Ala Thr Ala
    370                 375                 380

Leu Gly Asn Asn Thr Val Val Thr Val Gly Gly Gly Val Ala Leu Gly
385                 390                 395                 400

Tyr Gly Ser Arg Ala Glu Thr Arg Gly Gly Ile Glu Gly Ala Lys Gln
                405                 410                 415
```

-continued

```
Thr Tyr Ser Val Thr Thr Gly Gly Ser Thr Val Glu Asn Gly Phe Lys
            420                 425                 430

Ser Thr Glu Asn Val Asp Gly Asn Asn Ile Gly Ala Val Ser Val Gly
        435                 440                 445

Gly Gly Ser Gly Asn Lys Leu Ile Asn Arg Gln Ile Thr Asn Val Ala
    450                 455                 460

Ala Gly Lys Glu Leu Thr Asp Ala Val Asn Val Ala Gln Leu Lys Ser
465                 470                 475                 480

Leu Thr Met Lys Ile Ala Gly Asp Thr Gly Asn Ser Asp Asn Glu Lys
                485                 490                 495

Val Gly Ile Trp Glu Gly Thr Leu Lys Val Leu Gly Thr Ser Gly Glu
            500                 505                 510

Ile Lys Thr Ser Ala Ser Asn Asp Thr Ile Thr Leu Lys Leu Asp Glu
        515                 520                 525

Thr Leu Lys Asn Lys Ile Asp Lys Ile Asp Asn Leu Gly Trp Lys Leu
    530                 535                 540

Lys Ile Ala Gln Gly Met Gly Gly Lys Ala Thr Asn Pro Pro Ala Glu
545                 550                 555                 560

Gln Leu Ile Lys Met Asp Gln Thr Val Thr Phe Thr Ala Gly Lys Asn
                565                 570                 575

Ile Lys Leu Glu Gln Ala Gly Gly Asn Ile Thr Ile Ser Thr Ile Gly
            580                 585                 590

Lys Leu Ile Glu Lys Thr Glu Trp Lys Asn Gly Asn Leu Gln Ile Thr
        595                 600                 605

Tyr Thr Asp Gly Ser Ser Asp Thr Ile Ala Lys Gly Lys Asp Gly Lys
    610                 615                 620

Asn Gly Glu Lys Gly Asp Arg Gly Glu Pro Gly Pro Arg Gly Glu Pro
625                 630                 635                 640

Gly Ile Pro Gly Pro Ala Gly Pro Val Gly Pro Met Gly Pro Ala Gly
                645                 650                 655

Ala Ala Gly Leu Val Gly Pro Met Gly Pro Gln Gly Pro Ala Gly Pro
            660                 665                 670

Pro Gly Pro Val Gly Pro Ala Gly Ala Ala Gly Pro Lys Gly Asp Lys
        675                 680                 685

Gly Glu Pro Gly Gln Ala Gly Pro Ala Gly Pro Arg Gly Pro Ala Gly
    690                 695                 700

Pro Lys Gly Asp Thr Gly Gln Arg Gly Glu Thr Gly Ser Ala Gly Pro
705                 710                 715                 720

Ala Gly Pro Lys Gly Glu Pro Gly Pro Lys Gly Glu Gln Gly Ile Pro
                725                 730                 735

Gly Gln Ala Gly Pro Ala Gly Pro Arg Gly Pro Gln Gly Thr Ala Gly
            740                 745                 750

Ala Gln Gly Pro Lys Gly Asp Lys Gly Glu Pro Gly Glu Ala Gly Pro
        755                 760                 765

Ala Gly Pro Arg Gly Pro Ala Gly Pro Lys Gly Asp Ala Gly Pro Lys
    770                 775                 780

Gly Asp Thr Gly Gln Arg Gly Glu Thr Gly Ser Ala Gly Pro Thr Gly
785                 790                 795                 800

Pro Lys Gly Glu Pro Gly Pro Lys Gly Glu Gln Gly Ile Pro Gly Pro
                805                 810                 815

Ala Gly Pro Ala Gly Pro Lys Gly Asp Lys Gly Asp Thr Gly Pro Ala
            820                 825                 830

Gly Pro Gln Gly Pro Ala Gly Pro Thr Gly Pro Gln Asp Pro Ala Gly
```

```
        835                 840                 845

Pro Thr Gly Asn Ser Glu Leu Lys Gly Ile Thr Ser Ile Ala Asn Gly
    850                 855                 860

Asn Asp Ala Thr Lys Ala Asn Gly Ala Lys Ile Thr Leu Ser Ala Gly
865                 870                 875                 880

Ser Thr Asp Lys Thr Val Asn Val Asn Asp Ala Lys Ile Thr Asn Val
                885                 890                 895

Ala Ala Gly Thr Ala Asp Thr Asp Ala Val Asn Val Ser Gln Leu Asn
            900                 905                 910

Thr Lys Ala Ala Ala Ser Lys Thr Glu Val Glu Ala Gly Lys Asn Val
        915                 920                 925

Lys Val Thr Ser Lys Thr Gly Ala Asn Gly Gln Asn Ile Tyr Asn Val
    930                 935                 940

Ser Val Ser Gly Asp Leu Ser Asp Ile Thr Ser Ile Ser Asn Gly Asp
945                 950                 955                 960

Thr Lys Val Ser Leu Gly Lys Asp Lys Gln Gly Asn Pro Val Val Asn
                965                 970                 975

Met Asn Gly Ala Arg Ile Thr Asn Val Gly Asp Gly Ser Ala Glu Gly
            980                 985                 990

Asp Ile Val Asn Val Arg Gln Leu  Asn Lys Val Val Ser  Ser Val Asn
        995                 1000                1005

Thr Gly  Phe Asn Gln Leu Ser  Arg Asp Ile Gly Arg  Val Asp Val
    1010                 1015                1020

Asn Ala  Arg Ala Gly Ile Ala  Ser Ala Gly Ala Met  Ala Asn Leu
    1025                 1030                1035

Pro Gln  Ile Ser Leu Pro Gly  Lys Ser Ala Ile Ser  Val Ser Asn
    1040                 1045                1050

Ala Gln  Tyr Arg Gly Gln Ser  Ala Tyr Ala Ile Gly  Tyr Ser Arg
    1055                 1060                1065

Ile Ser  Asp Asn Gly Lys Trp  Leu Ile Arg Ala Ser  Val Ser Ser
    1070                 1075                1080

Asn Thr  Gln Arg Asp Thr Met  Ile Gly Gly Gly Val  Gly Phe Val
    1085                 1090                1095

Trp


<210> SEQ ID NO 23
<211> LENGTH: 3549
<212> TYPE: DNA
<213> ORGANISM: Haemophilus parasuis

<400> SEQUENCE: 23

atgaataaaa tatttagagt tatttggagt catgctcaac aggcttgggt ggttgtgtct      60

gagttagtaa agtctcacac caaaacatcc gcttacacgg ataaaagagc tcaagtatgc     120

acctcagatt attttttaga taaacagcaa gataaattta aattaagtct tttaagtcta     180

gtattactag gtatattttt tagtccaccg gcaggttcag ctgcatattt tgcaggtggt     240

gctagtgcat cgggtaatgg atatgacgat ggtactattg gtattggtca agagagtaag     300

gcttcgtatg gtgctgttgc tatcggtcag aagtcaaaag ctgaagctag gcataatatt     360

gcgataggtt ttgactcaaa tgcaggaaca agcacaaact ctgttgcgat aggctacgag     420

gctaaagtaa ctggggagga aggaattgcc atcgggaaag agtcaaaagc gggagggaga     480

tctgttgtct taggcggaca agccgaaggg acaactactc aaacagttgt aataggtaac     540

cttgctaaag caagtgcgtc acaatctatt gctattgggg cagatgccaa agcggagggg     600
```

-continued

```
tatggctcca tatcaatcgg tggagatgat ttagatcaaa cggattatca cgctagtaat    660
aatacaaagc agacccgcca aacaacaact gcgaaaggta aagcctctgt tgctattggg    720
gggctgtctt tggctacggg cgacggatct attgttgtag gtcctgtagc atctgcaagt    780
catgttgaag gcattgctat cggtgcgaga agtaagtcta ccaatgagta cggtattgcg    840
gttggtggta gtgcaactgc tggaaagaac gccgttgctg ttggtaggga gtcgaaaggt    900
gctgggacag attccattgc gataggtaat tctgcgagaa caacaggggc agactctgtt    960
gttgtgggtg cccatatcaa tgtgacaggt caaaaatcag tggcagttgg acgccaagca   1020
aatgctggaa gtcattctac tgccttgggt tatatggcct ctgccggtgg tacgcactct   1080
gttgctgtgg gtgaaagtgc catgacaaat gatggtgctg ctagagcaac cgcacttggt   1140
aataataccg ttgtcaccgt gggtggcggt gtggcattgg gttatggctc taaggcagat   1200
agagcaggtg atattgaagg ggcaaaacag tcttattctg taacagcagc aagcagtgtt   1260
gataacggct ttaaatctac aggaagtgtt gataacaatc ctattggtgc ggtttctgtg   1320
ggtaatgaca aaatcaaacg ccaaatcacc aacgttgctg caggtaaaga attaaccgat   1380
gcagtaaacg tggcacagct taaatctttg acgatggaaa ttggtggtga taacaacgta   1440
aatagcccta aagtaggcat ttggaatggc aaacttgaag ttaaaggcac taatgatgaa   1500
atcacgacca aagcggaggg ttcaacaatc acgatttcgt tagaggacaa gattaggaaa   1560
caactggctc agattgccga taaaatgtca tcctttaaga ttaaaacaga taaggataac   1620
aatgaagcta caattaagga tggagatacg atccagttta ccggtgggga aaatataaag   1680
attacccgcg ataataaaaa tctaactttt ggcgtcactt caggtatgtt tagttctaca   1740
acagatggca aattgtcaaa acaaaccgca gggctagcaa ccgttaatga tgtagtatcg   1800
gcagtgaata atgcaggttg gaaactgatg attgcgaaag gggctggtca agcaaatcca   1860
cctgcggcag atcttatcaa aatgggcgat atggcaacct ttaccgctgg aaataatatt   1920
aaattagaac aaacgaacgg aaatattacg atttctacga ttggtaagtt aattgacaaa   1980
gcggaaaatg aaccaaatgg cgatctaaaa attacctata cagatggttc gcatagcact   2040
atcaagaaag gtgaaaaagg agatcgtggc gaaactggcc ctgcgggtcc agcaggtcca   2100
attggtccag tgggtccagc aggggctgct ggagcaacag gaccacaagg tccaaaagga   2160
gaggcaggag cagtgggccc tcaaggtcct acgggtgcag cagggcctag gggtccagtg   2220
ggtcctgctg gtccaaaagg tgatgcaggt cctagaggcg aagctggtcc tgcgggtgca   2280
actggtccta agggggataa aggcgaacca ggacaagcgg gtccagcagg accacgaggc   2340
cctgcgggtc ctaaaggaga tgcaggtcca aaaggtgata caggtcagag aggtgaaact   2400
ggctctgcgg gtccagcggg tccaactgga ccacaaggtg cacctggtcc tgcaggtcca   2460
aaaggagagg caggagcaaa aggcgataag ggtgaccgtg gtgaaacagg agcaatgggc   2520
cctcaaggtc cagtgggtcc aacgggacct aagggtgaca aaggtgatac gggtccaacg   2580
ggatcacaag accctgcggg tccaactgga aattcggaat taaaaggcat tacgtcgatt   2640
gccaatggta acgacgccac caaggcgaat ggggctaaga ttaccttgtc tgcaggttct   2700
acagataaaa cagttaatgt taatgatgcg aaaattacca atgtggcggc tggtacagca   2760
gataccgatg cggtgaatgt gaaacagttg aaatctgcga aaactgaagt ggaatctacc   2820
gatcacagtg tggtgattaa agagcgtcag ggcgataatc agcaaatcgt gtatgatttg   2880
gcggttgcta aaacgaaact cactgcctct gaggataaac gcaccattag tgcagcagat   2940
aaaggcaacc attttgcgac aggagatgaa gtcgcagtag caattaatac cgcaacagca   3000
```

-continued

```
gccgcaagaa ctgaagttga agcgggtaaa aatgtgaaag tgacttcaaa aacgggggca   3060

aatggtcaga atatttacaa tgtgagcgtg tctggagatt taagcgacat tacttcaatt   3120

agtaatggcg atacgaaagt atctttaggt aaagataagc aaggaaatcc agttgtaaat   3180

atgaatggcg ccagaattac caacgttgga gatggtagtg ctgagggcga tattgtgaat   3240

gttcgtcagc tcaacaaagt ggtttcttct gtgaatacag gatttaatca attatcaaga   3300

gatattggtc gtgttgatgt taatgcaaga gcgggtattg cttctgctgt ggcgatggct   3360

aatttgccac aaatttcttt accaggtaaa agtgctattt ctgtttctaa tgcacaatat   3420

cgcgggcaat ctgcctatgc tataggttat tccagaattt ctgataatgg caaatggctt   3480

attcgagcgt ctgttagcag taatactcag cgggatactg cgattggagg aggggtaggt   3540

tttgtgtgg                                                           3549


<210> SEQ ID NO 24
<211> LENGTH: 1183
<212> TYPE: PRT
<213> ORGANISM: haemophilus parasuis

<400> SEQUENCE: 24

Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Gly
    50                  55                  60

Ile Phe Phe Ser Pro Pro Ala Gly Ser Ala Ala Tyr Phe Ala Gly Gly
65                  70                  75                  80

Ala Ser Ala Ser Gly Asn Gly Tyr Asp Asp Gly Thr Ile Gly Ile Gly
                85                  90                  95

Gln Glu Ser Lys Ala Ser Tyr Gly Ala Val Ala Ile Gly Gln Lys Ser
            100                 105                 110

Lys Ala Glu Ala Arg His Asn Ile Ala Ile Gly Phe Asp Ser Asn Ala
        115                 120                 125

Gly Thr Ser Thr Asn Ser Val Ala Ile Gly Tyr Glu Ala Lys Val Thr
    130                 135                 140

Gly Glu Glu Gly Ile Ala Ile Gly Lys Glu Ser Lys Ala Gly Gly Arg
145                 150                 155                 160

Ser Val Val Leu Gly Gly Gln Ala Glu Gly Thr Thr Thr Gln Thr Val
                165                 170                 175

Val Ile Gly Asn Leu Ala Lys Ala Ser Ala Ser Gln Ser Ile Ala Ile
            180                 185                 190

Gly Ala Asp Ala Lys Ala Glu Gly Tyr Gly Ser Ile Ser Ile Gly Gly
        195                 200                 205

Asp Asp Leu Asp Gln Thr Asp Tyr His Ala Ser Asn Asn Thr Lys Gln
    210                 215                 220

Thr Arg Gln Thr Thr Thr Ala Lys Gly Lys Ala Ser Val Ala Ile Gly
225                 230                 235                 240

Gly Leu Ser Leu Ala Thr Gly Asp Gly Ser Ile Val Val Gly Pro Val
                245                 250                 255

Ala Ser Ala Ser His Val Glu Gly Ile Ala Ile Gly Ala Arg Ser Lys
            260                 265                 270

Ser Thr Asn Glu Tyr Gly Ile Ala Val Gly Gly Ser Ala Thr Ala Gly
```

-continued

```
        275                 280                 285

Lys Asn Ala Val Ala Val Gly Arg Glu Ser Lys Gly Ala Gly Thr Asp
    290                 295                 300

Ser Ile Ala Ile Gly Asn Ser Ala Arg Thr Thr Gly Ala Asp Ser Val
305                 310                 315                 320

Val Val Gly Ala His Ile Asn Val Thr Gly Gln Lys Ser Val Ala Val
                325                 330                 335

Gly Arg Gln Ala Asn Ala Gly Ser His Ser Thr Ala Leu Gly Tyr Met
            340                 345                 350

Ala Ser Ala Gly Gly Thr His Ser Val Ala Val Gly Glu Ser Ala Met
        355                 360                 365

Thr Asn Asp Gly Ala Ala Arg Ala Thr Ala Leu Gly Asn Asn Thr Val
    370                 375                 380

Val Thr Val Gly Gly Gly Val Ala Leu Gly Tyr Gly Ser Lys Ala Asp
385                 390                 395                 400

Arg Ala Gly Asp Ile Glu Gly Ala Lys Gln Ser Tyr Ser Val Thr Ala
                405                 410                 415

Ala Ser Ser Val Asp Asn Gly Phe Lys Ser Thr Gly Ser Val Asp Asn
            420                 425                 430

Asn Pro Ile Gly Ala Val Ser Val Gly Asn Asp Lys Ile Lys Arg Gln
        435                 440                 445

Ile Thr Asn Val Ala Ala Gly Lys Glu Leu Thr Asp Ala Val Asn Val
    450                 455                 460

Ala Gln Leu Lys Ser Leu Thr Met Glu Ile Gly Gly Asp Asn Asn Val
465                 470                 475                 480

Asn Ser Pro Lys Val Gly Ile Trp Asn Gly Lys Leu Glu Val Lys Gly
                485                 490                 495

Thr Asn Asp Glu Ile Thr Thr Lys Ala Glu Gly Ser Thr Ile Thr Ile
            500                 505                 510

Ser Leu Glu Asp Lys Ile Arg Lys Gln Leu Ala Gln Ile Ala Asp Lys
        515                 520                 525

Met Ser Ser Phe Lys Ile Lys Thr Asp Lys Asp Asn Asn Glu Ala Thr
    530                 535                 540

Ile Lys Asp Gly Asp Thr Ile Gln Phe Thr Gly Gly Glu Asn Ile Lys
545                 550                 555                 560

Ile Thr Arg Asp Asn Lys Asn Leu Thr Phe Gly Val Thr Ser Gly Met
                565                 570                 575

Phe Ser Ser Thr Thr Asp Gly Lys Leu Ser Lys Gln Thr Ala Gly Leu
            580                 585                 590

Ala Thr Val Asn Asp Val Val Ser Ala Val Asn Asn Ala Gly Trp Lys
        595                 600                 605

Leu Met Ile Ala Lys Gly Ala Gly Gln Ala Asn Pro Pro Ala Ala Asp
    610                 615                 620

Leu Ile Lys Met Gly Asp Met Ala Thr Phe Thr Ala Gly Asn Asn Ile
625                 630                 635                 640

Lys Leu Glu Gln Thr Asn Gly Asn Ile Thr Ile Ser Thr Ile Gly Lys
                645                 650                 655

Leu Ile Asp Lys Ala Glu Asn Glu Pro Asn Gly Asp Leu Lys Ile Thr
            660                 665                 670

Tyr Thr Asp Gly Ser His Ser Thr Ile Lys Lys Gly Glu Lys Gly Asp
        675                 680                 685

Arg Gly Glu Thr Gly Pro Ala Gly Pro Ala Gly Pro Ile Gly Pro Val
    690                 695                 700
```

-continued

```
Gly Pro Ala Gly Ala Ala Gly Ala Thr Gly Pro Gln Gly Pro Lys Gly
705                 710                 715                 720

Glu Ala Gly Ala Val Gly Pro Gln Gly Pro Thr Gly Ala Ala Gly Pro
                725                 730                 735

Arg Gly Pro Val Gly Pro Ala Gly Pro Lys Gly Asp Ala Gly Pro Arg
            740                 745                 750

Gly Glu Ala Gly Pro Ala Gly Ala Thr Gly Pro Lys Gly Asp Lys Gly
        755                 760                 765

Glu Pro Gly Gln Ala Gly Pro Ala Gly Pro Arg Gly Pro Ala Gly Pro
    770                 775                 780

Lys Gly Asp Ala Gly Pro Lys Gly Asp Thr Gly Gln Arg Gly Glu Thr
785                 790                 795                 800

Gly Ser Ala Gly Pro Ala Gly Pro Thr Gly Pro Gln Gly Ala Pro Gly
                805                 810                 815

Pro Ala Gly Pro Lys Gly Glu Ala Gly Ala Lys Gly Asp Lys Gly Asp
            820                 825                 830

Arg Gly Glu Thr Gly Ala Met Gly Pro Gln Gly Pro Val Gly Pro Thr
        835                 840                 845

Gly Pro Lys Gly Asp Lys Gly Asp Thr Gly Pro Thr Gly Ser Gln Asp
    850                 855                 860

Pro Ala Gly Pro Thr Gly Asn Ser Glu Leu Lys Gly Ile Thr Ser Ile
865                 870                 875                 880

Ala Asn Gly Asn Asp Ala Thr Lys Ala Asn Gly Ala Lys Ile Thr Leu
                885                 890                 895

Ser Ala Gly Ser Thr Asp Lys Thr Val Asn Val Asn Asp Ala Lys Ile
            900                 905                 910

Thr Asn Val Ala Ala Gly Thr Ala Asp Thr Asp Ala Val Asn Val Lys
        915                 920                 925

Gln Leu Lys Ser Ala Lys Thr Glu Val Glu Ser Thr Asp His Ser Val
    930                 935                 940

Val Ile Lys Glu Arg Gln Gly Asp Asn Gln Gln Ile Val Tyr Asp Leu
945                 950                 955                 960

Ala Val Ala Lys Thr Lys Leu Thr Ala Ser Glu Asp Lys Arg Thr Ile
                965                 970                 975

Ser Ala Ala Asp Lys Gly Asn His Phe Ala Thr Gly Asp Glu Val Ala
            980                 985                 990

Val Ala Ile Asn Thr Ala Thr Ala  Ala Ala Arg Thr Glu  Val Glu Ala
        995                 1000                1005

Gly Lys  Asn Val Lys Val Thr  Ser Lys Thr Gly Ala  Asn Gly Gln
    1010                1015                1020

Asn Ile  Tyr Asn Val Ser Val  Ser Gly Asp Leu Ser  Asp Ile Thr
    1025                1030                1035

Ser Ile  Ser Asn Gly Asp Thr  Lys Val Ser Leu Gly  Lys Asp Lys
    1040                1045                1050

Gln Gly  Asn Pro Val Val Asn  Met Asn Gly Ala Arg  Ile Thr Asn
    1055                1060                1065

Val Gly  Asp Gly Ser Ala Glu  Gly Asp Ile Val Asn  Val Arg Gln
    1070                1075                1080

Leu Asn  Lys Val Val Ser Ser  Val Asn Thr Gly Phe  Asn Gln Leu
    1085                1090                1095

Ser Arg  Asp Ile Gly Arg Val  Asp Val Asn Ala Arg  Ala Gly Ile
    1100                1105                1110

Ala Ser  Ala Val Ala Met Ala  Asn Leu Pro Gln Ile  Ser Leu Pro
    1115                1120                1125
```

```
Gly Lys  Ser Ala Ile Ser Val  Ser Asn Ala Gln Tyr  Arg Gly Gln
    1130                 1135                 1140

Ser Ala  Tyr Ala Ile Gly Tyr  Ser Arg Ile Ser Asp  Asn Gly Lys
    1145                 1150                 1155

Trp Leu  Ile Arg Ala Ser Val  Ser Ser Asn Thr Gln  Arg Asp Thr
    1160                 1165                 1170

Ala Ile  Gly Gly Gly Val Gly  Phe Val Trp
    1175                 1180
```

<210> SEQ ID NO 25
<211> LENGTH: 3072
<212> TYPE: DNA
<213> ORGANISM: Haemophilus parasuis

<400> SEQUENCE: 25

```
atgaataaaa tatttagagt tatttggagt catgctcaac aggcttgggt ggttgtatct     60
gagttagtaa agtctcatac taaaacatcc gcttacacgg ataaaagagc tcaagtatgc    120
acctcagatt attttttaga taaacagcaa gataaattta aattaagtct tttaagtcta    180
gtattactaa gtatattttt taatccagta gtaggtgcag atcgtcataa aggaactcca    240
tatcttcaag atggtgctac taaatcgagt ctaggaagtg acgacggtac tattggtatt    300
ggtaaaagta gtaaggctgg gtatggtgct attgctatcg gtcagtattc aaaagctgaa    360
gctaggcata atattgcgat aggttatgac tcaaatgcag gaacaagcgc aaactctatt    420
acgataggct acaatactaa agtaagtggg gagcaagcaa ttgccatcgg gaaacagtca    480
aaagcgggaa aggaatctgt tgtcttaggc gggcaagcca aaggggaagg tactcaaaca    540
gttgtagtag gtaaccttgc tattgcaagt aagttacaat ctattgctat cggtgcgaat    600
agtaagtcta ccgatgagta cggtattgcg gttggtggta gtgcaactgc tactggaaaa    660
tacgccgttg ctcttggttg gggctcgaaa ggtgttggga cagattccat tgcgataggt    720
aagtctgcga caacagcagg ggcagactct gttgttgtgg gtgcccatat caatgtgaca    780
gatggacaat tagtggcaat tggacgccaa gcaaatgctg gaagtcattc tactgccttg    840
ggttataaag cctctgccgg tggtatgcac tctgttgctg tgggtgaaga agccaaaaca    900
aatgatggtg ctgctagagc aaccgcactt ggtaataata ccgttgtcac cgtgggtggc    960
ggtgtggcat tgggttatgg atctaatgca agtacagctg gcggtgtagt ggggttaaaa   1020
caagatcatt ctgtcacaac gggaacaagc actgaagcta acggctttaa atccacacaa   1080
aatgttgatg gtaatgatat tggtgcagtt tctgtcggta tgggctcagg taataaactc   1140
atcaaacgcc aaatcaccaa cgttgcggct ggtaaagaat taaccgatgc ggtaaacgtg   1200
gcacagctta aatctttgac gatgaaaatt ggtggtgata ccaatgataa tacacagcca   1260
aaagtggggt tgtgggatgg caaacttgaa gttaaaggca ctagtgatga aatcaagacc   1320
aatgcgtcta actcaaccat cacaataggt ttagatcaaa agattaagga tcaactgagt   1380
gaaattgcga agaaaatgtc gtcttttaag attaaaacag ataacactga agctacaatt   1440
acgaatggag atacaatcca gtttaccgct ggggacaata taaagattac cagcaataat   1500
aaaaatctaa attttgccct cacttcaggt aactttactg taaatgatgg cagattatca   1560
agacaaactg cagggcttgc tactgttgat actgtagtat cggcagtgaa taatgctggt   1620
tggaaacttg caattgcttc gggaacgggg ggtcaagcaa cgaatacttc atatcttatc   1680
aaaatgggcg atccggcaaa atttattgca ggcaataata ttaaattaga acaaacgaac   1740
ggaaatatta cgatttctac gattggtaag ttaattgaaa agactgaatg gaaagatggt   1800
```

-continued

```
ggtttgaaaa ttacttatac ggatggcacc agtgatacta ttgctaaggg gaaagacggt   1860

aaaaatggtg agaaaggtga tagaggggaa caagggccag cagggcctag aggcgaagct   1920

ggtcctagag gcgaagctgg tccagtgggt ccagcaggac cacgaggacc gcagggaaca   1980

acgggtgctc agggacctaa gggggataaa ggcgaaccag gacaagcggg tccagcagga   2040

ccacgaggcc ctgcgggtcc taaaggagat gcaggtccaa aaggtgatac aggtcagaga   2100

ggtgaaactg gccctgcggg tccagcaggt ccagctggac cacaaggacc gcagggaaca   2160

gcgggtgctc agggacagaa gggggataaa ggcgaaccag gacaagcggg tccaaaagga   2220

gatacaggtc agaaaggtga aactggccct gcgggtccaa cgggacctaa gggtgacaaa   2280

ggtgatacgg gtccagcagg atcacaagga cctacgggtc caactggaaa ttcggaatta   2340

aaaggcatta cgtcgattgc caatggtaac gacgccacca aggcgaatgg ggctaagatt   2400

accttgtctg caggttctac agataaaaca gttaatgtta atgatgcgaa aattaccaat   2460

gtggcggctg gtacagcaga tactgatgcg gtgaatgtga gccagttaaa tactaaggca   2520

gcagcttcaa aaacagaggt tgaagcgggt aaaaatgtga aagtgacttc aaaaacgggg   2580

gcaaatggtc agaatattta caatgtgagc gtgtctggag atttaagcga cattacttca   2640

attagtaatg gcgatacgaa agtatcttta ggtaaagata agcaaggaaa tccagttgta   2700

aatatgaatg gtgccagaat taccaatgtt ggagatggta gtgctgaggg cgatattgtg   2760

aatgtgcgtc agctcaacaa agtggtttct tctgtgaata caggatttaa tcaattatca   2820

agagatattg gtcgtgttga tgttaatgca agagcgggta ttgcttctgc tgtggcgatg   2880

gctaatttgc cacaaatttc tttaccaggt aaaagtgcta tttctgtttc taatgcacaa   2940

tatcgcgggc aatctgccta tgctataggt tattccaaaa tttctgataa tggcaaatgg   3000

cttattcgag cgtctgttag cagtaatact cagcgggata ctgcgattgg aggaggggta   3060

ggttttgtgt gg                                                       3072
```

```
<210> SEQ ID NO 26
<211> LENGTH: 1024
<212> TYPE: PRT
<213> ORGANISM: haemophilus parasuis

<400> SEQUENCE: 26

Met Asn Lys Ile Phe Arg Val Ile Trp Ser His Ala Gln Gln Ala Trp
1               5                   10                  15

Val Val Val Ser Glu Leu Val Lys Ser His Thr Lys Thr Ser Ala Tyr
            20                  25                  30

Thr Asp Lys Arg Ala Gln Val Cys Thr Ser Asp Tyr Phe Leu Asp Lys
        35                  40                  45

Gln Gln Asp Lys Phe Lys Leu Ser Leu Leu Ser Leu Val Leu Leu Ser
    50                  55                  60

Ile Phe Phe Asn Pro Val Val Gly Ala Asp Arg His Lys Gly Thr Pro
65                  70                  75                  80

Tyr Leu Gln Asp Gly Ala Thr Lys Ser Ser Leu Gly Ser Asp Asp Gly
                85                  90                  95

Thr Ile Gly Ile Gly Lys Ser Ser Lys Ala Gly Tyr Gly Ala Ile Ala
            100                 105                 110

Ile Gly Gln Tyr Ser Lys Ala Glu Ala Arg His Asn Ile Ala Ile Gly
        115                 120                 125

Tyr Asp Ser Asn Ala Gly Thr Ser Ala Asn Ser Ile Thr Ile Gly Tyr
    130                 135                 140
```

-continued

```
Asn Thr Lys Val Ser Gly Glu Gln Ala Ile Ala Ile Gly Lys Gln Ser
145                 150                 155                 160

Lys Ala Gly Lys Glu Ser Val Val Leu Gly Gly Gln Ala Lys Gly Glu
                165                 170                 175

Gly Thr Gln Thr Val Val Val Gly Asn Leu Ala Ile Ala Ser Lys Leu
            180                 185                 190

Gln Ser Ile Ala Ile Gly Ala Asn Ser Lys Ser Thr Asp Glu Tyr Gly
        195                 200                 205

Ile Ala Val Gly Gly Ser Ala Thr Ala Thr Gly Lys Tyr Ala Val Ala
    210                 215                 220

Leu Gly Trp Gly Ser Lys Gly Val Gly Thr Asp Ser Ile Ala Ile Gly
225                 230                 235                 240

Lys Ser Ala Thr Thr Ala Gly Ala Asp Ser Val Val Val Gly Ala His
                245                 250                 255

Ile Asn Val Thr Asp Gly Gln Leu Val Ala Ile Gly Arg Gln Ala Asn
            260                 265                 270

Ala Gly Ser His Ser Thr Ala Leu Gly Tyr Lys Ala Ser Ala Gly Gly
        275                 280                 285

Met His Ser Val Ala Val Gly Glu Glu Ala Lys Thr Asn Asp Gly Ala
    290                 295                 300

Ala Arg Ala Thr Ala Leu Gly Asn Asn Thr Val Val Thr Val Gly Gly
305                 310                 315                 320

Gly Val Ala Leu Gly Tyr Gly Ser Asn Ala Ser Thr Ala Gly Gly Val
                325                 330                 335

Val Gly Leu Lys Gln Asp His Ser Val Thr Thr Gly Thr Ser Thr Glu
            340                 345                 350

Ala Asn Gly Phe Lys Ser Thr Gln Asn Val Asp Gly Asn Asp Ile Gly
        355                 360                 365

Ala Val Ser Val Gly Met Gly Ser Gly Asn Lys Leu Ile Lys Arg Gln
    370                 375                 380

Ile Thr Asn Val Ala Ala Gly Lys Glu Leu Thr Asp Ala Val Asn Val
385                 390                 395                 400

Ala Gln Leu Lys Ser Leu Thr Met Lys Ile Gly Gly Asp Thr Asn Asp
                405                 410                 415

Asn Thr Gln Pro Lys Val Gly Leu Trp Asp Gly Lys Leu Glu Val Lys
            420                 425                 430

Gly Thr Ser Asp Glu Ile Lys Thr Asn Ala Ser Asn Ser Thr Ile Thr
        435                 440                 445

Ile Gly Leu Asp Gln Lys Ile Lys Asp Gln Leu Ser Glu Ile Ala Lys
    450                 455                 460

Lys Met Ser Ser Phe Lys Ile Lys Thr Asp Asn Thr Glu Ala Thr Ile
465                 470                 475                 480

Thr Asn Gly Asp Thr Ile Gln Phe Thr Ala Gly Asp Asn Ile Lys Ile
                485                 490                 495

Thr Ser Asn Asn Lys Asn Leu Asn Phe Ala Leu Thr Ser Gly Asn Phe
            500                 505                 510

Thr Val Asn Asp Gly Arg Leu Ser Arg Gln Thr Ala Gly Leu Ala Thr
        515                 520                 525

Val Asp Thr Val Val Ser Ala Val Asn Asn Ala Gly Trp Lys Leu Ala
    530                 535                 540

Ile Ala Ser Gly Thr Gly Gly Gln Ala Thr Asn Thr Ser Tyr Leu Ile
545                 550                 555                 560

Lys Met Gly Asp Pro Ala Lys Phe Ile Ala Gly Asn Asn Ile Lys Leu
                565                 570                 575
```

```
Glu Gln Thr Asn Gly Asn Ile Thr Ile Ser Thr Ile Gly Lys Leu Ile
            580                 585                 590

Glu Lys Thr Glu Trp Lys Asp Gly Gly Leu Lys Ile Thr Tyr Thr Asp
        595                 600                 605

Gly Thr Ser Asp Thr Ile Ala Lys Gly Lys Asp Gly Lys Asn Gly Glu
    610                 615                 620

Lys Gly Asp Arg Gly Glu Gln Gly Pro Ala Gly Pro Arg Gly Glu Ala
625                 630                 635                 640

Gly Pro Arg Gly Glu Ala Gly Pro Val Gly Pro Ala Gly Pro Arg Gly
                645                 650                 655

Pro Gln Gly Thr Thr Gly Ala Gln Gly Pro Lys Gly Asp Lys Gly Glu
            660                 665                 670

Pro Gly Gln Ala Gly Pro Ala Gly Pro Arg Gly Pro Ala Gly Pro Lys
        675                 680                 685

Gly Asp Ala Gly Pro Lys Gly Asp Thr Gly Gln Arg Gly Glu Thr Gly
    690                 695                 700

Pro Ala Gly Pro Ala Gly Pro Ala Gly Pro Gln Gly Pro Gln Gly Thr
705                 710                 715                 720

Ala Gly Ala Gln Gly Gln Lys Gly Asp Lys Gly Glu Pro Gly Gln Ala
                725                 730                 735

Gly Pro Lys Gly Asp Thr Gly Gln Lys Gly Glu Thr Gly Pro Ala Gly
            740                 745                 750

Pro Thr Gly Pro Lys Gly Asp Lys Gly Asp Thr Gly Pro Ala Gly Ser
        755                 760                 765

Gln Gly Pro Thr Gly Pro Thr Gly Asn Ser Glu Leu Lys Gly Ile Thr
    770                 775                 780

Ser Ile Ala Asn Gly Asn Asp Ala Thr Lys Ala Asn Gly Ala Lys Ile
785                 790                 795                 800

Thr Leu Ser Ala Gly Ser Thr Asp Lys Thr Val Asn Val Asn Asp Ala
                805                 810                 815

Lys Ile Thr Asn Val Ala Ala Gly Thr Ala Asp Thr Asp Ala Val Asn
            820                 825                 830

Val Ser Gln Leu Asn Thr Lys Ala Ala Ala Ser Lys Thr Glu Val Glu
        835                 840                 845

Ala Gly Lys Asn Val Lys Val Thr Ser Lys Thr Gly Ala Asn Gly Gln
    850                 855                 860

Asn Ile Tyr Asn Val Ser Val Ser Gly Asp Leu Ser Asp Ile Thr Ser
865                 870                 875                 880

Ile Ser Asn Gly Asp Thr Lys Val Ser Leu Gly Lys Asp Lys Gln Gly
                885                 890                 895

Asn Pro Val Val Asn Met Asn Gly Ala Arg Ile Thr Asn Val Gly Asp
            900                 905                 910

Gly Ser Ala Glu Gly Asp Ile Val Asn Val Arg Gln Leu Asn Lys Val
        915                 920                 925

Val Ser Ser Val Asn Thr Gly Phe Asn Gln Leu Ser Arg Asp Ile Gly
    930                 935                 940

Arg Val Asp Val Asn Ala Arg Ala Gly Ile Ala Ser Ala Val Ala Met
945                 950                 955                 960

Ala Asn Leu Pro Gln Ile Ser Leu Pro Gly Lys Ser Ala Ile Ser Val
                965                 970                 975

Ser Asn Ala Gln Tyr Arg Gly Gln Ser Ala Tyr Ala Ile Gly Tyr Ser
            980                 985                 990

Lys Ile Ser Asp Asn Gly Lys Trp  Leu Ile Arg Ala Ser  Val Ser Ser
```

```
        995                 1000                1005

Asn Thr  Gln Arg Asp Thr Ala  Ile Gly Gly Gly Val  Gly Phe Val
    1010                 1015                1020

Trp
```

<210> SEQ ID NO 27
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 27
atgaataaaa tatttagagt tatttgg 27

<210> SEQ ID NO 28
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 28
ccacacaaaa cctacccctc ctcc 24

<210> SEQ ID NO 29
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 29
ccactgataa cctaccccca cagag 25

<210> SEQ ID NO 30
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 30
ccactgtaat gcaatacctg cacc 24

<210> SEQ ID NO 31
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 31
gactgatcat gaataaaata tttagagtta tttgg 35

<210> SEQ ID NO 32
<211> LENGTH: 36
<212> TYPE: DNA
<213> ORGANISM: Artificial sequence
<220> FEATURE:
<223> OTHER INFORMATION: Synthetic Oligonucleotide

<400> SEQUENCE: 32
gactgacata tgaataaaat atttagagtt atttgg 36

<210> SEQ ID NO 33
<211> LENGTH: 33
<212> TYPE: DNA
<213> ORGANISM: Artificial sequence
<220> FEATURE:
<223> OTHER INFORMATION: Synthetic Oligonucleotide

<400> SEQUENCE: 33
ttactcgagc cacacaaaac ctacccctcc tcc 33

<210> SEQ ID NO 34
<211> LENGTH: 37
<212> TYPE: DNA
<213> ORGANISM: Artificial sequence
<220> FEATURE:
<223> OTHER INFORMATION: Synthetic Oligonucleotide

<400> SEQUENCE: 34
tagttagtcg acccactgat aacctacccc cacagag 37

<210> SEQ ID NO 35
<211> LENGTH: 33
<212> TYPE: DNA
<213> ORGANISM: Artificial sequence
<220> FEATURE:
<223> OTHER INFORMATION: Synthetic Oligonucleotide

<400> SEQUENCE: 35
ttactcgagc cactgtaatg caatacctgc acc 33

<210> SEQ ID NO 36
<211> LENGTH: 17
<212> TYPE: DNA
<213> ORGANISM: Artificial sequence
<220> FEATURE:
<223> OTHER INFORMATION: Synthetic Oligonucleotide

<400> SEQUENCE: 36
gtaaaacgac ggccagt 17

<210> SEQ ID NO 37
<211> LENGTH: 16
<212> TYPE: DNA
<213> ORGANISM: Artificial sequence
<220> FEATURE:
<223> OTHER INFORMATION: Synthetic Oligonucleotide

<400> SEQUENCE: 37
aacagctatg accatg 16

<210> SEQ ID NO 38
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 38
taatacgact cactatagg 19

<210> SEQ ID NO 39
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 39

-continued

```
gctagttatt gctcagcgg                                                    19


<210> SEQ ID NO 40
<211> LENGTH: 179
<212> TYPE: PRT
<213> ORGANISM: Artificial Sequence
<220> FEATURE:
<223> OTHER INFORMATION: Synthetic polypeptide

<400> SEQUENCE: 40

Val Ser Glu Leu Val Lys Ser His Thr Lys Thr Ser Ala Tyr Thr Asp
1               5                   10                  15

Lys Arg Ser Gln Leu Cys Thr Ser Asp Tyr Phe Leu His Lys Gln Gln
            20                  25                  30

Asp Lys Phe Lys Leu Ser Leu Leu Ser Leu Val Leu Leu Ser Ile Phe
        35                  40                  45

Phe Ser Pro Val Gly Leu Ala Val Phe Ile Gln Asp Gly Ser Thr Asn
    50                  55                  60

Val Ala Pro Phe Tyr Asp Asn Gly Ala Ile Gly Ile Gly Tyr Arg Ser
65                  70                  75                  80

Tyr Val Gly Asn Ser Gly Val Val Ile Gly Lys His Ala Val Ala Arg
                85                  90                  95

Asp Thr Val Ala Val Ala Ile Gly Tyr Ser Ala Glu Val Val Gly His
            100                 105                 110

Asp Gly Val Ala Val Gly Ala His Ala Gln Ala Arg Tyr Arg Ser Val
        115                 120                 125

Ala Ser Gly Tyr Ser Ala Lys Ala Leu Gly Gln Arg Ser Val Ala Ile
    130                 135                 140

Gly Asp Ser Ala Glu Val Asn Ser Gly Ala Thr Arg Ala Ile Ala Leu
145                 150                 155                 160

Gly His Asn Ser Ile Val Thr Val Ala Gly Gly Val Ala Leu Gly Tyr
                165                 170                 175

Gly Ser Arg
```